(12) United States Patent
Wilkinson et al.

(10) Patent No.: US 8,603,228 B2
(45) Date of Patent: Dec. 10, 2013

(54) POWER MANAGEMENT SYSTEMS AND METHODS FOR USE IN AN OXYGEN CONCENTRATOR

(75) Inventors: William R. Wilkinson, Lakeway, TX (US); Allan Sten Westersten, Georgetown, CA (US); Alaa Hassan, Austin, TX (US)

(73) Assignee: Inova Labs, Inc., Austin, TX (US)

( * ) Notice: Subject to any disclaimer, the term of this patent is extended or adjusted under 35 U.S.C. 154(b) by 289 days.

(21) Appl. No.: 12/876,874

(22) Filed: Sep. 7, 2010

(65) Prior Publication Data

US 2012/0055340 A1 Mar. 8, 2012

(51) Int. Cl.
*B01D 53/02* (2006.01)

(52) U.S. Cl.
USPC ............. 96/115; 96/133; 95/130; 128/205.27

(58) Field of Classification Search
USPC ................... 128/205.27; 96/115, 133; 95/130
See application file for complete search history.

(56) References Cited

U.S. PATENT DOCUMENTS

| | | | |
|---|---|---|---|
| 3,768,468 A | 10/1973 | Cox | |
| 4,194,890 A | 3/1980 | McCombs et al. | |
| 4,302,224 A | 11/1981 | McCombs et al. | |
| 4,331,455 A | 5/1982 | Sato | |
| 4,342,573 A | 8/1982 | McCombs et al. | |
| 4,349,357 A | 9/1982 | Russell | |
| 4,491,459 A | 1/1985 | Pinkerton | |
| 4,519,387 A | 5/1985 | Durkan et al. | |
| 4,550,276 A | 10/1985 | Callahan et al. | |
| 4,576,616 A | 3/1986 | Mottram et al. | |
| 4,612,928 A | 9/1986 | Tiep et al. | |
| 4,630,482 A | 12/1986 | Traina | |
| 4,681,099 A | 7/1987 | Sato et al. | |
| 4,698,075 A | 10/1987 | Dechene | |
| 4,813,979 A | 3/1989 | Miller et al. | |
| 4,857,086 A | 8/1989 | Kawai | |
| 4,859,217 A | 8/1989 | Chao | |
| 4,892,566 A | 1/1990 | Bansal et al. | |
| 4,925,464 A | 5/1990 | Rabenau et al. | |
| 4,938,066 A | 7/1990 | Dorr | |
| 4,938,212 A | 7/1990 | Snook et al. | |
| 4,968,329 A | 11/1990 | Keefer | |
| 4,971,049 A | 11/1990 | Rotariu et al. | |

(Continued)

FOREIGN PATENT DOCUMENTS

| | | |
|---|---|---|
| EP | 1205231 | 5/2002 |
| EP | 1568391 | 8/2005 |

(Continued)

OTHER PUBLICATIONS

Bonnema, Lisa. "Breathing Easy with Plastic Blends"; http://www.appliancemagazine. com/editorial.php?articl=927&zibe=211 &first=1; issue: Apr. 2005 Appliance Magazine; downloaded on Jul. 26, 2007; 4 pages.

(Continued)

*Primary Examiner* — Christopher P Jones
(74) *Attorney, Agent, or Firm* — Meyertons, Hood, Kivlin, Kowert & Goetzel, P.C.; Eric B. Meyertons

(57) ABSTRACT

Described herein are various embodiments of an oxygen concentrator system In some embodiment, an oxygen concentrator system includes improved charging and battery control circuits.

25 Claims, 21 Drawing Sheets

(56) References Cited

U.S. PATENT DOCUMENTS

| | | |
|---|---|---|
| 4,971,609 A | 11/1990 | Pawlos |
| 4,973,339 A | 11/1990 | Bansal |
| 4,986,269 A | 1/1991 | Hakkinen |
| 5,004,485 A | 4/1991 | Hamlin et al. |
| 5,024,219 A | 6/1991 | Dietz |
| 5,048,515 A | 9/1991 | Sanso |
| 5,052,400 A | 10/1991 | Dietz |
| 5,060,506 A | 10/1991 | Douglas |
| 5,060,514 A | 10/1991 | Aylsworth |
| 5,069,688 A | 12/1991 | Wells |
| 5,099,193 A | 3/1992 | Moseley et al. |
| 5,099,837 A | 3/1992 | Russel et al. |
| 5,108,467 A | 4/1992 | Schroter et al. |
| 5,129,924 A | 7/1992 | Schultz |
| 5,146,918 A | 9/1992 | Kallok et al. |
| 5,176,721 A | 1/1993 | Hay et al. |
| 5,223,004 A | 6/1993 | Eteve et al. |
| 5,268,021 A | 12/1993 | Hill et al. |
| 5,275,642 A | 1/1994 | Bassine |
| 5,340,381 A | 8/1994 | Vorih |
| 5,351,522 A | 10/1994 | Lura |
| 5,378,345 A | 1/1995 | Taylor et al. |
| 5,469,372 A | 11/1995 | McBrearty et al. |
| 5,470,378 A | 11/1995 | Kandybin et al. |
| 5,474,595 A | 12/1995 | McCombs |
| 5,503,146 A | 4/1996 | Froehlich et al. |
| 5,549,720 A | 8/1996 | Miller et al. |
| 5,575,282 A | 11/1996 | Knoch et al. |
| 5,578,115 A | 11/1996 | Cole |
| 5,593,478 A | 1/1997 | Hill et al. |
| 5,603,315 A | 2/1997 | Sasso |
| 5,672,195 A | 9/1997 | Moreau et al. |
| 5,682,877 A | 11/1997 | Mondry |
| 5,697,364 A | 12/1997 | Chua et al. |
| 5,730,778 A | 3/1998 | Hill et al. |
| 5,733,359 A | 3/1998 | Doong et al. |
| 5,735,268 A | 4/1998 | Chua et al. |
| 5,746,806 A | 5/1998 | Aylsworth et al. |
| 5,764,534 A | 6/1998 | Goetting |
| 5,766,310 A | 6/1998 | Cramer |
| 5,792,665 A | 8/1998 | Morrow |
| 5,827,358 A | 10/1998 | Kulish et al. |
| 5,839,434 A | 11/1998 | Enterline |
| 5,858,062 A | 1/1999 | McCulloh et al. |
| 5,858,063 A | 1/1999 | Cao et al. |
| 5,865,174 A | 2/1999 | Kloeppel |
| 5,890,490 A | 4/1999 | Aylsworth et al. |
| 5,893,944 A | 4/1999 | Dong |
| 5,906,672 A | 5/1999 | Michaels et al. |
| 5,913,307 A | 6/1999 | Taieb et al. |
| 5,917,135 A | 6/1999 | Michaels et al. |
| 5,922,107 A | 7/1999 | Labasque et al. |
| 5,928,189 A | 7/1999 | Phillips et al. |
| 5,961,694 A | 10/1999 | Monereau et al. |
| 5,968,236 A | 10/1999 | Bassine |
| 5,988,465 A | 11/1999 | Vitale et al. |
| 6,017,315 A | 1/2000 | Starr et al. |
| 6,030,435 A | 2/2000 | Monereau et al. |
| 6,065,473 A | 5/2000 | McCombs et al. |
| 6,068,680 A | 5/2000 | Kulish et al. |
| 6,156,101 A | 12/2000 | Naheiri et al. |
| 6,186,142 B1 | 2/2001 | Schmidt et al. |
| 6,186,477 B1 | 2/2001 | McCombs et al. |
| 6,192,883 B1 | 2/2001 | Miller |
| 6,220,244 B1 | 4/2001 | McLaughlin |
| 6,238,458 B1 | 5/2001 | Monereau |
| 6,253,767 B1 | 7/2001 | Mantz |
| 6,302,107 B1 | 10/2001 | Richey et al. |
| 6,314,957 B1 | 11/2001 | Boissin et al. |
| 6,342,040 B1 | 1/2002 | Starr et al. |
| 6,346,139 B1 | 2/2002 | Czabala |
| 6,371,114 B1 | 4/2002 | Schmidt et al. |
| 6,371,117 B1 | 4/2002 | Lindqvist et al. |
| 6,382,931 B1 | 5/2002 | Czabala et al. |
| 6,394,089 B1 | 5/2002 | Cantrill et al. |
| 6,395,065 B1 | 5/2002 | Murdoch et al. |
| 6,427,690 B1 | 8/2002 | McCombs et al. |
| 6,446,630 B1 | 9/2002 | Todd, Jr. |
| 6,478,850 B1 | 11/2002 | Warren |
| 6,478,857 B2 | 11/2002 | Czabala |
| 6,484,721 B1 | 11/2002 | Bliss |
| 6,511,526 B2 | 1/2003 | Jagger et al. |
| 6,514,318 B2 | 2/2003 | Keefer |
| 6,520,176 B1 | 2/2003 | Dubois et al. |
| 6,527,830 B1 | 3/2003 | Neu et al. |
| 6,532,958 B1 | 3/2003 | Buan et al. |
| 6,536,431 B1 | 3/2003 | Simler |
| 6,547,851 B2 | 4/2003 | Warren |
| 6,551,384 B1 | 4/2003 | Ackley et al. |
| 6,558,451 B2 | 5/2003 | McCombs et al. |
| 6,561,187 B2 | 5/2003 | Schmidt et al. |
| 6,605,136 B1 | 8/2003 | Graham et al. |
| 6,629,525 B2 | 10/2003 | Hill et al. |
| 6,651,658 B1 | 11/2003 | Hill et al. |
| 6,655,383 B1 | 12/2003 | Lundberg |
| 6,669,758 B1 | 12/2003 | Hart et al. |
| 6,691,702 B2 | 2/2004 | Appel et al. |
| 6,694,973 B1 | 2/2004 | Dunhao et al. |
| 6,698,423 B1 | 3/2004 | Honkonen et al. |
| 6,699,307 B1 | 3/2004 | Lomax |
| 6,702,880 B2 | 3/2004 | Roberts et al. |
| 6,712,876 B2 | 3/2004 | Cao et al. |
| 6,712,877 B2 | 3/2004 | Cao et al. |
| 6,749,405 B2 | 6/2004 | Bassine |
| 6,755,895 B2 | 6/2004 | Lomax et al. |
| 6,764,534 B2 | 7/2004 | McCombs et al. |
| 6,790,260 B2 | 9/2004 | Ackley et al. |
| 6,802,889 B2 | 10/2004 | Graham et al. |
| 6,824,590 B2 | 11/2004 | Dee et al. |
| 6,827,760 B2 | 12/2004 | Kutt et al. |
| 6,837,244 B2 | 1/2005 | Yagi et al. |
| 6,866,041 B2 | 3/2005 | Hardy et al. |
| 6,866,950 B2 | 3/2005 | Connor et al. |
| 6,896,721 B1 | 5/2005 | Lynn |
| 6,908,503 B2 | 6/2005 | McCombs et al. |
| 6,918,953 B2 | 7/2005 | Lomax et al. |
| 6,929,683 B2 | 8/2005 | Lomax et al. |
| 6,935,460 B2 | 8/2005 | McCombs et al. |
| 6,938,619 B1 | 9/2005 | Hickle |
| 6,949,133 B2 | 9/2005 | McCombs et al. |
| 7,007,694 B2 | 3/2006 | Aylsworth et al. |
| 7,011,092 B2 | 3/2006 | McCombs et al. |
| 7,013,898 B2 | 3/2006 | Rashad et al. |
| 7,037,358 B2 | 5/2006 | Babicki et al. |
| 7,059,323 B2 | 6/2006 | Kullik et al. |
| 7,066,985 B2 | 6/2006 | Deane et al. |
| 7,077,133 B2 | 7/2006 | Yagi et al. |
| 7,105,038 B2 | 9/2006 | Lee et al. |
| 7,114,932 B1 | 10/2006 | Bassine |
| 7,121,276 B2 | 10/2006 | Jagger et al. |
| 7,122,073 B1 | 10/2006 | Notaro et al. |
| 7,135,059 B2 | 11/2006 | Deane et al. |
| 7,156,903 B2 | 1/2007 | McCombs |
| 7,171,963 B2 | 2/2007 | Jagger et al. |
| 7,178,563 B2 | 2/2007 | Richey et al. |
| 7,179,326 B2 | 2/2007 | Nakamura et al. |
| 7,204,249 B1 | 4/2007 | Richey et al. |
| 7,213,468 B2 | 5/2007 | Fujimoto |
| 7,222,624 B2 | 5/2007 | Rashad et al. |
| 7,225,809 B1 | 6/2007 | Bowen et al. |
| 7,279,029 B2 | 10/2007 | Occhialini et al. |
| 7,306,657 B2 | 12/2007 | Yagi et al. |
| 7,329,304 B2 | 2/2008 | Bliss et al. |
| 7,329,354 B2 | 2/2008 | Mullee |
| 7,396,390 B2 | 7/2008 | Hayashi et al. |
| 7,402,193 B2 | 7/2008 | Bliss et al. |
| 7,431,032 B2 | 10/2008 | Jagger et al. |
| 7,438,745 B2 | 10/2008 | Deane et al. |
| 7,473,299 B2 | 1/2009 | Occhialini et al. |
| 7,565,907 B2 | 7/2009 | Curti et al. |
| 7,582,138 B2 | 9/2009 | Lessi et al. |
| 7,585,351 B2 | 9/2009 | Deane et al. |
| 7,604,004 B2 | 10/2009 | Jagger et al. |
| 7,604,005 B2 | 10/2009 | Jagger et al. |

(56) References Cited

U.S. PATENT DOCUMENTS

| | | | |
|---|---|---|---|
| 7,686,870 B1 | 3/2010 | Deane et al. | |
| 7,708,802 B1 | 5/2010 | Deane et al. | |
| 7,730,887 B2 | 6/2010 | Deane et al. | |
| 7,753,996 B1 | 7/2010 | Deane et al. | |
| 7,766,010 B2 | 8/2010 | Jagger et al. | |
| 7,780,768 B2 | 8/2010 | Taylor et al. | |
| 7,837,761 B2 | 11/2010 | Bliss et al. | |
| 7,841,343 B2 | 11/2010 | Deane et al. | |
| 7,857,894 B2 | 12/2010 | Taylor et al. | |
| 7,866,315 B2 | 1/2011 | Jagger et al. | |
| 7,922,789 B1 | 4/2011 | Deane et al. | |
| 8,016,918 B2 | 9/2011 | Labuda et al. | |
| 8,020,558 B2 | 9/2011 | Christopher et al. | |
| 8,142,544 B2 | 3/2012 | Taylor et al. | |
| 8,147,597 B2 | 4/2012 | Dolensky et al. | |
| 2003/0006024 A1 | 1/2003 | Wang | |
| 2003/0111081 A1 | 6/2003 | Gupta | |
| 2003/0140924 A1 | 7/2003 | Aylsworth et al. | |
| 2004/0050255 A1 | 3/2004 | Simonds | |
| 2004/0159323 A1 | 8/2004 | Schmidt et al. | |
| 2004/0182394 A1 | 9/2004 | Alvey et al. | |
| 2005/0066976 A1 | 3/2005 | Wondka | |
| 2005/0103343 A1 | 5/2005 | Gosweiler | |
| 2005/0192538 A1 | 9/2005 | Voege | |
| 2006/0102181 A1 | 5/2006 | McCombs et al. | |
| 2006/0112962 A1 | 6/2006 | Tebbutt et al. | |
| 2006/0117957 A1 | 6/2006 | McCombs | |
| 2006/0174871 A1 | 8/2006 | Jagger et al. | |
| 2006/0174875 A1 | 8/2006 | Jagger et al. | |
| 2006/0174876 A1 | 8/2006 | Jagger et al. | |
| 2006/0174877 A1 | 8/2006 | Jagger et al. | |
| 2006/0174880 A1 | 8/2006 | Jagger et al. | |
| 2006/0174881 A1 | 8/2006 | Jagger et al. | |
| 2006/0174882 A1 | 8/2006 | Jagger et al. | |
| 2006/0185668 A1 | 8/2006 | Jagger et al. | |
| 2006/0207594 A1 | 9/2006 | Stenzler et al. | |
| 2006/0230931 A1 | 10/2006 | Bliss et al. | |
| 2006/0230939 A1 | 10/2006 | Bliss et al. | |
| 2006/0266357 A1 | 11/2006 | McCombs et al. | |
| 2007/0039466 A1 | 2/2007 | Nawata et al. | |
| 2007/0044799 A1 | 3/2007 | Hete et al. | |
| 2007/0056583 A1 | 3/2007 | Jagger et al. | |
| 2007/0056584 A1 | 3/2007 | Jagger et al. | |
| 2007/0137487 A1 | 6/2007 | Whitley et al. | |
| 2007/0169623 A1 | 7/2007 | Lee et al. | |
| 2007/0283958 A1 | 12/2007 | Naghavi | |
| 2008/0053441 A1 | 3/2008 | Gottlib et al. | |
| 2008/0078392 A1 | 4/2008 | Pelletier et al. | |
| 2008/0223367 A1 | 9/2008 | Cox et al. | |
| 2009/0065007 A1 | 3/2009 | Wilkinson et al. | |
| 2009/0065526 A1 | 3/2009 | Sprinkle | |
| 2009/0107500 A1* | 4/2009 | Edwards | 128/204.23 |
| 2009/0107501 A1 | 4/2009 | Krieger | |
| 2009/0145428 A1* | 6/2009 | Sward et al. | 128/202.26 |
| 2009/0199855 A1 | 8/2009 | Davenport | |
| 2009/0211448 A1 | 8/2009 | McClain | |
| 2010/0051030 A1* | 3/2010 | Richard et al. | 128/204.23 |
| 2010/0071698 A1 | 3/2010 | Kiritake | |
| 2010/0094366 A1 | 4/2010 | McCarthy | |
| 2010/0116270 A1* | 5/2010 | Edwards et al. | 128/201.21 |
| 2010/0133900 A1* | 6/2010 | King | 307/9.1 |
| 2010/0282084 A1 | 11/2010 | Taylor et al. | |
| 2011/0017063 A1 | 1/2011 | Van Brunt et al. | |
| 2011/0017216 A1 | 1/2011 | Van Brunt et al. | |
| 2011/0020143 A1 | 1/2011 | Van Brunt et al. | |
| 2011/0020156 A1 | 1/2011 | Van Brunt et al. | |
| 2011/0030684 A1 | 2/2011 | Wilkinson et al. | |
| 2011/0030685 A1 | 2/2011 | Wilkinson et al. | |
| 2011/0030686 A1 | 2/2011 | Wilkinson et al. | |
| 2011/0030687 A1 | 2/2011 | Wilkinson et al. | |
| 2011/0030689 A1 | 2/2011 | Wilkinson et al. | |
| 2011/0247620 A1* | 10/2011 | Armstrong et al. | 128/204.23 |
| 2012/0055474 A1 | 3/2012 | Wilkinson et al. | |
| 2012/0055475 A1 | 3/2012 | Wilkinson et al. | |
| 2012/0055477 A1 | 3/2012 | Wilkinson et al. | |
| 2012/0055478 A1 | 3/2012 | Wilkinson et al. | |
| 2012/0055480 A1 | 3/2012 | Wilkinson et al. | |
| 2012/0055482 A1 | 3/2012 | Wilkinson et al. | |
| 2012/0055483 A1 | 3/2012 | Wilkinson et al. | |

FOREIGN PATENT DOCUMENTS

| | | |
|---|---|---|
| EP | 1661596 | 5/2006 |
| JP | 2007195820 | 8/2007 |
| KR | 10-0741307 | 7/2007 |
| WO | 99/22795 | 5/1999 |
| WO | 9943416 | 9/1999 |
| WO | 02/49742 | 6/2002 |
| WO | 20060108092 | 10/2006 |

OTHER PUBLICATIONS

Freesyle; FreeStyleTM Portable Oxygen Concentrator, Patient Manual, AirSep, Revision; Jan. 27, 2006; 36 pages.

Lifestyle; Lifestyle TM Portable Oxygen Concentrator, Patient Manual, AirSep, Revision Date Dec. 2004; 40 pages.

Search Report for PCT Application No. PCT/US2008/073884 issued on Mar. 10, 2009.

Written Opinion for PCT Application No. PCT/US2008/073884 issued on Mar. 10, 2009.

European Search Report for EP08798386.

International Preliminary Report on Patentability from PCTUS2008073884.

Living an Active Life with COPD, Lung Fact Sheets, European Lung Foundation.

Yang, Ralph T., "Gas Separation by Adsorption Processes", Imperial College Press, 1987, pp. 141-200. ;, 1987, pp. 141-200.

Hartzog, D. G. and Sircar, S., "Sensitivity of PSA Process Performance to Input Variables", Adsorption 1, 133-151 (1995). ;1, 133-151 (1995).

Keller II, George E., et al., "A New Process for Adsorption Separation of Gas Streams", ACS Symposium Series 135, 1980, pp. 275-286.

"Pressure Swing Adsorption" Douglas Morris Ruthven, Shamsuzzaman Farooq, and Kent S. Knaebel; VCH Publishers, 1994—Science.

Kopaygorodsky et al. "Scaling Analysis—A Valuable Technique in Engineering Teaching and Practice" Proceedings of the 2001 American Society for Engineering Education Annual Conference & Exposition Session 3513, 2001.

Tiep "Long-Term Home Oxygen Therapy", Clinics in Chest Medicine, Sep. 1990, vol. 11, No, 3, pp. 505-521.

Dietz "international Society for Mountain Medicine: An Altitude Tutorial" Jan. 29, 2006, pp. 1-2.

Kumar, R., et al., "A Versatile Process Simulator for Adsorptive Separations", Chemical Engineering Science, vol. 49, No. 18, pp. 3115-3125. ;, vol. 49, No. 18, pp. 3115-3125.

Search Report/Written Opinion for PCT Application No. PCT/US2011/050700 issued on May 1, 2012.

Office Action for U.S. Appl. No. 12/868,340 issued Oct. 10, 2012.
Office Action for U.S. Appl. No. 12/868,354 issued Oct. 11, 2012.
Office Action for U.S. Appl. No. 12/868,368 issued Oct. 5, 2012.
Office Action for U.S. Appl. No. 12/868,382 issued Oct. 12, 2012.
Office Action for U.S. Appl. No. 12/868,391 issued Oct. 5, 2012.
Office Action for U.S. Appl. No. 12/876,848 issued Oct. 26, 2012.
Office Action for U.S. Appl. No. 12/876,854 issued Nov. 28, 2012.
Office Action for U.S. Appl. No. 12/876,878 issued Nov. 9, 2012.
Office Action for U.S. Appl. No. 12/876,874 issued Aug. 22, 2012.
Office Action for U.S. Appl. No. 12/876,882 issued Dec. 6, 2012.
Office Action for U.S. Appl. No. 12/876,884 issued Nov. 13, 2012.
Office Action for U.S. Appl. No. 12/876,890 issued Nov. 26, 2012.
Office Action for U.S. Appl. No. 12/876,890 issued Dec. 21, 2012.

* cited by examiner

POWER MANAGEMENT SYSTEMS AND METHODS FOR USE IN AN OXYGEN CONCENTRATOR

BACKGROUND OF THE INVENTION

1. Field of the Invention

The present invention relates generally to health equipment and, more specifically, to oxygen concentrators.

2. Description of the Related Art

There are many patients that require supplemental oxygen as part of Long Term Oxygen Therapy, LTOT. Currently, the vast majority of patients that are receiving LTOT, are diagnosed under the general category of Chronic Obstructive Pulmonary Disease, COPD. This general diagnosis includes such common diseases as Chronic Asthma, Emphysema, Congestive Heart Failure and several other cardio-pulmonary conditions. Other people (e.g., obese individuals) may also require supplemental oxygen, for example, to maintain elevated activity levels.

Doctors may prescribe oxygen concentrators or portable tanks of medical oxygen for these patients. Usually a specific oxygen flow rate is prescribed (e.g., 1 liter per minute (LPM), 2 LPM, 3 LPM, etc.). Experts in this field have also recognized that exercise for these patients provide long term benefits that slow the progression of the disease, improve quality of life and extend patient longevity. Most stationary forms of exercise like tread mills and stationary bicycles, however, are too strenuous for these patients. As a result, the need for mobility has long been recognized. Until recently, this mobility has been facilitated by the use of small compressed oxygen tanks. The disadvantage of these tanks is that they have a finite amount of oxygen and they are heavy, weighing about 50 pounds, when mounted on a cart with dolly wheels.

Oxygen concentrators have been in use for about 50 years to supply patients suffering from respiratory insufficiency with supplemental oxygen. Traditional oxygen concentrators used to provide these flow rates have been bulky and heavy making ordinary ambulatory activities with them difficult and impractical. Recently, companies that manufacture large stationary home oxygen concentrators began developing portable oxygen concentrators, POCs. The advantage of POCs concentrators was that they can produce a theoretically endless supply of oxygen. In order to make these devices small for mobility, the various systems necessary for the production of oxygen enriched gas are condensed.

SUMMARY

In an embodiment, an oxygen concentrator apparatus, includes at least two canisters; gas separation adsorbent disposed in at least two canisters, wherein the gas separation adsorbent separates at least some nitrogen from air in the canister to produce oxygen enriched gas; and a compression system. The compression system includes a compressor coupled to at least one canister, wherein the compressor compresses air during operation; and a motor coupled to the compressor, wherein the motor comprises an external rotating armature that drives the operation of the compressor.

In an embodiment, an oxygen concentrator apparatus, includes at least two canisters; gas separation adsorbent disposed in at least two canisters, wherein the gas separation adsorbent separates at least some nitrogen from air in the canister to produce oxygen enriched gas; and a compression system. The compression system includes a compressor coupled to at least one canister, wherein the compressor compresses air during operation; and a motor coupled to the compressor that drives the operation of the compressor. The compression system further includes an air transfer device coupled to the motor, wherein the air transfer device creates an air flow when the motor is operated, wherein the created airflow passes over at least a portion of the motor.

In an embodiment, an oxygen concentrator apparatus includes at least two canisters; gas separation adsorbent disposed in at least two canisters, wherein the gas separation adsorbent separates at least some nitrogen from air in the canister to produce oxygen enriched gas; and a compression system coupled to at least one canister. The compression system includes a compressor outlet conduit coupling the compressor to at least one canister, wherein compressed air is transferred from the compressor to at least one canister through the compressor outlet conduit. The oxygen concentrator apparatus also includes at least one air transfer device, wherein the air transfer device creates an air flow during use, and wherein the air transfer device is positioned such that the created airflow passes over at least a portion of the compressor outlet conduit.

In an embodiment, an oxygen concentrator apparatus includes at least two canisters; gas separation adsorbent disposed in at least two canisters, wherein the gas separation adsorbent separates at least some nitrogen from air in the canister to produce oxygen enriched gas; and a compression system. The compression system includes a compressor coupled to at least one canister, wherein the compressor compresses air during operation; and a motor coupled to the compressor, wherein the motor drives the operation of the compressor. The oxygen concentrator apparatus also includes a compressor outlet conduit coupling the compressor to at least one canister, wherein compressed air is transferred from the compressor to at least one canister through the compressor outlet conduit. An outlet of one or more canisters is positioned such that gas exiting one or more canisters during a venting process is directed toward: at least a portion of the motor; at least a portion of the compressor; at least a portion of the compressor outlet conduit; or combinations thereof, during use.

In an embodiment, an oxygen concentrator apparatus includes at least two canisters; gas separation adsorbent disposed in at least two canisters, wherein the gas separation adsorbent separates at least some nitrogen from air in the canister to produce oxygen enriched gas; and a compression system. The compression system includes a compressor coupled to at least one canister, wherein the compressor compresses air during operation; and a motor coupled to the compressor, wherein the motor drives the operation of the compressor. The oxygen concentrator apparatus also includes a compressor outlet conduit coupling the compressor to at least one canister, wherein compressed air is transferred from the compressor to at least one canister through the compressor outlet conduit. At least a portion of the compressor outlet conduit is positioned proximate to at least a portion of the motor; and an outlet of one or more canisters is positioned such that gas exiting one or more canisters during a venting process is directed toward at least the portion of the compressor outlet conduit positioned proximate to the motor, and gas exiting one or more canisters during a venting process is directed toward at least a portion of the motor proximate to the compressor outlet conduit, during use.

In an embodiment, an oxygen concentrator apparatus includes at least two canisters; gas separation adsorbent disposed in at least two canisters, wherein the gas separation adsorbent separates at least some nitrogen from air in the canister to produce oxygen enriched gas; and a compression system. The compression system includes a compressor coupled to at least one canister, wherein the compressor compresses air during operation; and a motor coupled to the compressor, wherein the motor drives the operation of the compressor. The oxygen concentrator apparatus also includes a compressor outlet conduit coupling the compressor to at least one canister, wherein compressed air is transferred from the compressor to at least one canister through the compressor outlet conduit. An air transfer device is coupled to the motor, wherein the air transfer device creates an air flow when the motor is operated. At least a portion of the compressor outlet conduit is positioned proximate to at least a portion of the motor. An outlet of one or more canisters is positioned such that gas exiting one or more canisters during a venting process is directed toward at least the portion of the compressor outlet conduit positioned proximate to the motor, and gas exiting one or more canisters during a venting process is directed toward at least a portion of the motor proximate to the compressor outlet conduit, during use. The air transfer device facilitates flow of gas exiting the canister during the venting process.

In an embodiment, a method of providing an oxygen enriched gas to a user of an oxygen concentrator includes automatically assessing at least a portion of an inhalation profile of the user during use of the oxygen concentrator; providing oxygen enriched gas produced by the oxygen concentrator to the user, wherein the frequency and/or duration of the delivery of the oxygen enriched gas is at least partially based on the assessed inhalation profile; and adjusting the frequency and/or duration of the provided oxygen enriched gas based on one or more changes in the assessed inhalation profile.

In an embodiment, a method of providing an oxygen enriched gas to a user of an oxygen concentrator includes: automatically detecting user inhalations during use of the oxygen concentrator; automatically assessing a current breathing rate of the user based on detected user inhalations; providing oxygen enriched gas produced by the oxygen concentrator to the user from the oxygen concentrator, wherein the frequency and/or duration of the provided oxygen enriched gas is at least partially based on the automatically assessed breathing rate; and adjusting the frequency and/or duration of the provided oxygen enriched gas based on changes in the automatically assessed current breathing rate.

In an embodiment, a method of providing an oxygen enriched gas to a user of an oxygen concentrator includes: automatically assessing an inhalation air flow rate of the user based on detected inhalations of the user; providing oxygen enriched gas produced by the oxygen concentrator to the user from the oxygen concentrator, wherein the frequency and/or duration of the provided oxygen enriched gas is at least partially based on the automatically assessed inhalation flow rate; and adjusting the frequency and/or duration of the provided oxygen enriched gas based on changes in the automatically assessed inhalation flow rate.

In an embodiment, an oxygen concentrator includes at least two canisters; gas separation adsorbent disposed in at least two canisters, wherein the gas separation adsorbent separates at least some nitrogen from air in the canister to produce oxygen enriched gas; and a compression system coupled to at least one canister, wherein the compression system compresses air during operation. The oxygen concentrator also includes a pressure sensor capable of detecting an ambient pressure of the apparatus during use, wherein operation of the compression system is based, at least in part, on the pressure detected by the pressure sensor.

In an embodiment, a method of providing an oxygen enriched gas to a user of an oxygen concentrator includes: assessing an ambient pressure with the pressure sensor; operating the compression system to compress air, wherein the operation of the compression system is based, at least in part, on the assessed ambient pressure; directing the compressed air into one or more of the canisters, wherein nitrogen is separated from oxygen in one or more of the canisters to produce an oxygen enriched gas; and providing the oxygen enriched gas to the user.

In an embodiment, an oxygen concentrator system includes: at least two canisters; gas separation adsorbent disposed in at least two canisters, wherein the gas separation adsorbent separates at least some nitrogen from air in the canister to produce an oxygen enriched gas; a compression system coupled to at least one canister, wherein the compression system compresses air during operation. An internal power supply is coupled to the compression system, the internal power supply providing power to operate the compression system during use, the internal power supply including an internal power supply input port. An auxiliary power supply is removably connectable to the internal power supply input port. The auxiliary power supply includes one or more battery cells, an auxiliary power supply input port, and an auxiliary power supply output connector used to removably connect the auxiliary power supply to the internal power supply input port during use. The auxiliary power supply output connector is also removably connectable to the auxiliary power supply input port. An external charger is removable connectable to the internal power supply and the auxiliary power supply. The external charger includes an external charger output connector used to removably connect the external charger to the internal power supply input port and removable connect the external charger to the auxiliary power supply input port.

In an embodiment, an oxygen concentrator system includes: at least two canisters; gas separation adsorbent disposed in at least two canisters, wherein the gas separation adsorbent separates at least some nitrogen from air in the canister to produce an oxygen enriched gas; a compression system coupled to at least one canister, wherein the compression system compresses air during operation. An internal power supply is coupled to the compression system, the internal power supply providing power to operate at least the compression system during use. the internal power supply including an internal power supply input port. An auxiliary power supply is removably coupleable to the internal power supply input port. The auxiliary power supply includes: one or more battery cells; a control circuit coupled to one or more of the battery cells; an auxiliary power supply input port coupled to the control circuit; and an auxiliary power supply output connector coupled to the control circuit; wherein the auxiliary power supply output connector is used to removably couple the auxiliary power supply to the internal power supply input port during use. The control circuit directs flow of current through the auxiliary power supply during use.

In an embodiment, a method of providing continuous positive airway pressure to a user includes: supplying pressurized air from the compression system to a mask that has been coupled to a user's face; assessing an onset of inhalation of the user; and supplying oxygen enriched gas from the oxygen concentrator to the mask when the onset of inhalation of the user is detected.

In an embodiment, a method of providing continuous positive airway pressure to a user includes: supplying pressurized air from the compression system to a mask that has been coupled to a user's face; assessing an ambient pressure; assessing a pressure inside the mask while the pressurized air is supplied to the mask coupled to the user's face; assessing a correction pressure, wherein the correction pressure is a function of the ambient pressure and the assessed pressure inside the mask; automatically assessing a pressure inside the mask while the pressurized air is supplied to the mask coupled to the user's face; assessing an adjusted assessed pressure inside the mask as a function of the automatically assessed pressure and the correction pressure; supplying oxygen enriched gas from the oxygen concentrator to the mask if the adjusted assessed pressure inside the mask is less than a predetermined pressure.

In an embodiment, a method of providing continuous positive airway pressure to a user includes: supplying pressurized air from the compression system to a mask that has been coupled to a user's face, the mask comprising a venting port that allows gas to exit the mask; automatically assessing a flow rate of gas exiting the mask through the venting port; assessing a change in the flow rate of gas exiting the mask through the venting port; supplying oxygen enriched gas from the oxygen concentrator to the mask if the detected change in the flow rate indicates a decrease in the flow rate of gas exiting the mask.

In an embodiment, a method of providing continuous positive airway pressure to a user includes: coupling the oxygen concentrator to one or more of the conduits; supplying pressurized air from the compression system to a mask that has been coupled to a user's face; supplying oxygen enriched gas from the oxygen concentrator to one or more conduits.

In an embodiment, a method of positive pressure ventilation to a user includes: supplying pulses of pressurized breathing gas from the compressed gas system to a mask that has been coupled to a user's face; and supplying oxygen enriched gas from the oxygen concentrator to the mask.

In an embodiment, an oxygen concentrator system includes: at least two canisters; gas separation adsorbent disposed in at least two canisters, wherein the gas separation adsorbent separates at least some nitrogen from air in the canister to produce an oxygen enriched gas; and a compression system coupled to at least one canister, wherein the compression system compresses air during operation; at least one conduit coupled to at least one canister, the conduit receiving an oxygen enriched gas from at least one canister during use; and a mouthpiece, removably couplable to one or more teeth in a user's mouth, wherein the mouthpiece is coupled to at least one conduit, wherein an oxygen enriched gas is directed to the mouth of the user via the mouthpiece during use.

In an embodiment, a method of operating an oxygen concentrator apparatus includes: automatically pressurizing one or more canisters with oxygen enriched gas during a shutdown sequence of the oxygen concentrator such that the pressure inside one or more canisters is above ambient pressure.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
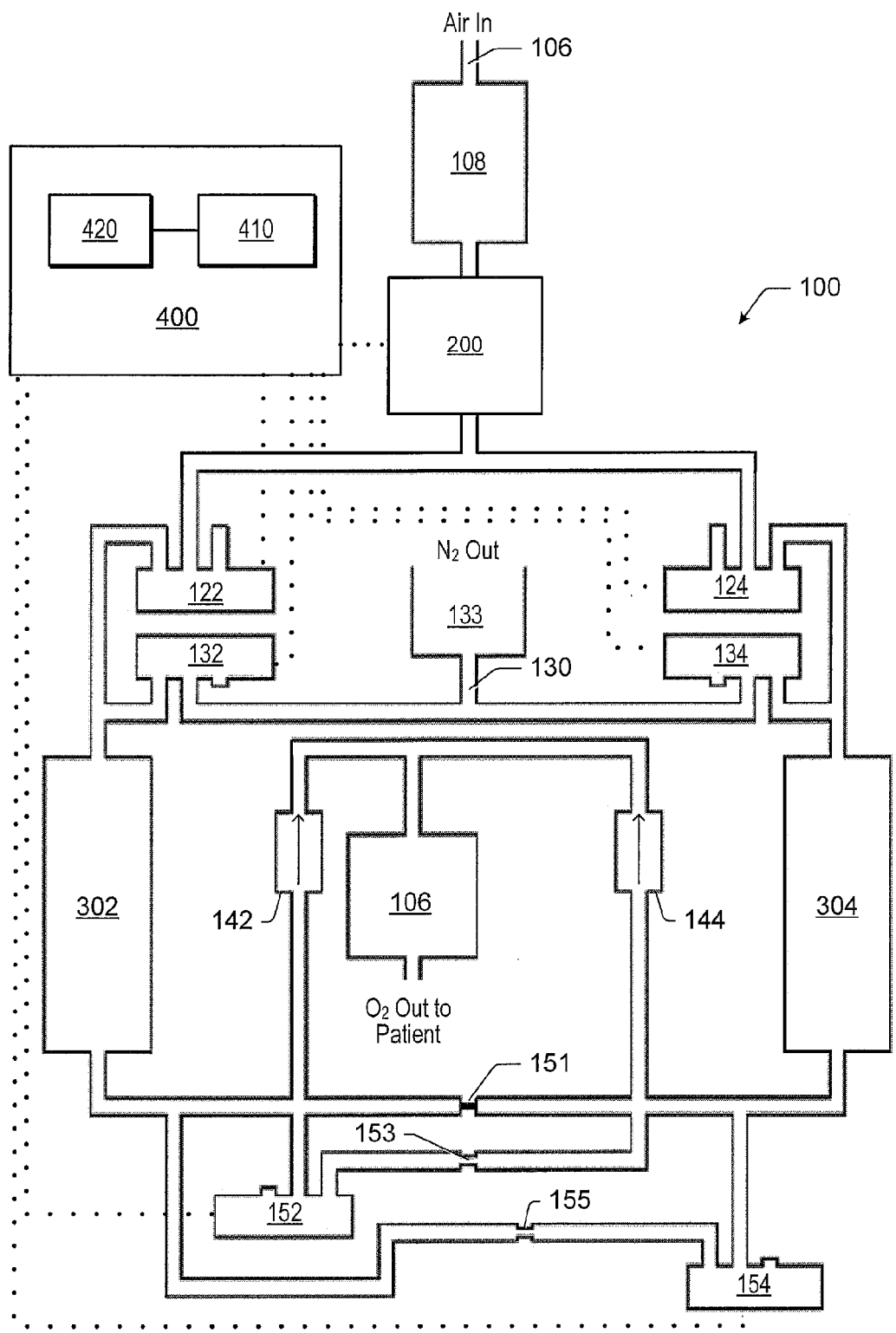
FIG. 1 depicts a schematic diagram of the components of an oxygen concentrator.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims.

DETAILED DESCRIPTION OF THE EMBODIMENTS

It is to be understood the present invention is not limited to particular devices or methods, which may, of course, vary. It is also to be understood that the terminology used herein is for the purpose of describing particular embodiments only, and is not intended to be limiting. Headings are for organizational purposes only and are not meant to be used to limit or interpret the description or claims. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to."

The term "coupled" as used herein means either a direct connection or an indirect connection (e.g., one or more intervening connections) between one or more objects or components. The phrase "connected" means a direct connection between objects or components such that the objects or components are connected directly to each other. As used herein the phrase "obtaining" a device means that the device is either purchased or constructed.

Oxygen concentrators take advantage of pressure swing adsorption (PSA). Pressure swing adsorption may involve using a compressor to increase gas pressure inside a canister that contains particles of a gas separation adsorbent. As the pressure increases, certain molecules in the gas may become adsorbed onto the gas separation adsorbent. Removal of a portion of the gas in the canister under the pressurized conditions allows separation of the non-adsorbed molecules from the adsorbed molecules. The gas separation adsorbent may be regenerated by reducing the pressure, which reverses the adsorption of molecules from the adsorbent. Further details regarding oxygen concentrators may be found, for example, in U.S. Published Patent Application No. 2009-0065007, published Mar. 12, 2009, and entitled "Oxygen Concentrator Apparatus and Method", which is incorporated herein by reference.

Ambient air usually includes approximately 78% nitrogen and 21% oxygen with the balance comprised of argon, carbon dioxide, water vapor and other trace elements. If a gas mixture such as air, for example, is passed under pressure through a vessel containing a gas separation adsorbent bed that attracts nitrogen more strongly than it does oxygen, part or all of the nitrogen will stay in the bed, and the gas coming out of the vessel will be enriched in oxygen. When the bed reaches the end of its capacity to adsorb nitrogen, it can be regenerated by reducing the pressure, thereby releasing the adsorbed nitrogen. It is then ready for another cycle of producing oxygen enriched air. By alternating canisters in a two-canister system, one canister can be collecting oxygen while the other canister is being purged (resulting in a continuous separation of the oxygen from the nitrogen). In this manner, oxygen can be accumulated out of the air for a variety of uses include providing supplemental oxygen to patients.

FIG. 1 illustrates a schematic diagram of an oxygen concentrator 100, according to an embodiment. Oxygen concentrator 100 may concentrate oxygen out of an air stream to provide oxygen enriched gas to a user. As used herein, "oxygen enriched gas" is composed of at least about 50% oxygen, at least about 60% oxygen, at least about 70% oxygen, at least about 80% oxygen, at least about 90% oxygen, at least about 95% oxygen, at least about 98% oxygen, or at least about 99% oxygen.

Oxygen concentrator 100 may be a portable oxygen concentrator. For example, oxygen concentrator 100 may have a weight and size that allows the oxygen concentrator to be carried by hand and/or in a carrying case. In one embodiment, oxygen concentrator 100 has a weight of less than about 20 lbs., less than about 15 lbs., less than about 10 lbs, or less than about 5 lbs. In an embodiment, oxygen concentrator 100 has a volume of less than about 1000 cubic inches, less than about 750 cubic inches; less than about 500 cubic inches, less than about 250 cubic inches, or less than about 200 cubic inches.

Oxygen may be collected from ambient air by pressurizing ambient air in canisters 302 and 304, which include a gas separation adsorbent. Gas separation adsorbents useful in an oxygen concentrator are capable of separating at least nitrogen from an air stream to produce oxygen enriched gas. Examples of gas separation adsorbents include molecular sieves that are capable of separation of nitrogen from an air stream. Examples of adsorbents that may be used in an oxygen concentrator include, but are not limited to, zeolites (natural) or synthetic crystalline aluminosilicates that separate nitrogen from oxygen in an air stream under elevated pressure. Examples of synthetic crystalline aluminosilicates that may be used include, but are not limited to: OXYSIV adsorbents available from UOP LLC, Des Plaines, IW; SYLOBEAD adsorbents available from W. R. Grace & Co, Columbia, Md.; SILIPORITE adsorbents available from CECA S.A. of Paris, France; ZEOCHEM adsorbents available from Zeochem AG, Uetikon, Switzerland; and AgLiLSX adsorbent available from Air Products and Chemicals, Inc., Allentown, Pa.

As shown in FIG. 1, air may enter the oxygen concentrator through air inlet 106. Air may be drawn into air inlet 106 by compression system 200. Compression system 200 may draw in air from the surroundings of the oxygen concentrator and compress the air, forcing the compressed air into one or both canisters 302 and 304. In an embodiment, an inlet muffler 108 may be coupled to air inlet 106 to reduce sound produced by air being pulled into the oxygen generator by compression system 200. In an embodiment, inlet muffler 108 may be a moisture and sound absorbing muffler. For example, a water absorbent material (such as a polymer water absorbent material or a zeolite material) may be used to both absorb water from the incoming air and to reduce the sound of the air passing into the air inlet 106.

Compression system 200 may include one or more compressors capable of compressing air. Pressurized air, produced by compression system 200, may be forced into one or both of the canisters 302 and 304. In some embodiments, the ambient air may be pressurized in the canisters to a pressure approximately in a range of 13-20 pounds per square inch (psi). Other pressures may also be used, depending on the type of gas separation adsorbent disposed in the canisters.

Coupled to each canister 302/304 are inlet valves 122/124 and outlet valves 132/134. As shown in FIG. 1, inlet valve 122 is coupled to canister 302 and inlet valve 124 is coupled to canister 304. Outlet valve 132 is coupled to canister 302 and outlet valve 134 is coupled to canister 304. Inlet valves 122/124 are used to control the passage of air from compression system 200 to the respective canisters. Outlet valves 132/134 are used to release gas from the respective canisters during a venting process. In some embodiments, inlet valves 122/124 and outlet valves 132/134 may be silicon plunger solenoid valves. Other types of valves, however, may be used. Plunger valves offer advantages over other kinds of valves by being quiet and having low slippage.

In some embodiments, a two-step valve actuation voltage may be used to control inlet valves 122/124 and outlet valves 132/134. For example, a high voltage (e.g., 24 V) may be applied to an inlet valve to open the inlet valve. The voltage may then be reduced (e.g., to 7 V) to keep the inlet valve open. Using less voltage to keep a valve open may use less power (Power=Voltage*Current). This reduction in voltage minimizes heat build up and power consumption to extend run time from the battery. When the power is cut off to the valve, it closes by spring action. In some embodiments, the voltage may be applied as a function of time that is not necessarily a stepped response (e.g., a curved downward voltage between an initial 24 V and a final 7 V).

In an embodiment, pressurized air is sent into one of canisters 302 or 304 while the other canister is being vented. For example, during use, inlet valve 122 is opened while inlet valve 124 is closed. Pressurized air from compression system 200 is forced into canister 302, while being inhibited from entering canister 304 by inlet valve 124. In an embodiment, a controller 400 is electrically coupled to valves 122, 124, 132, and 134. Controller 400 includes one or more processors 410 operable to execute program instructions stored in memory 420. The program instructions are operable to perform various predefined methods that are used to operate the oxygen concentrator. Controller 400 may include program instructions for operating inlet valves 122 and 124 out of phase with each other, i.e., when one of inlet valves 122 or 124 is opened, the other valve is closed. During pressurization of canister 302, outlet valve 132 is closed and outlet valve 134 is opened. Similar to the inlet valves, outlet valves 132 and 134 are operated out of phase with each other. In some embodiments, the voltages and the duration of the voltages used to open the input and output valves may be controlled by controller 400.

Check valves 142 and 144 are coupled to canisters 302 and 304, respectively. Check valves 142 and 144 are one way valves that are passively operated by the pressure differentials that occur as the canisters are pressurized and vented. Check valves 142 and 144 are coupled to canisters to allow oxygen produced during pressurization of the canister to flow out of the canister, and to inhibit back flow of oxygen or any other gases into the canister. In this manner, check valves 142 and 144 act as one way valves allowing oxygen enriched gas to exit the respective canister during pressurization.

The term "check valve", as used herein, refers to a valve that allows flow of a fluid (gas or liquid) in one direction and inhibits back flow of the fluid. Examples of check valves that are suitable for use include, but are not limited to: a ball check valve; a diaphragm check valve; a butterfly check valve; a swing check valve; a duckbill valve; and a lift check valve. Under pressure, nitrogen molecules in the pressurized ambient air are adsorbed by the gas separation adsorbent in the pressurized canister. As the pressure increases, more nitrogen is adsorbed until the gas in the canister is enriched in oxygen. The nonadsorbed gas molecules (mainly oxygen) flow out of the pressurized canister when the pressure reaches a point sufficient to overcome the resistance of the check valve coupled to the canister. In one embodiment, the pressure drop of the check valve in the forward direction is less than 1 psi. The break pressure in the reverse direction is greater than 100 psi. It should be understood, however, that modification of one or more components would alter the operating parameters of these valves. If the forward flow pressure is increased, there is, generally, a reduction in oxygen enriched gas production. If the break pressure for reverse flow is reduced or set too low, there is, generally, a reduction in oxygen enriched gas pressure.

In an exemplary embodiment, canister 302 is pressurized by compressed air produced in compression system 200 and passed into canister 302. During pressurization of canister 302 inlet valve 122 is open, outlet valve 132 is closed, inlet valve 124 is closed and outlet valve 134 is open. Outlet valve 134 is opened when outlet valve 132 is closed to allow substantially simultaneous venting of canister 304 while canister 302 is pressurized. Canister 302 is pressurized until the pressure in canister is sufficient to open check valve 142. Oxygen enriched gas produced in canister 302 exits through check valve and, in one embodiment, is collected in accumulator 106.

After some time the gas separation adsorbent will become saturated with nitrogen and will be unable to separate significant amounts of nitrogen from incoming air. This point is usually reached after a predetermined time of oxygen enriched gas production. In the embodiment described above, when the gas separation adsorbent in canister 302 reaches this saturation point, the inflow of compressed air is stopped and canister 302 is vented to remove nitrogen. During venting, inlet valve 122 is closed, and outlet valve 132 is opened. While canister 302 is being vented, canister 304 is pressurized to produce oxygen enriched gas in the same manner described above. Pressurization of canister 304 is achieved by closing outlet valve 134 and opening inlet valve 124. The oxygen enriched gas exits canister 304 through check valve 144.

During venting of canister 302, outlet valve 132 is opened allowing pressurized gas (mainly nitrogen) to exit the canister through concentrator outlet 130. In an embodiment, the vented gases may be directed through muffler 133 to reduce the noise produced by releasing the pressurized gas from the canister. As gas is released from canister 302, the pressure in the canister drops, allowing the nitrogen to become desorbed from the gas separation adsorbent. The released nitrogen exits the canister through outlet 130, resetting the canister to a state that allows renewed separation of oxygen from an air stream. Muffler 133 may include open cell foam (or another material) to muffle the sound of the gas leaving the oxygen concentrator. In some embodiments, the combined muffling components/techniques for the input of air and the output of gas, may provide for oxygen concentrator operation at a sound level below 50 decibels.

During venting of the canisters, it is advantageous that at least a majority of the nitrogen is removed. In an embodiment, at least about 50%, at least about 60%, at least about 70%, at least about 80%, at least about 90%, at least about 95%, at least about 98%, or substantially all of the nitrogen in a canister is removed before the canister is re-used to separate oxygen from air. In some embodiments, a canister may be further purged of nitrogen using an oxygen enriched stream that is introduced into the canister from the other canister.

In an exemplary embodiment, a portion of the oxygen enriched gas may be transferred from canister 302 to canister 304 when canister 304 is being vented of nitrogen. Transfer of oxygen enriched gas from canister 302 to 304, during venting of canister 304, helps to further purge nitrogen (and other gases) from the canister. In an embodiment, oxygen enriched gas may travel through flow restrictors 151, 153, and 155 between the two canisters. Flow restrictor 151 may be a trickle flow restrictor. Flow restrictor 151, for example, may be a 0.009 D flow restrictor (e.g., the flow restrictor has a radius 0.009" which is less than the diameter of the tube it is inside). Flow restrictors 153 and 155 may be 0.013 D flow restrictors. Other flow restrictor types and sizes are also contemplated and may be used depending on the specific configuration and tubing used to couple the canisters. In some embodiments, the flow restrictors may be press fit flow restrictors that restrict air flow by introducing a narrower diameter in their respective tube. In some embodiments, the press fit flow restrictors may be made of sapphire, metal or plastic (other materials are also contemplated).

Flow of oxygen enriched gas is also controlled by use of valve 152 and valve 154. Valves 152 and 154 may be opened for a short duration during the venting process (and may be closed otherwise) to prevent excessive oxygen loss out of the purging canister. Other durations are also contemplated. In an exemplary embodiment, canister 302 is being vented and it is desirable to purge canister 302 by passing a portion of the oxygen enriched gas being produced in canister 304 into canister 302. A portion of oxygen enriched gas, upon pressurization of canister 304, will pass through flow restrictor 151 into canister 302 during venting of canister 302. Additional oxygen enriched air is passed into canister 302, from canister 304, through valve 154 and flow restrictor 155. Valve 152 may remain closed during the transfer process, or may be opened if additional oxygen enriched gas is needed. The selection of appropriate flow restrictors 151 and 155, coupled with controlled opening of valve 154 allows a controlled amount of oxygen enriched gas to be sent from canister 304 to 302. In an embodiment, the controlled amount of oxygen enriched gas is an amount sufficient to purge canister 302 and minimize the loss of oxygen enriched gas through venting valve 132 of canister 302. While this embodiment describes venting of canister 302, it should be understood that the same process can be used to vent canister 304 using flow restrictor 151, valve 152 and flow restrictor 153.

The pair of equalization/vent valves 152/154 work with flow restrictors 153 and 155 to optimize the air flow balance between the two canisters. This may allow for better flow control for venting the canisters with oxygen enriched gas from the other of the canisters. It may also provide better flow direction between the two canisters. It has been found that, while flow valves 152/154 may be operated as bi-directional valves, the flow rate through such valves varies depending on the direction of fluid flowing through the valve. For example, oxygen enriched gas flowing from canister 304 toward canister 302 has a flow rate faster through valve 152 than the flow rate of oxygen enriched gas flowing from canister 302 toward canister 304 through valve 152. If a single valve was to be used, eventually either too much or too little oxygen enriched gas would be sent between the canisters and the canisters would, over time, begin to produce different amounts of oxygen enriched gas. Use of opposing valves and flow restrictors on parallel air pathways may equalize the flow pattern of the oxygen between the two canisters. Equalizing the flow may allow for a steady amount of oxygen available to the user over multiple cycles and also may allow a predictable volume of oxygen to purge the other of the canisters. In some embodiments, the air pathway may not have restrictors but may instead have a valve with a built in resistance or the air pathway itself may have a narrow radius to provide resistance.

At times, oxygen concentrator may be shutdown for a period of time. When an oxygen concentrator is shut down, the temperature inside the canisters may drop as a result of the loss of adiabatic heat from the compression system. As the temperature drops, the volume occupied by the gases inside the canisters will drop. Cooling of the canisters may lead to a negative pressure in the canisters. Valves (e.g., valves 122, 124, 132, and 134) leading to and from the canisters are dynamically sealed rather than hermetically sealed. Thus, outside air may enter the canisters after shutdown to accommodate the pressure differential. When outside air enters the canisters, moisture from the outside air may condense inside the canister as the air cools. Condensation of water inside the canisters may lead to gradual degradation of the gas separation adsorbents, steadily reducing ability of the gas separation adsorbents to produce oxygen enriched gas.

In an embodiment, outside air may be inhibited from entering canisters after the oxygen concentrator is shutdown by pressurizing both canisters prior to shutdown. By storing the canisters under a positive pressure, the valves may be forced into a hermetically closed position by the internal pressure of the air in the canisters. In an embodiment, the pressure in the canisters, at shutdown, should be at least greater than ambient pressure. As used herein the term "ambient pressure" refers to the pressure of the surroundings that the oxygen generator is located (e.g. the pressure inside a room, outside, in a plane, etc.). In an embodiment, the pressure in the canisters, at shutdown, is at least greater than standard atmospheric pressure (i.e., greater than 760 mmHg (Torr), 1 atm, 101,325 Pa). In an embodiment, the pressure in the canisters, at shutdown, is at least about 1.1 times greater than ambient pressure; is at least about 1.5 times greater than ambient pressure; or is at least about 2 times greater than ambient pressure.

In an embodiment, pressurization of the canisters may be achieved by directing pressurized air into each canister from the compression system and closing all valves to trap the pressurized air in the canisters. In an exemplary embodiment, when a shutdown sequence is initiated, inlet valves 122 and 124 are opened and outlet valves 132 and 134 are closed. Because inlet valves 122 and 124 are joined together by a common conduit, both canisters 302 and 304 may become pressurized as air and or oxygen enriched gas from one canister may be transferred to the other canister. This situation may occur when the pathway between the compression system and the two inlet valves allows such transfer. Because the oxygen generator operates in an alternating pressurize/venting mode, at least one of the canisters should be in a pressurized state at any given time. In an alternate embodiment, the pressure may be increased in each canister by operation of compression system 200. When inlet valves 122 and 124 are opened, pressure between canisters 302 and 304 will equalize, however, the equalized pressure in either canister may not be sufficient to inhibit air from entering the canisters during shutdown. In order to ensure that air is inhibited from entering the canisters, compression system 200 may be operated for a time sufficient to increase the pressure inside both canisters to a level at least greater than ambient pressure. Regardless of the method of pressurization of the canisters, once the canisters are pressurized, inlet valves 122 and 124 are closed, trapping the pressurized air inside the canisters, which inhibits air from entering the canisters during the shutdown period.

Figure 2:
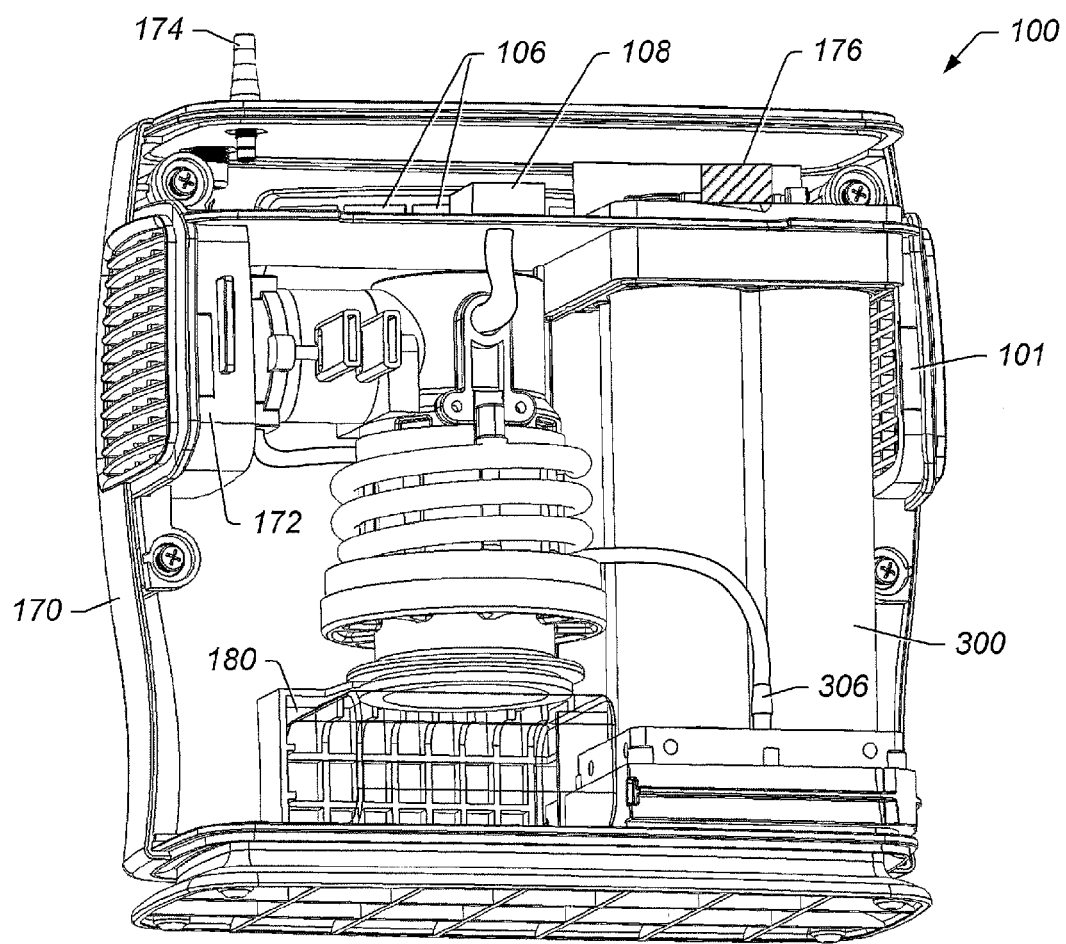
FIG. 2 depicts a side view of the main components of an oxygen concentrator.

Referring to FIG. 2, an embodiment of an oxygen concentrator 100 is depicted. Oxygen concentrator 100 includes a compression system 200, a canister assembly 300, and a power supply 180 disposed within an outer housing 170. Inlets 101 are located in outer housing 170 to allow air from the environment to enter oxygen concentrator 100. Inlets 101 may allow air to flow into the compartment to assist with cooling of the components in the compartment. Power supply 180 provides a source of power for the oxygen concentrator 100. Compression system 200 draws air in through the inlet 106 and muffler 108. Muffler 108 may reduce noise of air being drawn in by the compression system and also may include a desiccant material to remove water from the incoming air. Oxygen concentrator 100 may further include fan 172 used to vent air and other gases from the oxygen concentrator.

Compression System

Figure 3A:
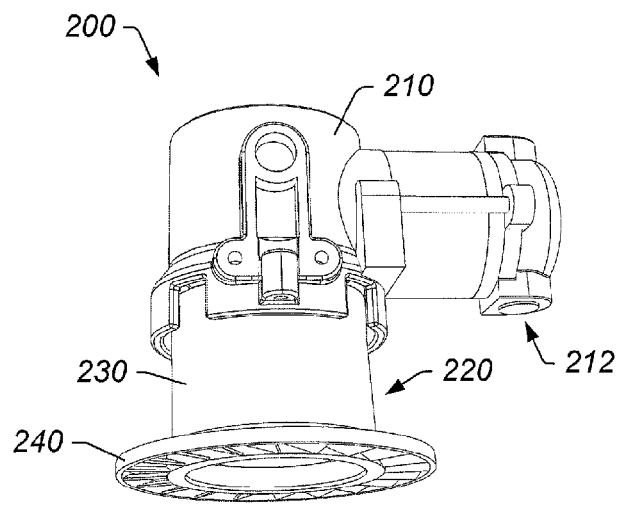
FIG. 3A depicts a perspective side view of a compression system.
Figure 3B:
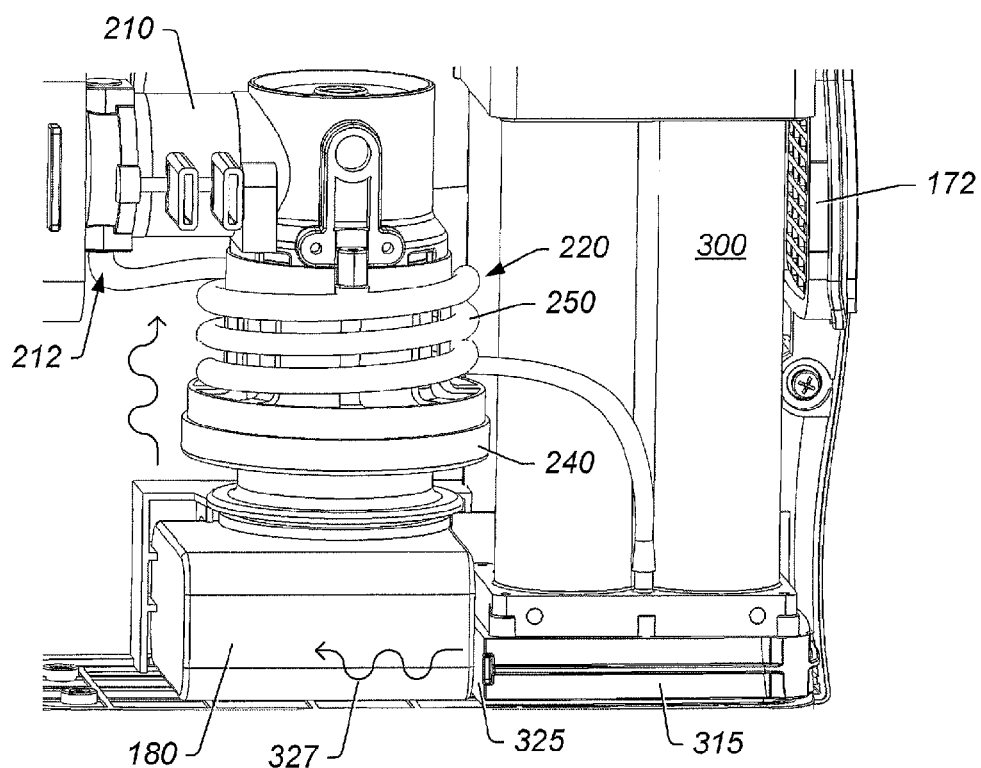
FIG. 3B depicts a side view of a compression system that includes a heat exchange conduit.

In some embodiments, compression system 200 includes one or more compressors. In another embodiment, compression system 200 includes a single compressor, coupled to all of the canisters of canister system 300. Turning to FIGS. 3A and 3B, a compression system 200 is depicted that includes compressor 210 and motor 220. Motor 220 is coupled to compressor 210 and provides an operating force to the compressor to operate the compression mechanism. For example, motor 220 may be a motor providing a rotating component that causes cyclical motion of a component of the compressor that compresses air. When compressor 210 is a piston type compressor, motor 220 provides an operating force which causes the piston of compressor 210 to be reciprocated. Reciprocation of the piston causes compressed air to be produced by compressor 210. The pressure of the compressed air is, in part, assessed by the speed that the compressor is operated at, (e.g., how fast the piston is reciprocated). Motor 220, therefore, may be a variable speed motor that is operable at various speeds to dynamically control the pressure of air produced by compressor 210.

In one embodiment, compressor 210 includes a single head wobble type compressor having a piston. Other types of compressors may be used such as diaphragm compressors and other types of piston compressors. Motor 220 may be a DC or AC motor and provides the operating power to the compressing component of compressor 210. Motor 220, in an embodiment, may be a brushless DC motor. Motor 220 may be a variable speed motor capable of operating the compressing component of compressor 210 at variable speeds. Motor 220 may be coupled to controller 400, as depicted in FIG. 1, which sends operating signals to the motor to control the operation of the motor. For example controller 400 may send signals to motor 220 to: turn the motor on, turn motor the off, and set the operating speed of motor.

Compression system 200 inherently creates substantial heat. Heat is caused by the consumption of power by motor 220 and the conversion of power into mechanical motion. Compressor 210 generates heat due to the increased resistance to movement of the compressor components by the air being compressed. Heat is also inherently generated due to adiabatic compression of the air by compressor 210. Thus the continual pressurization of air produces heat in the enclosure. Additionally, power supply 180 may produce heat as power is supplied to compression system 200. Furthermore, users of the oxygen concentrator may operate the device in unconditioned environments (e.g., outdoors) at potentially higher ambient temperatures than indoors, thus the incoming air will already be in a heated state.

Heat produced inside oxygen generator 100 can be problematic. Lithium ion batteries are generally employed as a power source for oxygen generators due to their long life and light weight. Lithium ion battery packs, however, are dangerous at elevated temperatures and safety controls are employed in oxygen concentrator 100 to shutdown the system if dangerously high power supply temperatures are detected. Additionally, as the internal temperature of oxygen concentrator 100 increases, the amount of oxygen generated by the concentrator may decrease. This is due, in part, to the decreasing amount of oxygen in a given volume of air at higher temperatures. If the amount of produced oxygen drops below a predetermined amount, the oxygen concentrator system may automatically shut down.

Because of the compact nature of oxygen concentrators, dissipation of heat can be difficult. Solutions typically involve the use of one or more fans to create a flow of cooling air through the enclosure. Such solutions, however, require additional power from the power supply and thus shorten the portable usage time of the oxygen concentrator. In an embodiment, a passive cooling system may be used that takes advantage of the mechanical power produced by motor 210. Referring to FIGS. 3A and 3B, compression system 200 includes motor 220 having an external rotating armature 230. Specifically, armature 230 of motor 220 (e.g. a DC motor) is wrapped around the stationary field that is driving the armature. Since motor 220 is a large contributor of heat to the overall system it is helpful to pull heat off of the motor and sweep it out of the enclosure. With the external high speed rotation, the relative velocity of the major component of the motor and the air in which it exists is very high. The surface area of the armature is larger if externally mounted than if it is internally mounted. Since the rate of heat exchange is proportional to the surface area and the square of the velocity, using a larger surface area armature mounted externally increases the ability of heat to be dissipated from motor 220. The gain in cooling efficiency by mounting the armature externally, allows the elimination of one or more cooling fans, thus reducing the weight and power consumption while maintaining the interior of the oxygen concentrator within the appropriate temperature range. Additionally, the rotation of the externally mounted armature creates movement of air proximate to the motor to create additional cooling.

Moreover, an external rotating armature may help the efficiency of the motor, allowing less heat to be generated. A motor having an external armature operates similar to the way a flywheel works in an internal combustion engine. When the motor is driving the compressor, the resistance to rotation is low at low pressures. When the pressure of the compressed air is higher, the resistance to rotation of the motor is higher. As a result, the motor does not maintain consistent ideal rotational stability, but instead surges and slows down depending on the pressure demands of the compressor. This tendency of the motor to surge and then slow down is inefficient and therefore generates heat. Use of an external armature adds greater angular momentum to the motor which helps to compensate for the variable resistance experienced by the motor. Since the motor does not have to work as hard, the heat produced by the motor may be reduced.

In an embodiment, cooling efficiency may be further increased by coupling an air transfer device 240 to external rotating armature 230. In an embodiment, air transfer device 240 is coupled to the external armature 230 such that rotation of the external armature causes the air transfer device to create an airflow that passes over at least a portion of the motor. In an embodiment, air transfer device includes one or more fan blades coupled to the armature. In an embodiment, a plurality of fan blades may be arranged in an annular ring such that the air transfer device acts as an impeller that is rotated by movement of the external rotating armature. As depicted in FIGS. 3A and 3B, air transfer device 240 may be mounted to an outer surface of the external armature 230, in alignment with the motor. The mounting of the air transfer device to the armature allows airflow to be directed toward the main portion of the external rotating armature, providing a cooling effect during use. In an embodiment, the air transfer device directs air flow such that a majority of the external rotating armature is in the air flow path.

Further, referring to FIGS. 3A and 3B, air pressurized by compressor 210 exits compressor 210 at compressor outlet 212. A compressor outlet conduit 250 is coupled to compressor outlet 212 to transfer the compressed air to canister system 300. As noted previously, compression of air causes an increase in the temperature of the air. This increase in temperature can be detrimental to the efficiency of the oxygen generator. In order to reduce the temperature of the pressurized air, compressor outlet conduit 250 is placed in the air flow path produced by air transfer device 240. At least a portion of compressor outlet conduit 250 may be positioned proximate to motor 220. Thus, airflow, created by air transfer device, may contact both motor 220 and compressor outlet conduit 250. In one embodiment, a majority of compressor outlet conduit 250 is positioned proximate to motor 220. In an embodiment, the compressor outlet conduit 250 is coiled around motor 220, as depicted in FIG. 3B.

In an embodiment, the compressor outlet conduit 250 is composed of a heat exchange metal. Heat exchange metals include, but are not limited to, aluminum, carbon steel, stainless steel, titanium, copper, copper-nickel alloys or other alloys formed from combinations of these metals. Thus, compressor outlet conduit 250 can act as a heat exchanger to remove heat that is inherently caused by compression of the air. By removing heat from the compressed air, the number of oxygen molecules in a given volume is increased. As a result, the amount of oxygen that can be generated by each canister during each pressuring swing cycle may be increased.

The heat dissipation mechanisms described herein are either passive or make use of elements required for the oxygen concentrator system. Thus, for example, dissipation of heat may be increased without using systems that require additional power. By not requiring additional power, the runtime of the battery packs may be increased and the size and weight of the oxygen concentrator may be minimized Likewise, use of an additional box fan or cooling unit may be eliminated. Eliminating such additional features reduces the weight and power consumption of the oxygen concentrator.

As discussed above, adiabatic compression of air causes the air temperature to increase. During venting of a canister in canister system 300, the pressure of the gas being released from the canisters decreases. The adiabatic decompression of the gas in the canister causes the temperature of the gas to drop as it is vented. In an embodiment, the cooled vented gases from canister system 300 are directed toward power supply 180 and toward compression system 200. In an embodiment, base 315 of compression system 300 receives the vented gases from the canisters. The vented gases 327 are directed through base 315 toward outlet 325 of the base and toward power supply 180. The vented gases, as noted, are cooled due to decompression of the gases and therefore passively provide cooling to the power supply. When the compression system is operated, the air transfer device will gather the cooled vented gases and direct the gases toward the motor of compression system 200. Fan 172 may also assist in directing the vented gas across compression system 200 and out of the enclosure 170. In this manner, additional cooling may be obtained without requiring any further power requirements from the battery.

Outlet System

An outlet system, coupled to one or more of the canisters, includes one or more conduits for providing oxygen enriched gas to a user. In an embodiment, oxygen enriched gas produced in either of canisters 302 and 304 is collected in accumulator 106 through check valves 142 and 144, respectively, as depicted schematically in FIG. 1. The oxygen enriched gas leaving the canisters may be collected in an oxygen accumulator 106 prior to being provided to a user. In some embodiments, a tube may be coupled to the accumulator 106 to provide the oxygen enriched gas to the user. Oxygen enriched gas may be provided to the user through an airway delivery device that transfer the oxygen enriched gas to the user's mouth and/or nose. In an embodiment, an outlet may include a tube that directs the oxygen toward a user's nose and/or mouth that may not be directly coupled to the user's nose.

Figure 4A:
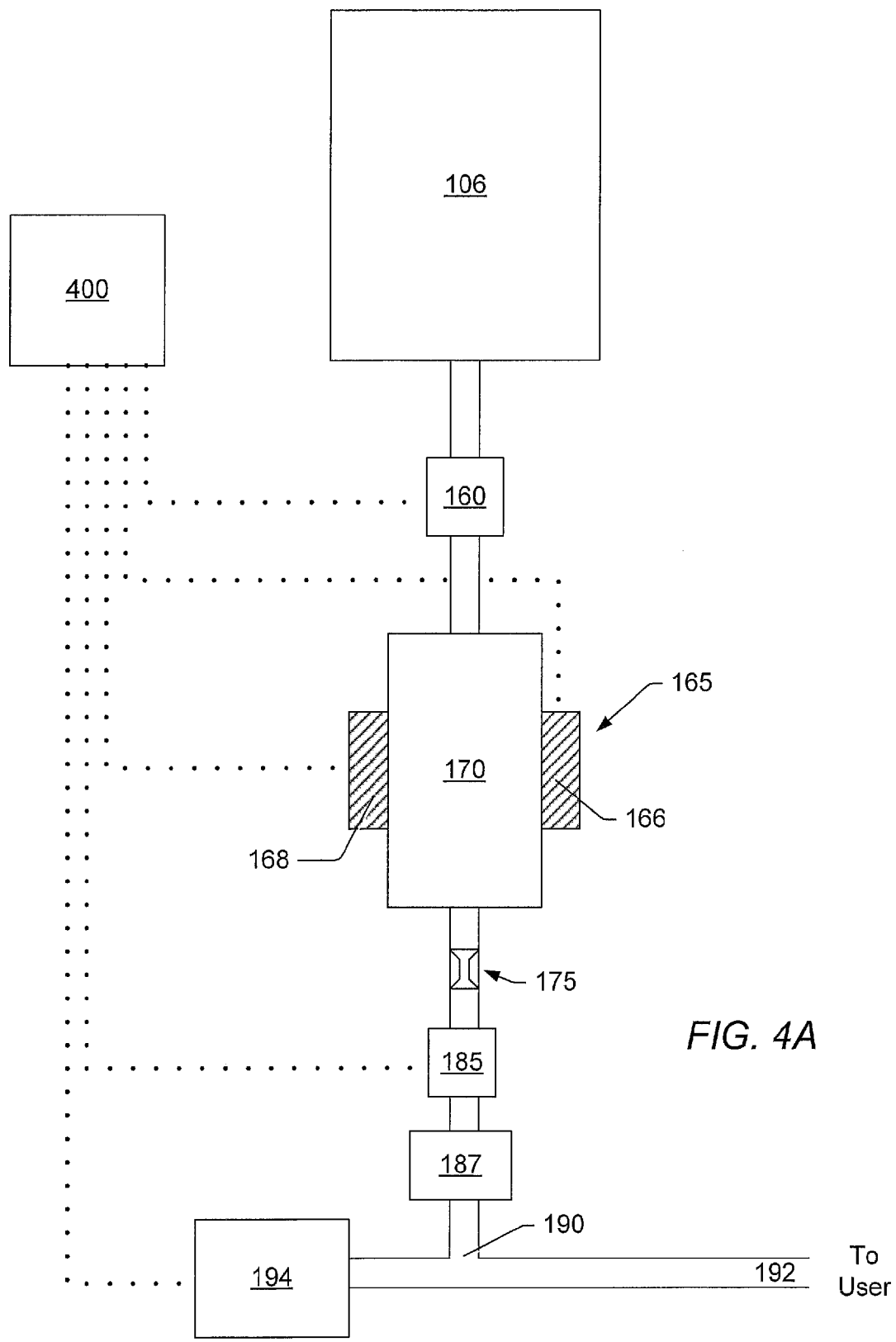
FIG. 4A depicts a schematic diagram of the outlet components of an oxygen concentrator.

Turning to FIG. 4A, a schematic diagram of an embodiment of an outlet system for an oxygen concentrator is shown. A supply valve 160 may be coupled to outlet tube to control the release of the oxygen enriched gas from accumulator 106 to the user. In an embodiment, supply valve 160 is an electromagnetically actuated plunger valve. Supply valve 160 is actuated by controller 400 to control the delivery of oxygen enriched gas to a user. Actuation of supply valve 160 is not timed or synchronized to the pressure swing adsorption process. Instead, actuation is, in some embodiments, synchronized to the patient's breathing. Additionally, supply valve 160 may have multiple actuations to help establish a clinically effective flow profile for providing oxygen enriched gas.

Oxygen enriched gas in accumulator 106 passes through supply valve 160 into expansion chamber 170 as depicted in FIG. 4A. In an embodiment, expansion chamber may include one or more devices capable of being used to determine an oxygen concentration of gas passing through the chamber. Oxygen enriched gas in expansion chamber 170 builds briefly, through release of gas from accumulator by supply valve 160, and then is bled through a small orifice flow restrictor 175 to a flow rate sensor 185 and then to particulate filter 187. Flow restrictor 175 may be a 0.025 D flow restrictor. Other flow restrictor types and sizes may be used. In some embodiments, the diameter of the air pathway in the housing may be restricted to create restricted air flow. Flow rate sensor 185 may be any sensor capable of assessing the rate of gas flowing through the conduit. Particulate filter 187 may be used to filter bacteria, dust, granule particles, etc prior to delivery of the oxygen enriched gas to the user. The oxygen enriched gas passes through filter 187 to connector 190 which sends the oxygen enriched gas to the user via conduit 192 and to pressure sensor 194.

The fluid dynamics of the outlet pathway, coupled with the programmed actuations of supply valve 160, results in a bolus of oxygen being provided at the correct time and with a flow profile that assures rapid delivery into the patient's lungs without any excessive flow rates that would result in wasted retrograde flow out the nostrils and into the atmosphere. It has been found, in our specific system, that the total volume of the bolus required for prescriptions is equal to 11 mL for each LPM, i.e., 11 mL for a prescription of 1 LPM; 22 mL for a prescription of 2 LPM; 33 mL for a prescription of 3 LPM; 44 mL for a prescription of 4 LPM; 55 mL for a prescription of 5 LPM; etc. This is generally referred to as the LPM equivalent. It should be understood that the LPM equivalent may vary between apparatus due to differences in construction design, tubing size, chamber size, etc.

Expansion chamber 170 may include one or more oxygen sensors capable of being used to determine an oxygen concentration of gas passing through the chamber. In an embodiment, the oxygen concentration of gas passing through expansion chamber 170 is assessed using an oxygen sensor 165. An oxygen sensor is a device capable of detecting oxygen in a gas. Examples of oxygen sensors include, but are not limited to, ultrasonic oxygen sensors, electrical oxygen sensors, and optical oxygen sensors. In one embodiment, oxygen sensor 165 is an ultrasonic oxygen sensor that includes an ultrasonic emitter 166 and an ultrasonic receiver 168. In some embodiments, ultrasonic emitter 166 may include multiple ultrasonic emitters and ultrasonic receiver 168 may include multiple ultrasonic receivers. In embodiments having multiple emitters/receivers, the multiple ultrasonic emitters and multiple ultrasonic receivers may be axially aligned (e.g., across the gas mixture flow path which may be perpendicular to the axial alignment).

In use, an ultrasonic sound wave (from emitter 166) may be directed through oxygen enriched gas disposed in chamber 170 to receiver 168. Ultrasonic sensor assembly may be based on detecting the speed of sound through the gas mixture to determine the composition of the gas mixture (e.g., the speed of sound is different in nitrogen and oxygen). In a mixture of the two gases, the speed of sound through the mixture may be an intermediate value proportional to the relative amounts of each gas in the mixture. In use, the sound at the receiver 168 is slightly out of phase with the sound sent from emitter 166. This phase shift is due to the relatively slow velocity of sound through a gas medium as compared with the relatively fast speed of the electronic pulse through wire. The phase shift, then, is proportional to the distance between the emitter and the receiver and the speed of sound through the expansion chamber. The density of the gas in the chamber affects the speed of sound through the chamber and the density is proportional to the ratio of oxygen to nitrogen in the chamber.

Therefore, the phase shift can be used to measure the concentration of oxygen in the expansion chamber. In this manner the relative concentration of oxygen in the accumulation chamber may be assessed as a function of one or more properties of a detected sound wave traveling through the accumulation chamber.

In some embodiments, multiple emitters 166 and receivers 168 may be used. The readings from the emitters 166 and receivers 168 may be averaged to cancel errors that may be inherent in turbulent flow systems. In some embodiments, the presence of other gases may also be detected by measuring the transit time and comparing the measured transit time to predetermined transit times for other gases and/or mixtures of gases.

The sensitivity of the ultrasonic sensor system may be increased by increasing the distance between the emitter 166 and receiver 168, for example to allow several sound wave cycles to occur between emitter 166 and the receiver 168. In some embodiments, if at least two sound cycles are present, the influence of structural changes of the transducer may be reduced by measuring the phase shift relative to a fixed reference at two points in time. If the earlier phase shift is subtracted from the later phase shift, the shift caused by thermal expansion of expansion chamber 170 may be reduced or cancelled. The shift caused by a change of the distance between the emitter 166 and receiver 168 may be the approximately the same at the measuring intervals, whereas a change owing to a change in oxygen concentration may be cumulative. In some embodiments, the shift measured at a later time may be multiplied by the number of intervening cycles and compared to the shift between two adjacent cycles. Further details regarding sensing of oxygen in the expansion chamber may be found, for example, in U.S. Published Patent Application No. 2009-0065007, published Mar. 12, 2009, and entitled "Oxygen Concentrator Apparatus and Method, which is incorporated herein by reference.

Flow rate sensor 185 may be used to determine the flow rate of gas flowing through the outlet system. Flow rate sensor that may be used include, but are not limited to: diaphragm/bellows flow meters; rotary flow meters (e.g. a hall effect flow meters); turbine flow meters; orifice flow meters; and ultrasonic flow meters. Flow rate sensor 185 may be coupled to controller 400. The rate of gas flowing through the outlet system may be an indication of the breathing volume of the user. Changes in the flow rate of gas flowing through the outlet system may also be used to determine a breathing rate of the user. Controller 400 may control actuation of supply valve 160 based on the breathing rate and/or breathing volume of the user, as assessed by flow rate sensor 185

In some embodiments, ultrasonic sensor system 165 and, for example, flow rate sensor 185 may provide a measurement of an actual amount of oxygen being provided. For example, follow rate sensor 185 may measure a volume of gas (based on flow rate) provided and ultrasonic sensor system 165 may provide the concentration of oxygen of the gas provided. These two measurements together may be used by controller 400 to determine an approximation of the actual amount of oxygen provided to the user.

Oxygen enriched gas passes through flow meter 185 to filter 187. Filter 187 removes bacteria, dust, granule particles, etc prior to providing the oxygen enriched gas to the user. The filtered oxygen enriched gas passes through filter 187 to connector 190. Connector 190 may be a "Y" connector coupling the outlet of filter 187 to pressure sensor 194 and outlet conduit 192. Pressure sensor 194 may be used to monitor the pressure of the gas passing through conduit 192 to the user. Changes in pressure, sensed by pressure sensor 194, may be used to determine a breathing rate of a user, as well as the onset of inhalation. Controller 400 may control actuation of supply valve 160 based on the breathing rate and/or onset of inhalation of the user, as assessed by pressure sensor 194. In an embodiment, controller 400 may control actuation of supply valve 160 based on information provided by flow rate sensor 185 and pressure sensor 194.

Figure 4B:
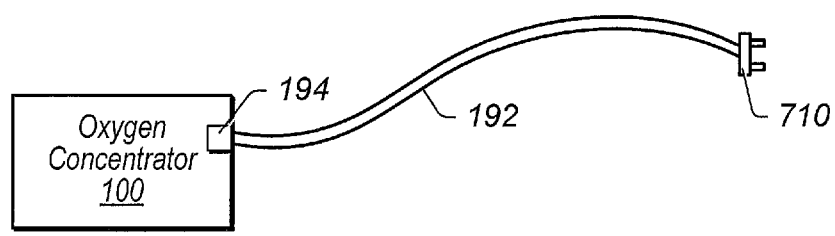
FIG. 4B depicts an outlet conduit for an oxygen concentrator.
Figure 4C:
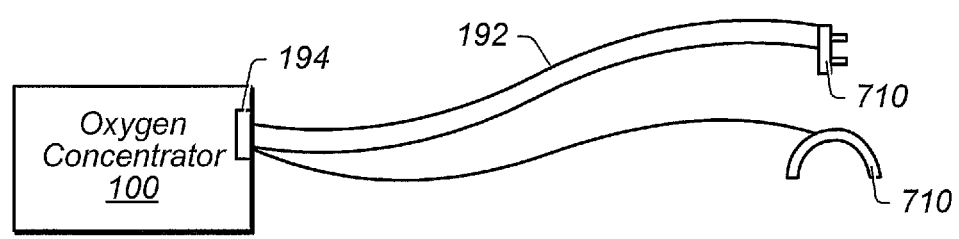
FIG. 4C depicts an alternate outlet conduit for an oxygen concentrator.

Oxygen enriched gas may be provided to a user through conduit 192. In an embodiment, conduit 192 may be a silicone tube. Conduit 192 may be coupled to a user using an airway coupling member 710, as depicted in FIGS. 4B and 4C. Airway delivery device 710 may be any device capable of providing the oxygen enriched gas to nasal cavities or oral cavities. Examples of airway coupling members include, but are not limited to: nasal masks, nasal pillows, nasal prongs, nasal cannulas, and mouthpieces. A nasal cannula airway delivery device is depicted in FIG. 4B. During use, oxygen enriched gas from oxygen concentrator system 100 is provided to the user through conduit 192 and airway coupling member 710. Airway delivery device 710 is positioned proximate to a user's airway (e.g., proximate to the user's mouth and or nose) to allow delivery of the oxygen enriched gas to the user while allowing the user to breath air from the surroundings.

In an alternate embodiment, a mouthpiece may be used to provide oxygen enriched gas to the user. As shown in FIG. 4C, a mouthpiece 720 may be coupled to oxygen concentrator system 100. Mouthpiece 720 may be the only device used to provide oxygen enriched gas to the user, or a mouthpiece may be used in combination with a nasal delivery device (e.g., a nasal cannula). As depicted in FIG. 4C, oxygen enriched gas may be provided to a user through both a nasal coupling member 720 and a mouthpiece 720.

Mouthpiece 720 is removably positionable in a user's mouth. In one embodiment, mouthpiece 720 is removably couplable to one or more teeth in a user's mouth. During use, oxygen enriched gas is directed into the user's mouth via the mouthpiece. Mouthpiece 720 may be a night guard mouthpiece which is molded to conform to the user's teeth. Alternatively, mouthpiece may be a mandibular repositioning device. In an embodiment, at least a majority of the mouthpiece is positioned in a user's mouth during use.

During use, oxygen enriched gas may be directed to mouthpiece 720 when a change in pressure is detected proximate to the mouthpiece. In one embodiment, mouthpiece 720 may be coupled to a pressure sensor. When a user inhales air through the user's mouth, pressure sensor may detect a drop in pressure proximate to the mouthpiece. Controller 400 of oxygen concentrator system 100 may provide a bolus of oxygen enriched gas to the user at the onset of the detection of inhalation.

During typical breathing of an individual, inhalation may occur through the nose, through the mouth or through both the nose and the mouth. Furthermore, breathing may change from one passageway to another depending on a variety of factors. For example, during more active activities, a user may switch from breathing through their nose to breathing through their mouth, or breathing through their mouth and nose. A system that relies on a single mode of delivery (either nasal or oral), may not function properly if breathing through the monitored pathway is stopped. For example, if a nasal cannula is used to provide oxygen enriched gas to the user, an inhalation sensor (e.g., a pressure sensor or flow rate sensor) is coupled to the nasal cannula to determine the onset of inhalation. If the user stops breathing through their nose, and switches to breathing through their mouth, the oxygen concentrator system may not know when to provide the oxygen enriched gas since there is no feedback from the nasal cannula. Under such circumstances, oxygen concentrator system 100 may increase the flow rate and/or increase the frequency of providing oxygen enriched gas until the inhalation sensor detects an inhalation by the user. If the user switches between breathing modes often, the default mode of providing oxygen enriched gas will cause the oxygen concentrator system to work harder, limiting the portable usage time of the system.

In an embodiment, a mouthpiece 720 is used in combination with an airway delivery device 710 (e.g., a nasal cannula) to provide oxygen enriched gas to a user, as depicted in FIG. 4C. Both mouthpiece 720 and airway delivery device 710 are coupled to an inhalation sensor. In one embodiment, mouthpiece 720 and airway delivery device 710 are coupled to the same inhalation sensor. In an alternate embodiment, mouthpiece 720 and airway delivery device 710 are coupled to different inhalation sensors. In either embodiment, inhalation sensor(s) may now detect the onset of inhalation from either the mouth or the nose. Oxygen concentrator system 100 may be configured to provide oxygen enriched gas to the device (i.e. mouthpiece 720 or airway delivery device 710) that the onset of inhalation was detected. Alternatively, oxygen enriched gas may be provided to both mouthpiece 720 and the airway delivery device 710 if onset of inhalation is detected proximate either device. The use of a dual delivery system, such as depicted in FIG. 4C may be particularly useful for users when they are sleeping and may switch between nose breathing and mouth breathing without conscious effort.

Canister System

Figure 5:
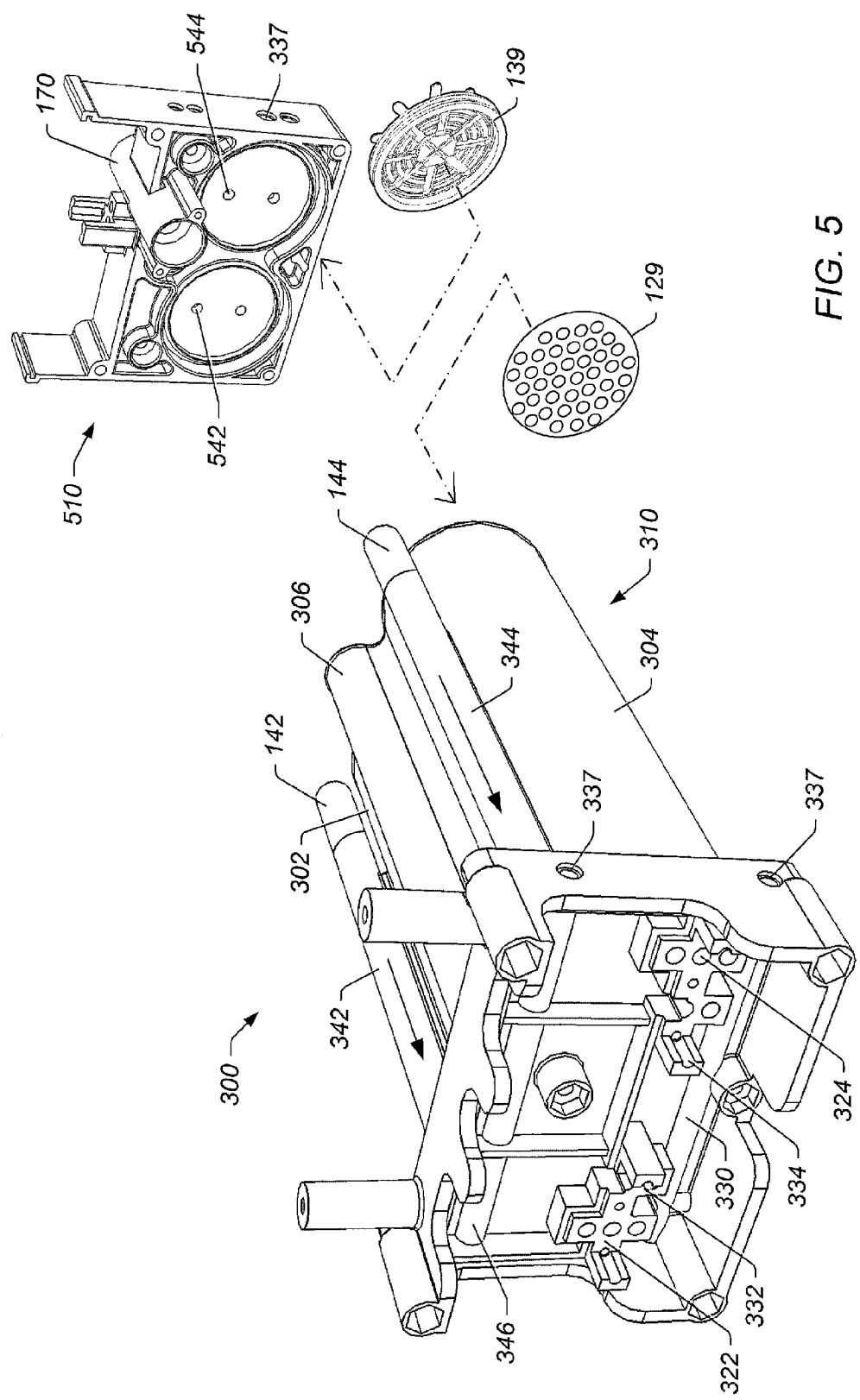
FIG. 5 depicts a perspective view of a dissembled canister system.

Oxygen concentrator system 100 may include at least two canisters, each canister including a gas separation adsorbent. The canisters of oxygen concentrator system 100 may be disposed formed from a molded housing. In an embodiment, canister system 300 includes two housing components 310 and 510, as depicted in FIG. 5. The housing components 310 and 510 may be formed separately and then coupled together. In some embodiments, housing components 310 and 510 may be injection molded or compression molded. Housing components 310 and 510 may be made from a thermoplastic polymer such as polycarbonate, methylene carbide, polystyrene, acrylonitrile butadiene styrene (ABS), polypropylene, polyethylene, or polyvinyl chloride. In another embodiment, housing components 310 and 510 may be made of a thermoset plastic or metal (such as stainless steel or a light-weight aluminum alloy). Lightweight materials may be used to reduce the weight of the oxygen concentrator 100. In some embodiments, the two housings 310 and 510 may be fastened together using screws or bolts. Alternatively, housing components 310 and 510 may be solvent welded together.

As shown, valve seats 320, 322, 324, and 326 and air pathways 330 and 332 may be integrated into the housing component 310 to reduce the number of sealed connections needed throughout the air flow of the oxygen concentrator 100. In various embodiments, the housing components 310 and 410 of the oxygen concentrator 100 may form a two-part molded plastic frame that defines two canisters 302 and 304 and accumulation chamber 106.

Air pathways/tubing between different sections in housing components 310 and 510 may take the form of molded conduits. Conduits in the form of molded channels for air pathways may occupy multiple planes in housing components 310 and 510. For example, the molded air conduits may be formed at different depths and at different x, y, z positions in housing components 310 and 510. In some embodiments, a majority or substantially all of the conduits may be integrated into the housing components 310 and 510 to reduce potential leak points.

In some embodiments, prior to coupling housing components 310 and 510 together, O-rings may be placed between various points of housing components 310 and 510 to ensure that the housing components are properly sealed. In some embodiments, components may be integrated and/or coupled separately to housing components 310 and 510. For example, tubing, flow restrictors (e.g., press fit flow restrictors), oxygen sensors, gas separation adsorbents 139, check valves, plugs, processors, power supplies, etc. may be coupled to housing components 510 and 410 before and/or after the housing components are coupled together.

In some embodiments, apertures 337 leading to the exterior of housing components 310 and 410 may be used to insert devices such as flow restrictors. Apertures may also be used for increased moldability. One or more of the apertures may be plugged after molding (e.g., with a plastic plug). In some embodiments, flow restrictors may be inserted into passages prior to inserting plug to seal the passage. Press fit flow restrictors may have diameters that may allow a friction fit between the press fit flow restrictors and their respective apertures. In some embodiments, an adhesive may be added to the exterior of the press fit flow restrictors to hold the press fit flow restrictors in place once inserted. In some embodiments, the plugs may have a friction fit with their respective tubes (or may have an adhesive applied to their outer surface). The press fit flow restrictors and/or other components may be inserted and pressed into their respective apertures using a narrow tip tool or rod (e.g., with a diameter less than the diameter of the respective aperture). In some embodiments, the press fit flow restrictors may be inserted into their respective tubes until they abut a feature in the tube to halt their insertion. For example, the feature may include a reduction in radius. Other features are also contemplated (e.g., a bump in the side of the tubing, threads, etc.). In some embodiments, press fit flow restrictors may be molded into the housing components (e.g., as narrow tube segments).

In some embodiments, spring baffle 129 may be placed into respective canister receiving portions of housing component 310 and 510 with the spring side of the baffle 129 facing the exit of the canister. Spring baffle 129 may apply force to gas separation adsorbent 139 in the canister while also assisting in preventing gas separation adsorbent 139 from entering the exit apertures. Use of a spring baffle 129 may keep the gas separation adsorbent compact while also allowing for expansion (e.g., thermal expansion). Keeping the gas separation adsorbent 139 compact may prevent the gas separation adsorbent from breaking during movement of the oxygen concentrator system 100).

Figure 6A:
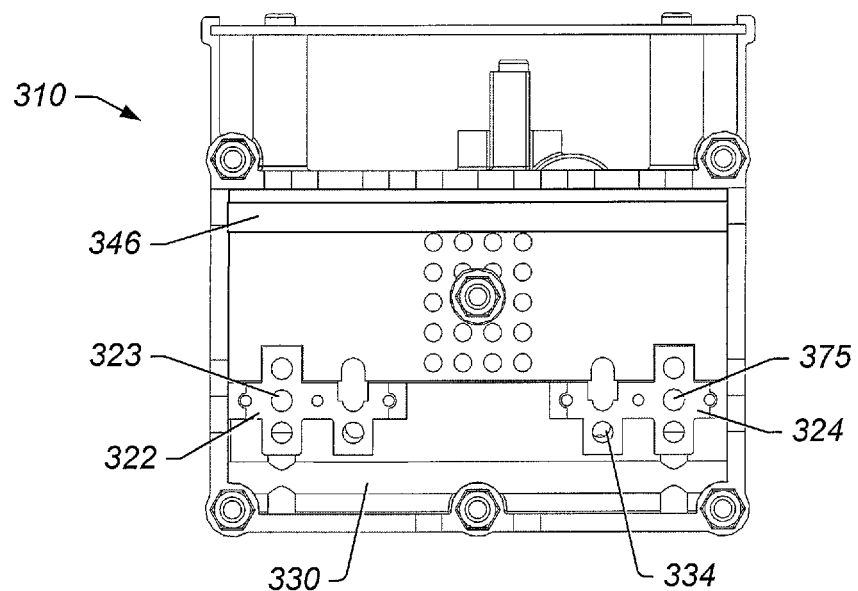
FIG. 6A depicts a perspective view of an end of a canister system.
Figure 6B:
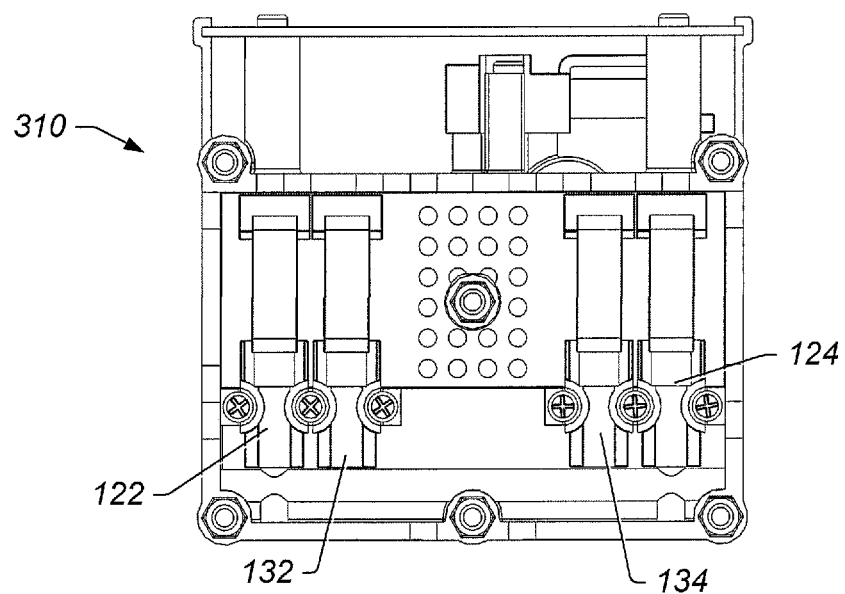
FIG. 6B depicts the assembled end of the canister system end depicted in FIG. 6A.

In some embodiments, pressurized air from the compression system 200 may enter air inlet 306 as depicted in FIG. 2. Air inlet 306 is coupled to inlet conduit 330. Air entering housing component 310 through inlet 306, travels through conduit 330 to valve seats 320 and 328. FIG. 6A and FIG. 6B depict an end view of housing 310. FIG. 6A, depicts an end view of housing 310 prior to fitting valves to housing 310; FIG. 6B depicts an end view of housing 310 with the valves fitted to the housing 310. Valve seats 322 and 324 are configured to receive inlet valves 122 and 124 respectively. Inlet valve 122 is coupled to canister 302 and inlet valve 124 is coupled to canister 304. Housing 310 also includes valve seats 332 and 334 configured to receive outlet valves 132 and 134 respectively. Outlet valve 132 is coupled to canister 302 and outlet valve 134 is coupled to canister 304. Inlet valves 122/124 are used to control the passage of air from conduit 330 to the respective canisters.

In an embodiment, pressurized air is sent into one of canisters 302 or 304 while the other canister is being vented. For example, during use, inlet valve 122 is opened while inlet valve 124 is closed. Pressurized air from compression system 200 is forced into canister 302, while being inhibited from entering canister 304 by inlet valve 124. During pressurization of canister 302, outlet valve 132 is closed and outlet valve 134 is opened. Similar to the inlet valves, outlet valves 132 and 134 are operated out of phase with each other. Each inlet valve seat 322 includes an opening 375 that passes through housing 310 into canister 302. Similarly valve seat 324 includes an opening 325 that passes through housing 310 into canister 302. Air from conduit 330 passes through openings 323 or 325 if the respective valve (322 or 324) is open and enters a canister.

Check valves 142 and 144 are coupled to canisters 302 and 304, respectively. Check valves 142 and 144 are one way valves that are passively operated by the pressure differentials that occur as the canisters are pressurized and vented. Oxygen enriched gas, produced in canisters 302 and 304 pass from the canister into openings 542 and 544 of housing 410. A passage, not shown, links openings 542 and 544 to conduits 342 and 344, respectively. Oxygen enriched gas produced in canister 302 passes from the canister though opening 542 and into conduit 342 when the pressure in the canister is sufficient to open check valve 142. When check valve 142 is open, oxygen enriched gas flows through conduit 342 toward the end of housing 310. Similarly, oxygen enriched gas produced in canister 304 passes from the canister though opening 544 and into conduit 344 when the pressure in the canister is sufficient to open check valve 144. When check valve 144 is open, oxygen enriched gas flows through conduit 344 toward the end of housing 310.

Oxygen enriched gas from either canister, travels through conduit 342 or 344 and enters conduit 346 formed in housing 310. Conduit 346 includes openings that couple the conduit to conduit 342, conduit 344 and accumulator 106. Thus oxygen enriched gas, produced in canister 302 or 304, travels to conduit 346 and passes into accumulator 106.

After some time the gas separation adsorbent will become saturated with nitrogen and will be unable to separate significant amounts of nitrogen from incoming air. When the gas separation adsorbent in a canister reaches this saturation point, the inflow of compressed air is stopped and the canister is vented to remove nitrogen. Canister 302 is vented by closing inlet valve 122 and opening outlet valve 132. Outlet valve 132 releases the vented gas from canister 302 into the volume defined by the end of housing 310. Foam material may cover the end of housing 310 to reduce the sound made by release of gases from the canisters. Similarly, canister 304 is vented by closing inlet valve 124 and opening outlet valve 134. Outlet valve 134 releases the vented gas from canister 304 into the volume defined by the end of housing 310.

While canister 302 is being vented, canister 304 is pressurized to produce oxygen enriched gas in the same manner described above. Pressurization of canister 304 is achieved by closing outlet valve 134 and opening inlet valve 124. The oxygen enriched gas exits canister 304 through check valve 144.

Figure 7A:
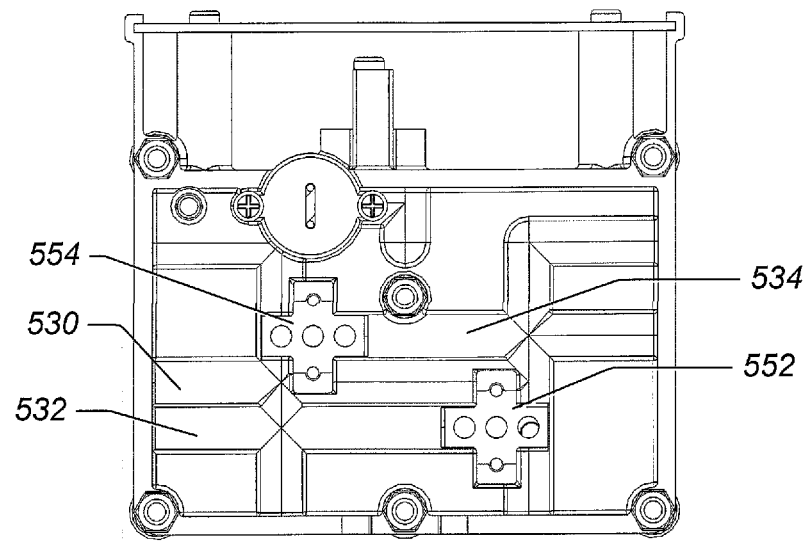
FIG. 7A depicts a perspective view of an opposing end of the canister system depicted in FIGS. 5 and 6A.
Figure 7B:
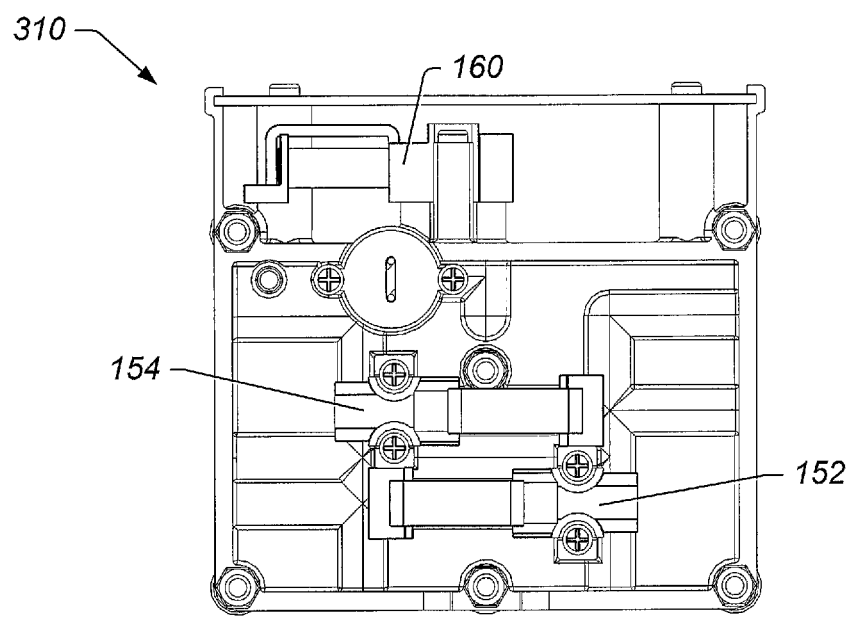
FIG. 7B depicts the assembled opposing end of the canister system end depicted in FIG. 7A.

In an exemplary embodiment, a portion of the oxygen enriched gas may be transferred from canister 302 to canister 304 when canister 304 is being vented of nitrogen. Transfer of oxygen enriched gas from canister 302 to 304, during venting of canister 304, helps to further purge nitrogen (and other gases) from the canister. Flow of oxygen enriched gas between the canisters is controlled using flow restrictors and valves, as depicted in FIG. 1. Three conduits are formed in housing 510 for use in transferring oxygen enriched gas between canisters. Referring to FIG. 7A, conduit 530 couples canister 302 to 304. Flow restrictor 151 (not shown) is disposed in conduit 530, between canister 302 and 304 to restrict flow of oxygen enriched gas during use. Conduit 532 also couples canister 302 to 304. Conduit 532 is coupled to valve seat 552 which receives valve 152, as shown in FIG. 7B. Flow restrictor 153 (not shown) is disposed in conduit 532, between canister 302 and 304. Conduit 534 also couples canister 302 to 304. Conduit 534 is coupled to valve seat 554 which receives valve 154, as shown in FIG. 7B. Flow restrictor 155 (not shown) is disposed in conduit 434, between canister 302 and 304. The pair of equalization/vent valves 152/154 work with flow restrictors 153 and 155 to optimize the air flow balance between the two canisters.

Oxygen enriched gas in accumulator 106 passes through supply valve 160 into expansion chamber 170 which is formed in housing 510. An opening (not shown) in housing 510 couples accumulator 106 to supply valve 160. In an embodiment, expansion chamber may include one or more devices capable of being used to determine an oxygen concentration of gas passing through the chamber.

Power Management

Power for operation of oxygen concentrator system is provided by an internal power supply 180. Having an internal power supply allows portable use of the oxygen concentrator system. In one embodiment, internal power supply 180 includes a lithium ion battery. Lithium ion batteries offer advantages over other rechargeable batteries by being able to provide more power by weight than many other batteries.

In one embodiment, internal power supply 180 includes a total of eight lithium ion battery cells that are arranged with four cells in series and two of these four cell arrays connected in parallel. This is commonly called the 4S2P arrangement. Each battery cell puts out about 4 volts DC when fully charged. With four of these cells connected in series the array puts out about 16 volts. Having two arrays in parallel doubles the available power to operate the device and gives twice the run time of the device on a single charge. Any combination of parallel and series connected battery cells may be used in order to provide sufficient power to operate the oxygen concentrator.

In one embodiment, the compression system, valves, cooling fans and controller may all be powered but an internal power supply. Controller 400 (depicted schematically in FIG. 1) measures the actual output voltage of the internal power supply and adjusts the voltage to the various subsystems to the appropriate level though dedicated circuits on a printed circuit board positioned inside the oxygen concentrator.

Figure 8:
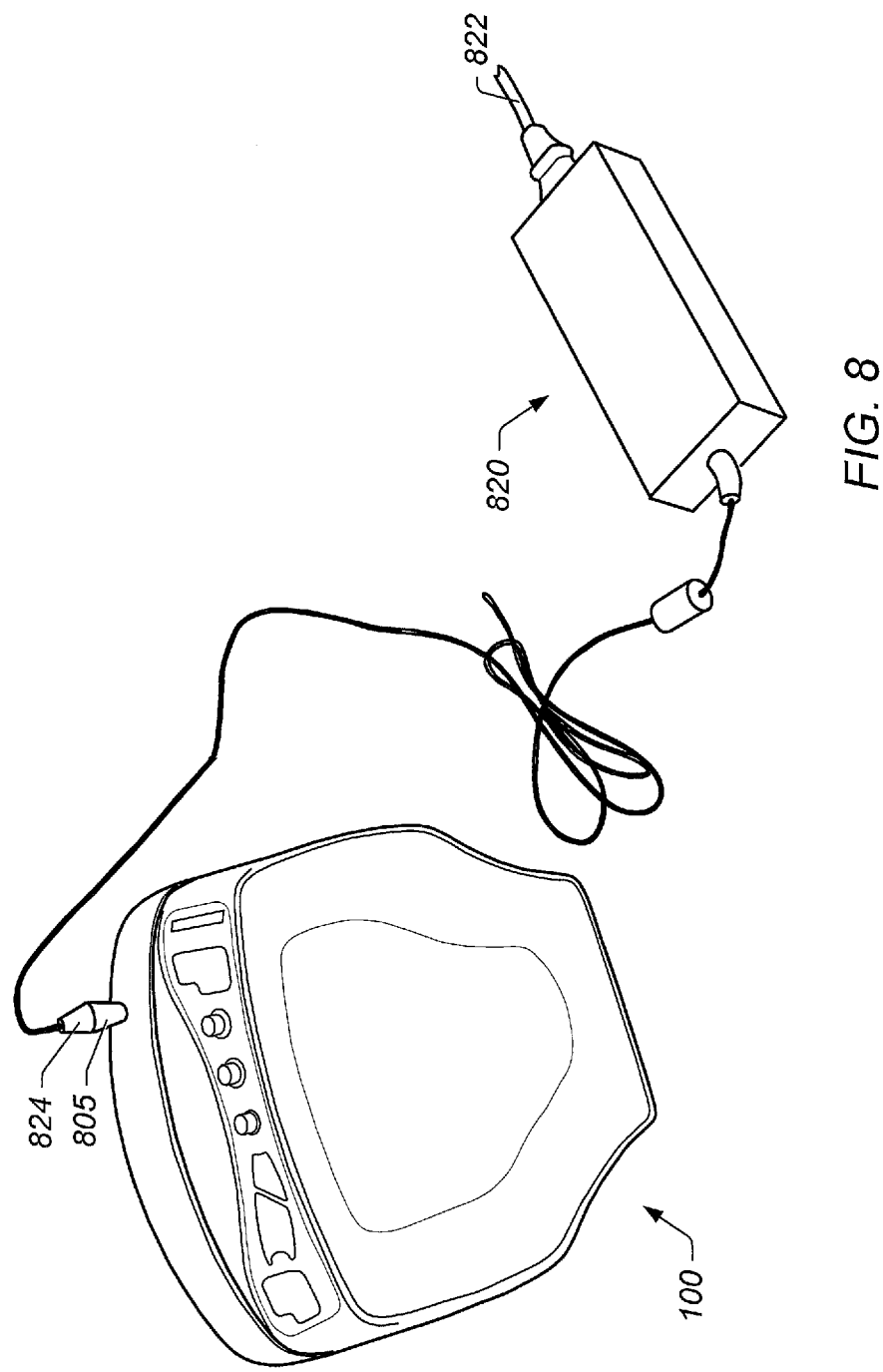
FIG. 8 depicts an external charger coupled to an oxygen concentrator system.

To recharge internal power supply 180, an external charger 820 may be used as depicted in FIG. 8. As used herein, the phrase "external charger" refers to a device capable of coupling to a power source and providing power at sufficient voltage and current to at least charge the internal power supply. In an embodiment, an external charger is capable of providing power at sufficient voltage and current to charge the internal power supply and to run the oxygen concentrator system during charging. The need for an external charger restricts the long term mobility of the oxygen concentrator, since, during recharging, the oxygen concentrator system is restricted to the area where the power source is provided. In order to extend the portable run time of the oxygen concentrator system, an auxiliary power supply may be coupled to the internal power supply to extend the run time of the device and expand the mobility options for the user. In theory, a user of the oxygen concentrator may have limitless portable use of the oxygen concentrator by bringing a sufficient number of auxiliary power supplies.

Figure 9:
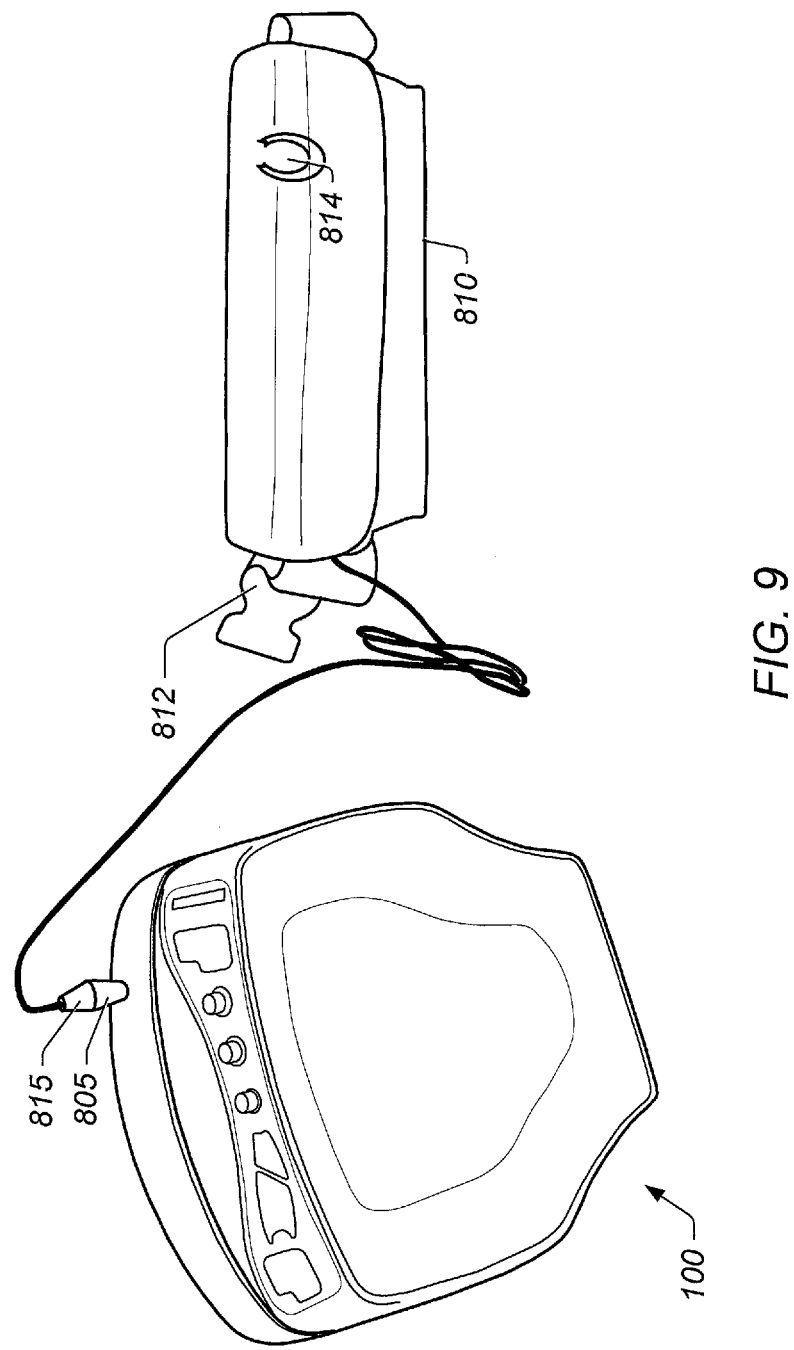
FIG. 9 depicts an auxiliary power supply coupled to an oxygen concentrator system.

FIG. 9 depicts an oxygen concentrator system 100 coupled to an auxiliary power supply 810. Auxiliary power supply 810 may be attachable to oxygen concentrator system 100 using various fasteners 812 (e.g., hook-loop fasters). Alternatively, the auxiliary power supply may be attachable to the patient so as to have the weight of the auxiliary power supply carried by a different portion of the patient's body (e.g., a belt worn around the waist) rather than on a shoulder strap. Physically attaching auxiliary power supply 810 to oxygen concentrator system 100 may improve the portability and ease of use of the oxygen concentrator system. By providing options for attachment, the patient can optimize the carrying mode for their individual circumstance and thereby increase the potential for extending their mobility. Auxiliary power supply 810 may include an external output connector 815 which electrically couples the auxiliary power supply to input port 805 of oxygen concentrator system 100. When electrically coupled to input port 805 of oxygen concentrator system 100, auxiliary power supply 810 may provide power to operate the oxygen concentrator system.

In one embodiment, auxiliary power supply 810 is a lithium ion battery that includes a plurality of battery cells. In one embodiment, auxiliary power supply 810 includes twelve cells arranged in an array of four cells in series with three of these arrays arranged in parallel. This arrangement is generally referred to as a 4S3P arrangement. Any combination of parallel and series connected battery cells may be used in order to provide sufficient power to operate the oxygen concentrator. Auxiliary power supply 810 may also include a battery power indicator. For example, a series of light emitting diodes (LEDs) may light up to indicate an amount of battery power remaining (e.g., 0%, 25%, 50%, 75%, 100%, etc).

Oxygen concentrator system 100 includes a controller 400 (depicted in FIG. 1) configured to manage the power supplied to various components of the oxygen concentrator system. When no external power supplies (e.g., external charger 820 or auxiliary power supply 810) are coupled to oxygen concentrator system 100, controller 400 operates the system using internal power supply 180. Internal power supply 180 provides sufficient power to operate all components. During operation, controller 400 monitors the voltage produced by each of the cells of internal power supply 180. Since internal power supply 180 is capable of producing voltages in excess of the voltage required, controller 400 manages the internal power supply by monitoring the charge level of each cell to maintain consistent discharge from the cells so as not to overload any one cell and cause a runaway discharge.

Lithium batteries are also potentially explosive if the temperature of the battery becomes too high (e.g., above about 14° C.). In an embodiment, controller 400 monitors the temperature of internal power supply 180 and shuts down oxygen concentrator system 100 if the temperature of the internal power supply exceeds a predetermined temperature.

When the stored power of internal power supply 180 is depleted, it is necessary to recharge the internal power supply in order to portably operate oxygen concentrator system 100. Alternatively, an auxiliary power supply 810 may be coupled to oxygen concentrator system 100. When auxiliary power supply 810 is coupled to oxygen concentrator system 100, as depicted in FIG. 9, controller 400 detects this condition and applies power from the auxiliary power supply to the components of the oxygen concentrator system. Internal power supply 180 is electrically decoupled while running oxygen concentrator system 100 using the auxiliary power supply. Once auxiliary power supply 810 is depleted of power, controller 400 will switch the oxygen concentrator system back to operation using internal power supply 180. If internal power supply 180 does not have sufficient power to operate the oxygen concentrator system, controller 400 places the system in a shutdown state.

If internal power supply 180 of the oxygen concentrator system 100 is depleted, an external charger 820 may be coupled to the oxygen concentrator system to provide power to recharge the internal power supply, as depicted in FIG. 8. External charger 820 is also capable of supplying power to operate oxygen concentrator system 100. Thus, power supplied by external charger 820 would need to be significantly greater than power supplied by auxiliary power supply 810 in order to both charge internal power supply 180 and operate oxygen concentrator system 100.

In one embodiment, two charging input ports may be disposed on oxygen concentrator system 100 (not shown). A first input port may be used for coupling an auxiliary power supply to the oxygen concentrator system. The second input port may be used for coupling an external charger to the oxygen concentrator to supply charging power to the internal power supply and operating power to the oxygen concentrator system components. Internal circuitry may be coupled to each port and the internal power supply to provide the appropriate routing of the power when the appropriate power source is coupled to the appropriate charging input port.

In order to provide power to both the internal power supply and the oxygen concentrator system components, the external charger operates at a much higher current than the auxiliary power supply, which is only used to run the oxygen concentrator system components. If the external charger is accidentally coupled to the first input port (the auxiliary power supply input port), there exists the possibility that that one or more system components and/or the power supply may be damaged due to the excessive current. In one embodiment, inhibiting coupling of the wrong power supply to the wrong port may be accomplished by providing different physical dimensions to the first input port and second input port (and the corresponding auxiliary power supply connector and external charger connector). Thus, it may be physically difficult or impossible to couple the external charger to the first input port (i.e., the port for the auxiliary power supply), thus preventing accidental overpowering of the oxygen concentrator system.

Once the auxiliary power supply is depleted, it may be recharged by coupling the auxiliary power supply to an external charger. The external charger used to recharge the auxiliary battery system would have different output current requirements compared to an external power charger used to recharge the internal power supply and run the oxygen concentrator system. Thus, in an embodiment, an oxygen concentrator system includes: an internal power supply, an auxiliary power supply which can be coupled to the oxygen concentrator system to operate the oxygen concentrator system, a first external charger used to operate the oxygen concentrator system and recharge the internal power supply, and a second external charger used to charge the auxiliary battery. While this solution is effective, a traveling user may need to carry multiple external chargers in order to operate the system portably for prolonged periods.

In order to solve the problems created by differing power requirements of an auxiliary power supply and eternal chargers, control circuitry may be provided in both the oxygen concentrator system and the auxiliary power supply. In one embodiment, the oxygen concentrator system 100 includes a single input port 805 which is electrically coupled to the internal power source and the electrical components of the oxygen concentrator system through an internal power control circuit. The internal power control circuit is capable of directing current to the appropriate components based on the power source that is electrically coupled to input port 805. For example, if an auxiliary power supply is coupled to input port 805, as depicted in FIG. 9, the internal power control circuit routes the current to the components of the oxygen concentrator system until the auxiliary power supply is depleted. If an external charger is coupled to the same input port 805, as depicted in FIG. 8, the internal power control circuit routes the current to the components of the oxygen concentrator system and to the internal power supply to charge the internal power supply. Because the internal power supply control circuit is capable of detecting these changes and making the appropriate routing, there is no need to have multiple input ports, and thus the external connectors from the auxiliary power supply and the external chargers may be the same.

Figure 11A:
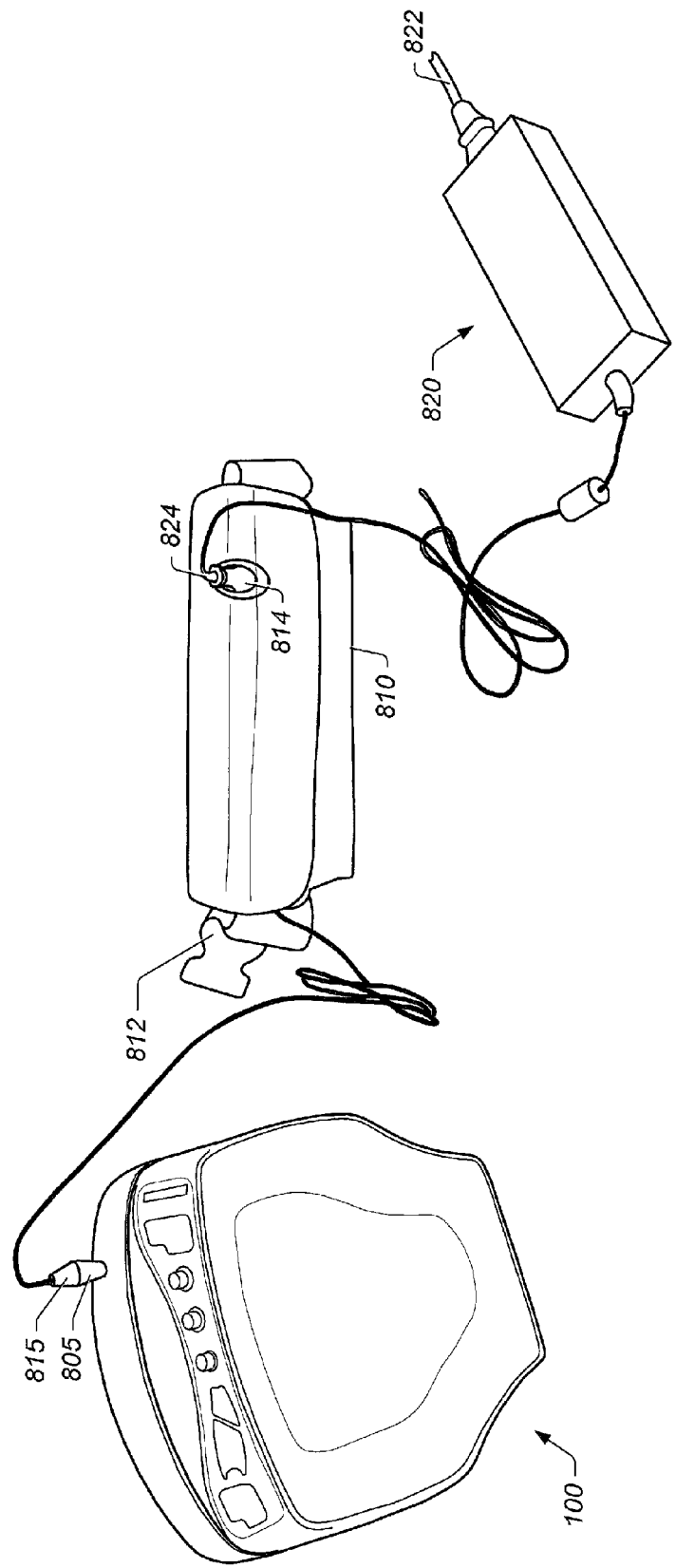
FIG. 11A depicts an auxiliary power supply coupled to an oxygen concentrator system, and an external charger coupled to the auxiliary power supply.

Use of a single port for coupling external charger 820 or auxiliary power supply 810 to input port 805 of oxygen concentrator system 100, allows output connector 815 for the auxiliary power supply to be identical to output connector 824 of the external charger. To reduce the number of chargers required, auxiliary power supply is designed to accept the external charger used for the oxygen concentrator system. Thus, in an embodiment, a single external charger is used to charge the internal power supply of the oxygen concentrator system and the auxiliary power supply. In order to facilitate the dual use of the external charger in this manner, input port 805 for the oxygen concentrator system, is identical to the input port 814 for the auxiliary battery pack. This mechanical compatibility simplifies the operation of the power system for the patient. External charger 820 can charge either oxygen concentrator system 100 or auxiliary power supply 810. This allows a traveling user to need only a single external charger to operate and charge the oxygen concentrator system and auxiliary power supply(s). In this mechanical arrangement, it is possible that auxiliary power supply 810 can be connected to oxygen concentrator system 100 and, simultaneously, external charger 820 can be connected to auxiliary power supply 810 in a daisy chain fashion, as depicted in FIG. 11A.

For this mechanical versatility, it is necessary to provide circuitry and software in both the oxygen concentrator system and the auxiliary power supply that establishes a hierarchy for the current flow. External charger 820 should be able to provide sufficient current to: charge the auxiliary power supply; provide enough current to charge the internal power source of the oxygen concentrator system; and simultaneously provide sufficient current to operate the oxygen concentrator system. Added together this amount of current could charge the batteries of the auxiliary power supply of the internal power supply too rapidly, causing overheating and even a fire in or explosion of the batteries.

Figure 10:
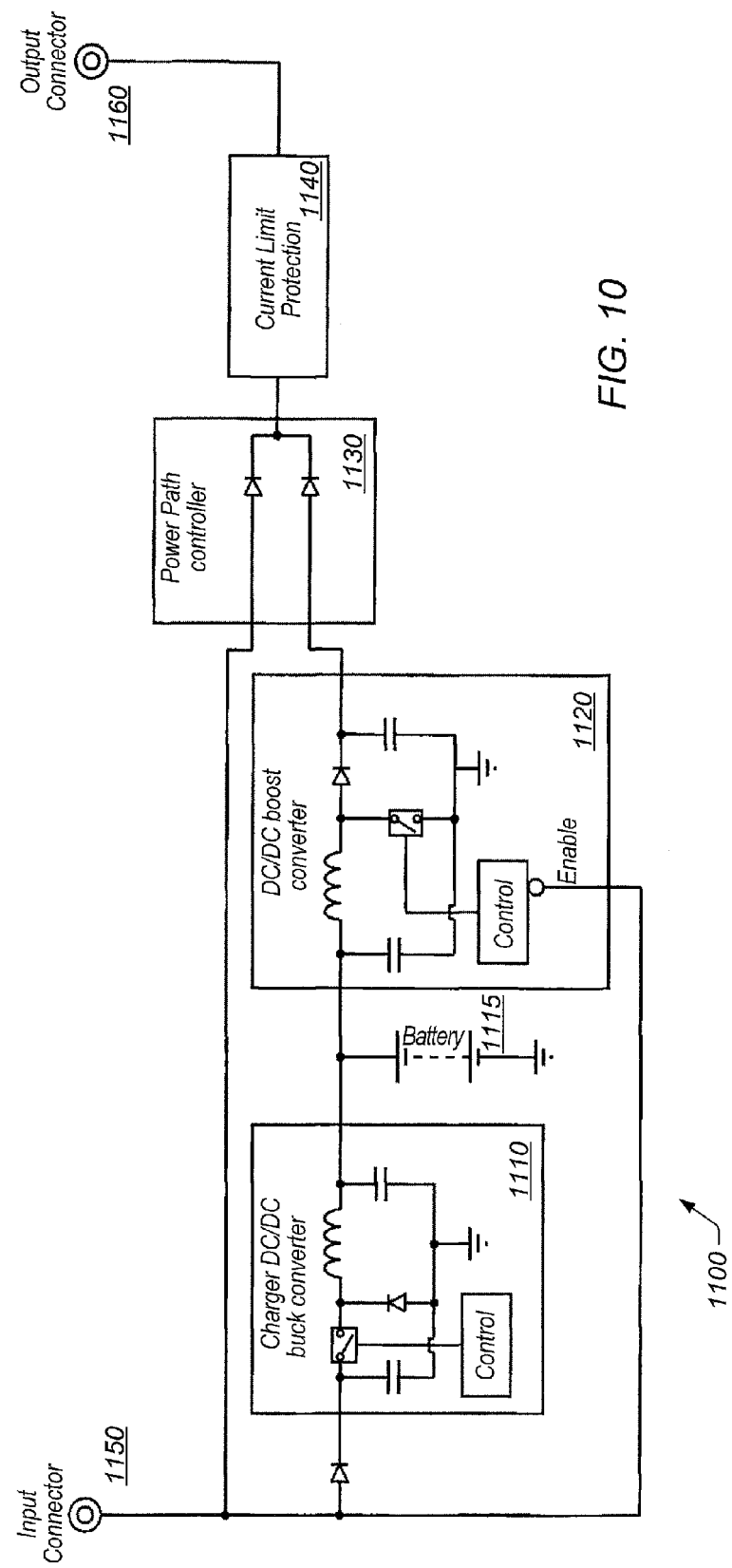
FIG. 10 depicts a schematic diagram of an auxiliary power supply control circuit.

In an embodiment, auxiliary power supply 810 may also have a control circuit 1100 coupled to an input 814 and an output 815. An embodiment of the auxiliary power supply control circuit is depicted in FIG. 10. The auxiliary power supply control circuit includes 3 connectors, one internal connector connecting the internal battery pack 1115 to the control circuit, and two external connectors, output 815 and input 814, to be used by the user. It should be noted that output connector 815 can plug into input port 814 by virtue of the input port for the auxiliary battery pack being substantially identical to input port 805 for the oxygen concentrator system. In order to prevent possible overheating and damage to the auxiliary power supply if output connector 815 is plugged into input port 814, the auxiliary power supply control circuit is designed to place the auxiliary power supply in standby mode, reducing internal current drain.

The auxiliary power supply control circuit may direct flow of current through the auxiliary power supply. The auxiliary power supply control circuit comprises four main blocks: the charger block 1110; the boost block 1120; the power path controller 1130; and the current limit protection circuit 1140.

Charger block 1110 includes a DC/DC buck converter stepping down the input voltage to control the charging cycle of the internal battery. The maximum charging current allowed for a typical lithium ion battery setup is about 2 A. Other current limits would be set depending on the specific configuration and types of battery used. A current limit is generally needed in the case of charging lithium ion battery cells and to size power from the external charger. The external charger requires a voltage on its input greater than the internal voltage of the battery, thus additional circuitry can be implemented to detect the voltage difference between input voltage and internal battery voltage before enabling the charging process. In FIG. 10 a blocking diode is placed at the input of the DC/DC buck converter to block any reverse voltage coming of the internal battery.

Boost block 1120 includes a basic boost converter with a switching device, a diode and an output capacitor. An enable pin is provided to enable/disable the control signal which would save power. The enable pin is activated by a logic low signal, this pin is assumed to be internally pulled low when it has no connection therefore enabling the controller. In an alternate embodiment, a synchronous boost converter could be used instead to improve efficiency.

Power path controller 1130 includes a MOSFET driver controlled by a voltage comparator. The power path controller emulates an approximate ideal OR'ing diode configured to switch between power supplies with minimum power losses, such that the power supply with the highest voltage is assigned to the output.

The current limit protection circuit will cut off power when current exceeds a fixed current limit. The protection circuit can include a manual reset button or a timed reset signal. The purpose of this protection is to protect the boost converter from overload conditions and to determine the maximum power of the external charger.

Control circuit 1100 is capable of automatically detecting various power conditions and directing the current appropriately through the auxiliary power supply. For example, when the internal battery of auxiliary power supply 810 is charged and output connector 815 is not connected to any load, boost converter 1110 is activated and the stepped up regulated voltage is available at output connector 815 for the user. Thus the auxiliary power supply 810 is ready, upon connection with the oxygen concentrator system, to supply power to run the oxygen concentrator system.

When control circuit 1100 detects that the battery is discharged, the internal protection circuit cuts off power from the battery, and no voltage is available to output connector 815.

Control circuit 1100 permits auxiliary power supply 810 to recognize when it is put into service. When output connector 815 is not connected to a load, control circuit 1100 is always active, and requires a significant amount of power to stay active. Thus, auxiliary power supply 810 is in a continual state of discharging itself, even when not being used to run the oxygen concentrator system. As a result, auxiliary power supply 810 can become fully discharged and be useless to the use when needed.

Figure 11B:
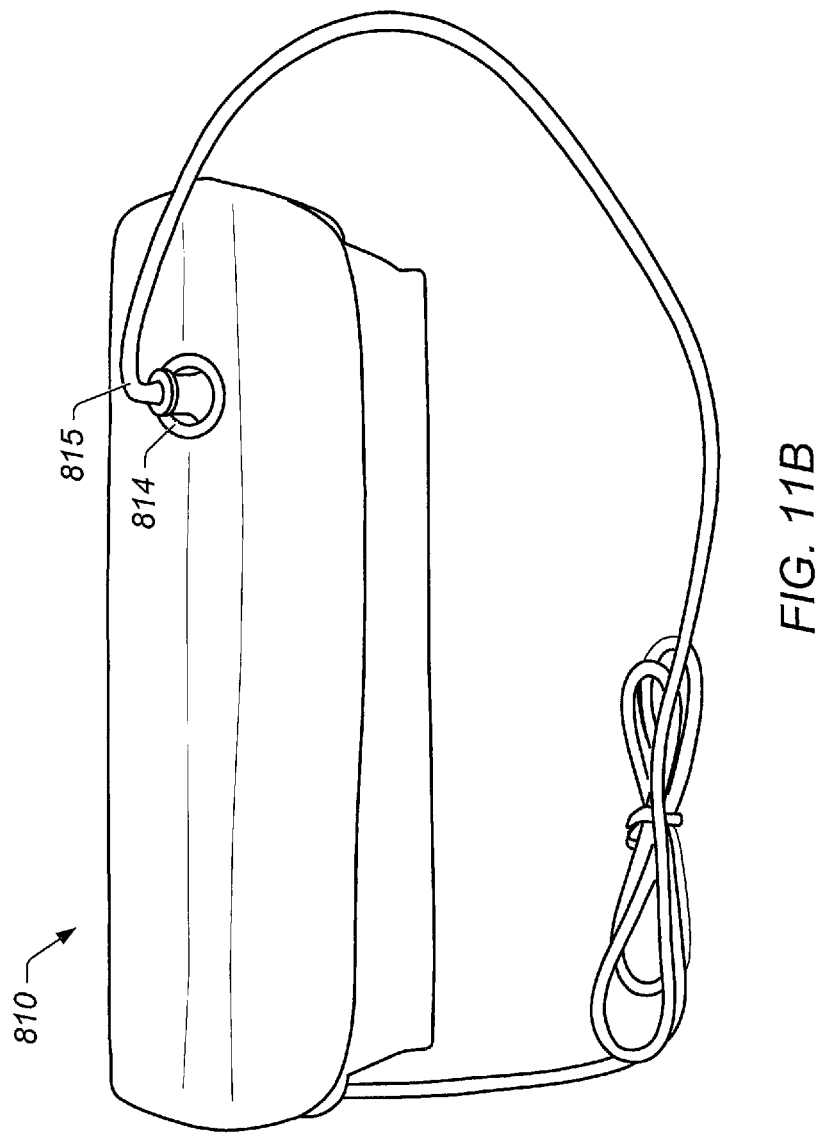
FIG. 11B depicts an output connector of an auxiliary power supply coupled to the input port of the auxiliary power supply.

To inhibit unintentional discharge, a standby mode is embedded in control circuit 1100. Standby mode can be initiated by the user connecting output connector 815 into input port 814, as depicted in FIG. 11B. Upon detection of this situation, control circuit 1100 uses the available output voltage to disable boost block 1120 through the enable line connection therefore reducing the operational quiescent currents needed to power the control and switching devices of the boost block. Once boost block 1120 is disabled, the output voltage drops to less than the internal voltage of battery 1115, because of the internal diode of the boost block, which provides a continuous path for battery 1115 to output connector 815. Maintaining this voltage on the output continuously will disable boost block 1120 through the same enable line. At the same time, the buck block 1110 is disabled, because a buck converter cannot step up the voltage, since the voltage at the input of the buck converter is the voltage of battery 1115 minus the forward voltage of the two series diodes shown in FIG. 10, when the connection between output connector 815 and input port 814 is established. Additional circuitry is designed inside buck block 1110 to completely disable the control when the input voltage is lower or equal to the voltage of battery 1115.

Thus a user, upon completion of charging of auxiliary power supply 810, can place the auxiliary power supply into a standby mode by connecting output connector 815 to input port 814. In standby mode the boost converter and the buck converter are disabled to reduce the darin on the battery cells. This extends the power storage time of auxiliary power supply 820, and avoids potentially dangerous self charging of the auxiliary power supply.

When battery 1115 of auxiliary power supply 810 is discharged, control circuit 1110 of will disconnect power from the battery. Connection of output connector 815 to input port 814 will have no effect.

When external charger 820, with an output voltage higher than the output voltage of battery 1115, is plugged into input port 814, boost block 1120 is disabled and buck block 1110 is enabled. Enabling buck block 1110 allows battery 1115 to be charged by current from external charger 820. In addition, power path controller 1130 will enable a channel connected directly to input port 814 thus providing voltage to output connector 815 from external charger 820. Thus external charger 820 may be coupled to auxiliary power supply 810 while the auxiliary power supply is coupled to oxygen concentrator system 100, as depicted in FIG. 11, such that external charger can: charge the auxiliary power supply; provide enough current to charge the internal power source of the oxygen concentrator system; and simultaneously provide sufficient current to operate the oxygen concentrator system.

Controller System

Operation of oxygen concentrator system 100 may be performed automatically using an internal controller 400 coupled to various components of the oxygen concentrator system, as described herein. Controller 400 includes one or more processors 410 and internal memory 420, as depicted in FIG. 1. Methods used to operate and monitor oxygen concentrator system 100 may be implemented by program instructions stored in memory 420 or a carrier medium coupled to controller 400, and executed by one or more processors 410. A memory medium may include any of various types of memory devices or storage devices. The term "memory medium" is intended to include an installation medium, e.g., a Compact Disc Read Only Memory (CD-ROM), floppy disks, or tape device; a computer system memory or random access memory such as Dynamic Random Access Memory (DRAM), Double Data Rate Random Access Memory (DDR RAM), Static Random Access Memory (SRAM), Extended Data Out Random Access Memory (EDO RAM), Rambus Random Access Memory (RAM), etc.; or a non-volatile memory such as a magnetic media, e.g., a hard drive, or optical storage. The memory medium may comprise other types of memory as well, or combinations thereof. In addition, the memory medium may be located in a first computer in which the programs are executed, or may be located in a second different computer that connects to the first computer over a network, such as the Internet. In the latter instance, the second computer may provide program instructions to the first computer for execution. The term "memory medium" may include two or more memory mediums that may reside in different locations, e.g., in different computers that are connected over a network.

In some embodiments, controller 400 includes processor 410 that includes, for example, one or more field programmable gate arrays (FPGAs), microcontrollers, etc. included on a circuit board disposed in oxygen concentrator system 100. Processor 410 is capable of executing programming instructions stored in memory 420. In some embodiments, programming instructions may be built into processor 410 such that a memory external to the processor may not be separately accessed (i.e., the memory 420 may be internal to the processor 410).

Processor 410 may be coupled to various components of oxygen concentrator system 100, including, but not limited to compression system 200, one or more of the valves used to control fluid flow through the system (e.g., valves 122, 124, 132, 134, 152, 154, 160), oxygen sensor 165, pressure sensor 194, flow rate monitor 180, temperature sensors, fans, and any other component that may be electrically controlled. In some embodiments, a separate processor (and/or memory) may be coupled to one or more of the components.

Controller 400 is programmed to operate oxygen concentrator system 100 and is further programmed to monitor the oxygen concentrator system for malfunction states. For example, in one embodiment, controller 400 is programmed to trigger an alarm if the system is operating and no breathing is detected by the user for a predetermined amount of time. For example, if controller 400 does not detect a breath for a period of 75 seconds, an alarm LED may be lit and/or an audible alarm may be sounded. If the user has truly stopped breathing, for example, during a sleep apnea episode, the alarm may be sufficient to awaken the user, causing the user to resume breathing. The action of breathing may be sufficient for controller 400 to reset this alarm function. Alternatively, if the system is accidently left on when output conduit 192 is removed from the user, the alarm may serve as a reminder for the user to turn oxygen concentrator system 100 off.

Controller 400 is further coupled to oxygen sensor 165, and may be programmed for continuous or periodic monitoring of the oxygen concentration of the oxygen enriched gas passing through expansion chamber 170. A minimum oxygen concentration threshold may be programmed into controller 400, such that the controller lights an LED visual alarm and/or an audible alarm to warn the patient of the low concentration of oxygen.

Controller 400 is also coupled to internal power supply 180 and is capable of monitoring the level of charge of the internal power supply. A minimum voltage and/or current threshold may be programmed into controller 400, such that the controller lights an LED visual alarm and/or an audible alarm to warn the patient of low power condition. The alarms may be activated intermittently and at an increasing frequency as the battery approaches zero usable charge.

Further functions of controller 400 are described in detail in other sections of this disclosure.

Outer Housing—Control Panel

Figure 13:
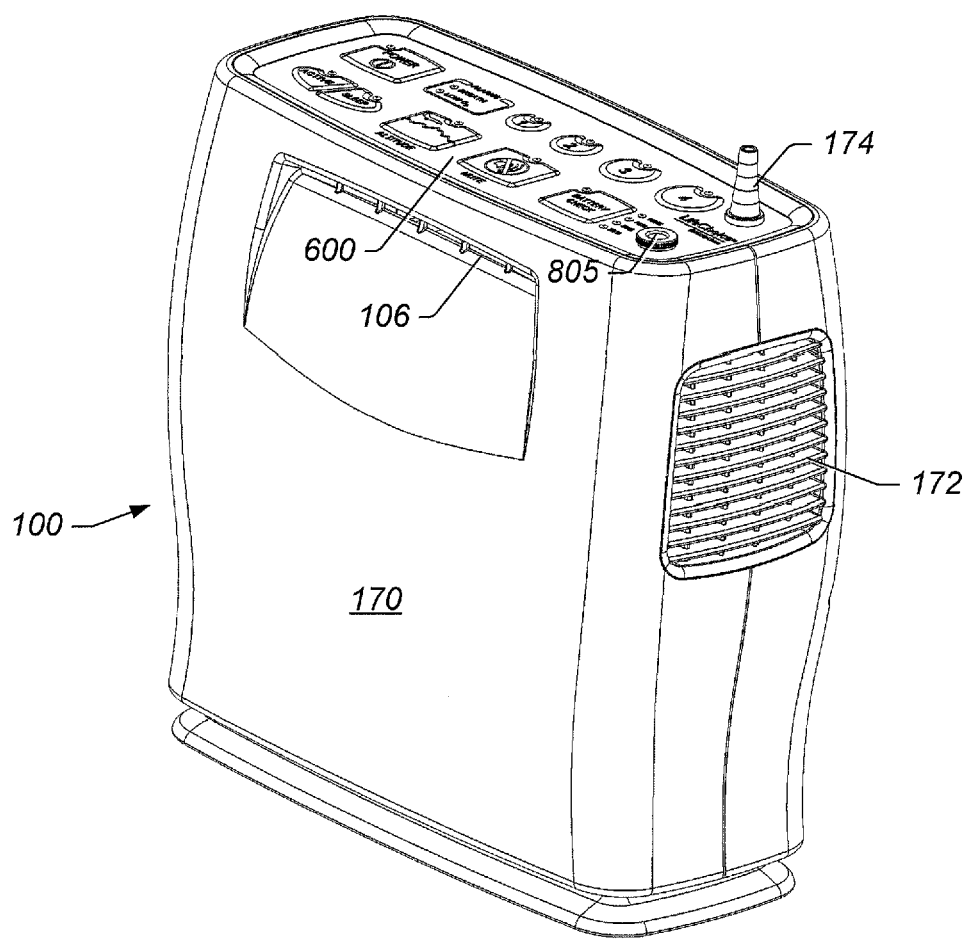
FIG. 13 depicts an outer housing for an oxygen concentrator.

FIG. 13 depicts an embodiment of an outer housing 170 of an oxygen concentrator system 100. In some embodiments, outer housing 170 may be comprised of a light-weight plastic. Outer housing includes compression system inlets 106, cooling system passive inlet 101 and outlet 172 at each end of outer housing 170, outlet port 174, and control panel 600. Inlet 101 and outlet 172 allow cooling air to enter housing, flow through the housing, and exit the interior of housing 170 to aid in cooling of the oxygen concentrator system. Compression system inlets 101 allow air to enter the compression system. Outlet port 174 is used to attach a conduit to provide oxygen enriched gas produced by the oxygen concentrator system to a user.

Figure 14:
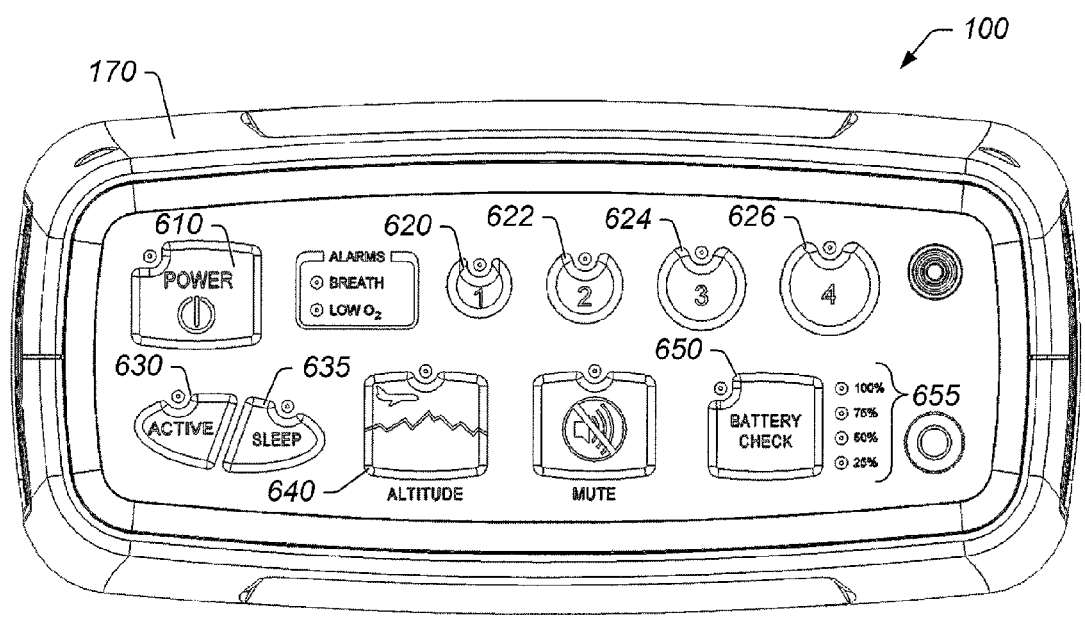
FIG. 14 depicts a control panel for an oxygen concentrator.

Control panel 600 serves as an interface between a user and controller 400 to allow the user to initiate predetermined operation modes of the oxygen concentrator system and to monitor the status of the system. Charging input port 805 may be disposed in control panel 600. FIG. 14 depicts an embodiment of control panel 600.

In some embodiments, control panel 600 may include buttons to activate various operation modes for the oxygen concentrator system. For example, control panel may include power button 610, dosage buttons (e.g., 1 LPM button 620, 2 LPM button 622, and 3 LPM button 624, and 4 LPM button 626), active mode button 630, sleep mode button 635, and a battery check button 650. In some embodiments, one or more of the buttons may have a respective LED that may illuminate when the respective button is pressed (and may power off when the respective button is pressed again). Power button 610 may power the system on or off. If the power button is activated to turn the system off, controller 400 may initiate a shutdown sequence to place the system in a shutdown state (e.g., a state in which both canisters are pressurized). Dosage buttons 620, 622, 624, and 626 allows the proper prescription level to be selected. Altitude button 640 may be selected when a user is going to be in a location at a higher elevation than the oxygen concentrator is regularly used by the user. The adjustments made by the oxygen concentrator system in response to activating altitude mode are described in more detail herein. Battery check button 650 initiates a battery check routine in the oxygen concentrator system which results in a relative battery power remaining LED 655 being illuminated on control panel 600.

A user may have a low breathing rate or depth if relatively inactive (e.g., asleep, sitting, etc.) as assessed by comparing the detected breathing rate or depth to a threshold. The user may have a high breathing rate or depth if relatively active (e.g., walking, exercising, etc.). An active/sleep mode may be assessed automatically and/or the user may manually indicate a respective active or sleep mode by pressing button 630 for active mode and button 635 for sleep mode. The adjustments made by the oxygen concentrator system in response to activating active mode or sleep mode are described in more detail herein.

Methods of Delivery of Oxygen Enriched Gas

The main use of an oxygen concentrator system is to provide supplemental oxygen to a user. Generally, the amount of supplemental oxygen to be provided is assessed by a physician. Typical prescribed amounts of supplemental oxygen may range from about 1 LPM to up to about 10 LPM. The most commonly prescribed amounts are 1 LPM, 2 LPM, 3 LPM, and 4 LPM. Generally, oxygen enriched gas is provided to the use during a breathing cycle to meet the prescription requirement of the user. As used herein the term "breathing cycle" refers to an inhalation followed by an exhalation of a person.

In order to minimize the amount of oxygen enriched gas that is needed to be produced to meet the prescribed amounts, controller 400 may be programmed to time delivery of the oxygen enriched gas with the user's inhalations. Releasing the oxygen enriched gas to the user as the user inhales may prevent unnecessary oxygen generation (further reducing power requirements) by not releasing oxygen, for example, when the user is exhaling Reducing the amount of oxygen required may effectively reduce the amount of air compressing needed for oxygen concentrator 100 (and subsequently may reduce the power demand from the compressors).

Oxygen enriched gas, produced by oxygen concentrator system 100 is stored in an oxygen accumulator 106 and released to the user as the user inhales. The amount of oxygen enriched gas provided by the oxygen concentrator system is controlled, in part, by supply valve 160. In an embodiment, supply valve 160 is opened for a sufficient amount of time to provide the appropriate amount of oxygen enriched gas, as assessed by controller 400, to the user. In order to minimize the amount of oxygen required to meet the prescription requirements of a use, the oxygen enriched gas may be provided in a bolus when a user's inhalation is first detected. For example, the bolus of oxygen enriched gas may be provided in the first few milliseconds of a user's inhalation.

In an embodiment, pressure sensor 194 and/or flow rate sensor 185 may be used to determine the onset of inhalation by the user. For example, the user's inhalation may be detected by using pressure sensor 194. In use, a conduit for providing oxygen enriched gas is coupled to a user's nose and/or mouth (e.g., using a nasal cannula or face mask). At the onset of an inhalation, the user begins to draw air into their body through the nose and/or mouth. As the air is drawn in, a negative pressure is generated at the end of the conduit, due, in part, to the venturi action of the air being drawn across the end of the delivery conduit. Pressure sensor 194 may be operable to create a signal when a drop in pressure is detected, to signal the onset of inhalation. Upon detection of the onset of inhalation, supply valve 160 is controlled to release a bolus of oxygen enriched gas from the accumulator 106.

In some embodiments, pressure sensor 194 may provide a signal that is proportional to the amount of positive or negative pressure applied to a sensing surface. The amount of the pressure change detected by pressure sensor 194 may be used to refine the amount of oxygen enriched gas being provided to the user. For example, if a large negative pressure change is detected by pressure sensor 194, the volume of oxygen enriched gas provided to the user may be increased to take into account the increased volume of gas being inhaled by the user. If a smaller negative pressure is detected, the volume of oxygen enriched gas provided to the user may be decreased to take into account the decreased volume of gas being inhaled by the user. A positive change in the pressure indicates an exhalation by the user and is generally a time that release of oxygen enriched gas is discontinued. Generally while a positive pressure change is sensed, valve 160 remains closed until the next onset of inhalation.

In some embodiments, the sensitivity of the pressure sensor 194 may be affected by the physical distance of the pressure sensor 194 from the user, especially if the pressure sensor is located in oxygen concentrator system 100 and the pressure difference is detected through the tubing coupling the oxygen concentrator system to the user. In some embodiments, the pressure sensor may be placed in the airway delivery device used to provide the oxygen enriched gas to the user. A signal from the pressure sensor may be provided to controller 400 in the oxygen concentrator 100 electronically via a wire or through telemetry such as through Bluetooth™ or other wireless technology.

In an embodiment, the user's inhalation may be detected by using flow rate sensor 185. In use, a conduit for providing oxygen enriched gas is coupled to a user's nose and/or mouth (e.g., using a nasal cannula or face mask). At the onset of an inhalation, the user begins to draw air into their body through the nose and/or mouth. As the air is drawn in, an increase in flow of gas passing through conduit is created. Flow rate sensor 185 may be operable to create a signal when an increase in flow rate is detected, to signal the onset of inhalation. Upon detection of the onset of inhalation, supply valve 160 is controlled to release a bolus of oxygen enriched gas from the accumulator 106.

A user breathing at a rate of 30 breaths per minute (BPM) during an active state (e.g., walking, exercising, etc.) may consume two and one-half times as much oxygen as a user who is breathing at 12 BPM during a sedentary state (e.g., asleep, sitting, etc.). Pressure sensor 194 and/or flow rate sensor 185 may be used to determine the breathing rate of the user. Controller 400 may process information received from pressure sensor 194 and/or flow rate sensor 185 and determine a breathing rate based on the frequency of the onset of inhalation. The detected breathing rate of the user may be used to adjust the bolus of oxygen enriched gas. The volume of the bolus of oxygen enriched gas may be increased as the users breathing rate increase, and may be decreased as the users breathing rate decreases. Controller 400 may automatically adjust the bolus based on the detected activity state of the user. Alternatively, the user may manually indicate a respective active or sedentary mode by selecting the appropriate option on control panel 600.

In some embodiments, if the user's current activity level as assessed using the detected user's breathing rate exceeds a predetermined threshold, controller 400 may implement an alarm (e.g., visual and/or audio) to warn the user that the current breathing rate is exceeding the delivery capacity of the oxygen concentrator system. For example, the threshold may be set at 20 breaths per minute.

Figure 12:
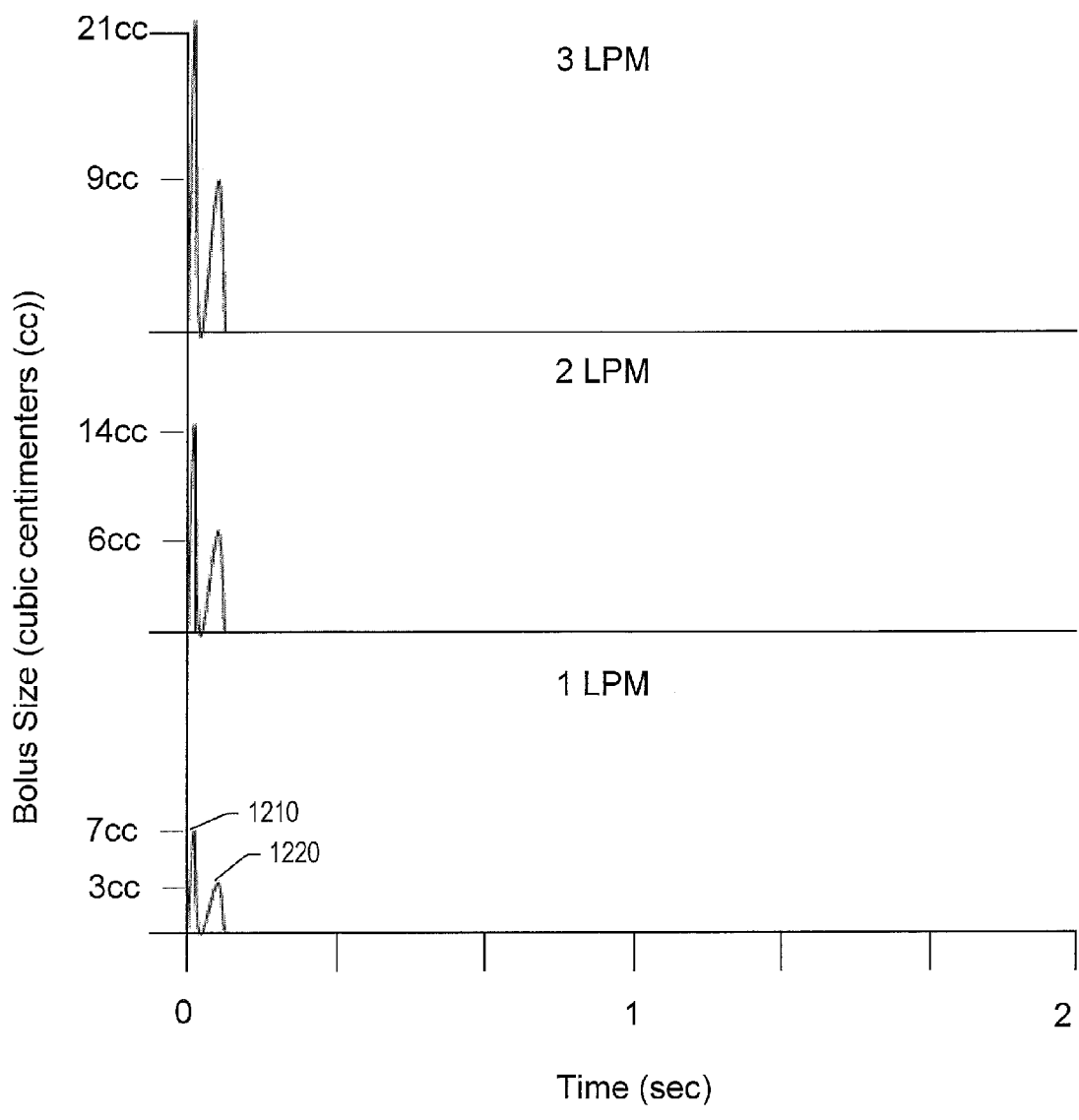
FIG. 12 depicts various profiles for providing oxygen enriched gas from an oxygen concentrator.

In some embodiments, as seen in FIG. 12, the bolus of provided oxygen enriched gas may include two or more pulses. For example, with a one liter per minute (LPM) delivery rate, the bolus may include two pulses: a first pulse 1210 at approximately 7 cubic centimeters and a second pulse 1220 at approximately 3 cubic centimeters. Other delivery rates, pulse sizes, and number of pulses are also contemplated. For example, at 2 LPMs, the first pulse may be approximately 14 cubic centimeters and a second pulse may be approximately 6 cubic centimeters and at 3 LPMs, the first pulse may be approximately 21 cubic centimeters and a second pulse may be approximately 9 cubic centimeters. In some embodiments, the larger pulse 1210 may be provided when the onset of inhalation is detected (e.g., detected by pressure sensor 194). In some embodiments, the pulses may be provided when the onset of inhalation is detected and/or may be spread timewise evenly through the breath. In some embodiments, the pulses may be stair-stepped through the duration of the breath. In some embodiments, the pulses may be distributed in a different pattern. Additional pulses may also be used (e.g., 3, 4, 5, etc. pulses per breath). While the first pulse 1210 is shown to be approximately twice the second pulse 1220, in some embodiments, the second pulse 1220 may be larger than the first pulse 1210. In some embodiments, pulse size and length may be controlled by, for example, supply valve 160 which may open and close in a timed sequence to provide the pulses. A bolus with multiple pulses may have a smaller impact on a user than a bolus with a single pulse. The multiple pulses may also result in less drying of a user's nasal passages and less blood oxygen desaturation. The multiple pulses may also result in less oxygen waste.

In some embodiments, the sensitivity of the oxygen concentrator 100 may be selectively attenuated to reduce false inhalation detections due to movement of air from a different source (e.g., movement of ambient air). For example, the oxygen concentrator 100 may have two selectable modes—an active mode and an inactive mode. In some embodiments, the user may manually select a mode (e.g., through a switch or user interface). In some embodiments, the mode may be automatically selected by the oxygen concentrator 100 based on a detected breathing rate. For example, the oxygen concentrator 100 may use the pressure sensor 194 to detect a breathing rate of the user. If the breathing rate is above a threshold, the oxygen concentrator 100 may operate in an active mode (otherwise, the oxygen concentrator may operate in an inactive mode). Other modes and thresholds are also contemplated.

In some embodiments, in active mode, the sensitivity of the pressure sensor 194 may be mechanically, electronically, or programmatically attenuated. For example, during active mode, controller 400 may look for a greater pressure difference to indicate the start of a user breath (e.g., an elevated threshold may be compared to the detected pressure difference to determine if the bolus of oxygen should be released). In some embodiments, the pressure sensor 194 may be mechanically altered to be less sensitive to pressure differences. In some embodiments, an electronic signal from the pressure sensor may be electronically altered to ignore small pressure differences. This can be useful when in active mode. In some embodiments, during the inactive mode the sensitivity of the pressure sensor may be increased. For example, the controller 400 may look for a smaller pressure difference to indicate the start of a user breath (e.g., a smaller threshold may be compared to the detected pressure difference to determine if the bolus of oxygen should be released). In some embodiments, with increased sensitivity, the response time for providing the bolus of oxygen during the user's inhalation may be reduced. The increased sensitivity and smaller response time may reduce the size of the bolus necessary for a given flow rate equivalence. The reduced bolus size may also reduce the size and power consumption of the oxygen concentrator 100

Providing a Bolus Based on Inhalation Profile

In an embodiment, the bolus profile can be designed to match the profile of a particular user. To do so, an inhalation profile may be generated based on information gathered from pressure sensor 194 and flow rate sensor 185. An inhalation profile is assessed based on, one or more of the following parameters: the breathing rate of the user; the inhalation volume of the user; the exhalation volume of the user; the inhalation flow rate of the user; and the exhalation flow rate of the user. The breathing rate of the user may be assessed by detecting the onset of inhalation using pressure sensor 194 or flow rate sensor 185 as previously discussed. Inhalation volume may be assessed by measuring the change in pressure during inhalation and calculating or empirically assessing the inhalation volume based on the change in pressure. Alternatively, inhalation volume may be assessed by measuring the flow rate during inhalation and calculating or empirically assessing the inhalation volume based on the flow rate and the length of the inhalation. Exhalation volume may be assessed in a similar manner using either positive pressure changes during exhalation, or flow rate and exhalation time. Inhalation flow rate of the user is measured from shortly after the onset of inhalation. Detection of the end of inhalation may be from the pressure sensor or the flow rate sensor. When onset of inhalation is detected by the pressure sensor, the onset is characterized by a drop in pressure. When the pressure begins to increase, the inhalation is considered complete. When onset of inhalation is detected by the flow rate sensor, the onset is characterized by an increase in the flow rate. When the flow rate begins to decrease, the inhalation is considered complete.

There is a minimum amount of oxygen necessary for a person to remain conscious. A person who is breathing rapidly is bringing in a lower volume of air in each breath, and thus, requires less oxygen enriched gas per inhalation. While there is some variation from patient to patient, this relationship can be used to establish the mean flow rate for each breath mathematically. By measuring a large population of patients, the profile of the relative flow from onset of inhalation to the onset of exhalation may be established. Using this flow profile as a template, the calculated actual flow based on breathing rate can be adjusted mathematically to a calculated actual flow profile. This profile can be used to adjust the opening and closing of the delivery valve to create an idealized profile for the patient based on their breathing rate. Inhalation profile data gathered from a population of users may be used to create an algorithm that makes the appropriate adjustments based on the detected inhalation profile. Alternatively, a look up table may be used to control valve actuation durations and pulse quantities based on a detected inhalation profile.

Measuring the inhalation profile of the patient provides a more accurate basis for control of the bolus of oxygen enriched gas being provided to the patient. For example, basing the delivery of oxygen enriched gas on the onset of inhalation may not take into account differences between individual users. For example, people having a similar breathing rate can have different inhalation/exhalation volume, inhalation/exhalation flow rates and, thus, different bolus requirements necessary to produce the prescribed amount of oxygen. In one embodiment, an inhalation profile is created based on the flow rate of air during inhalation and the duration of inhalation. The inhalation profile can then be used as a predictor of the volume of air taken in by a specific user during inhalation. Thus, inhalation profile information can be used to modify the amount of oxygen enriched air provided to the user to ensure that the prescribed level of oxygen is received. The amount of oxygen provided to a user may be adjusted by modifying the frequency and or duration of release of oxygen enriched gas from the accumulator with supply valve 160. By tracking the inhalation profile of the patient controller adjusts the delivery supply valve actuation to idealize the bolus profile to provide the oxygen at the maximum rate without causing wasteful retrograde flow.

Altitude Compensation

An oxygen concentrator system uses a pressure swing adsorption process to separate oxygen from nitrogen in air. In order to have an effective separation of the oxygen from the nitrogen, the compressed air in the canisters should reach a minimum absolute pressure. Generally, the compressors move a fixed amount of ambient air with each revolution of the drive motor. Based on the speed that the motors are being operated, the time required to reach the minimum pressure can be predicted and programmed into the controller. Thus, the timing of the actuation of inlet and outlet valves for pressurization and venting can be based on the motor speed and is generally assumed to be constant. At higher altitudes, air pressure drops and less air is available for each revolution of the drive. Consequently, the time it takes for a compressor to pressurize the canister to the minimum pressure at higher altitudes is longer than the time it would take for the compression system to reach the minimum pressure at sea level.

In an embodiment, controller 400 includes a mode of operation that is capable of compensating for use at elevations significantly above sea level. Controller 400 can compensate for the thinner air at higher elevations by adjusting the motor speed and or valve timing to ensure that the proper pressure is reached inside the canisters. In one embodiment, a compression system includes a motor 220 coupled to a compressor 210, as depicted in FIGS. 3A and 3B. A default motor speed may be set by controller 400 which is based on an air pressure at or proximate to the pressure of air at sea level. At high altitudes, controller may alter the motor to run at a speed greater than the default speed. Running the motor at a faster speed ensures that a canister reaches the appropriate pressure for oxygen enriched gas production, before being vented in preparation of the next cycle. Using a motor control scheme, the timing of the inlet and outlet valves would not be modified.

Alternatively, the valve timing sequence may be altered to ensure the appropriate pressure is reached at higher elevations A default timing sequence for opening and closing inlet valves and outlet valves may be set by controller 400 which is based on an air pressure at or proximate to the pressure of air at sea level. At high altitudes, controller may alter the delay opening and closing of the valves to allow the compression system more time to collect and compress air. Delaying the timing sequence of the valves ensures that a canister reaches the appropriate pressure for oxygen enriched gas production, before being vented in preparation of the next cycle. Using a valve timing control scheme, the timing of the compression system would not be modified.

In an alternate embodiment, a combination of changing the motor speed and altering the timing of opening the valves can be used to ensure proper pressurization of the canisters. Oxygen concentrator may include a pressure sensor 176 disposed in the oxygen concentrator and coupled to controller 400 to determine an ambient pressure. Based on the ambient air pressure detected by pressure sensor 176, the controller may automatically modify the motor speed and/or the timing of the actuation of the valves to compensate for the reduced air pressure. The automatic adjustment of the operating conditions based on air pressure may be controlled by the user.

The altitude adjustment mode may be entered manually by the user, or automatically by the controller. For example, a user operated switch may be coupled to a controller. In an embodiment, the user operated switch allows the user to switch operation of the oxygen concentrator between a first mode of operation and a second mode of operation. In the first mode of operation, the program instructions are further operable to operate the compression system using default operating conditions, wherein the default operating conditions are not altered based on the ambient pressure sensed by the pressure sensor. In the second mode of operation, the program instructions are further operable to operate the compression system using modified operating conditions, wherein the modified operating conditions are altered based on the ambient pressure sensed by the pressure sensor. The user operated switch may be an "altitude" switch 640 on control panel 600.

When the oxygen concentrator system is in the second mode of operation, a signal (e.g., a light or an alarm) may be presented to the user. Alternatively, the oxygen concentrator system may display a light or produce an alarm when the ambient pressure is less than the ambient pressure at an elevation of 1000 meters, or 1500 meters, or 2000 meters. When an ambient pressure is detected that is less than the ambient pressure at an elevation of 1000 meters, or 1500 meters, or 2000 meters, a controller may: increase the rate of compression; increase the amount of compression; increase the compression cycle time; or perform combinations thereof, to compensate for the reduced air pressure.

The delivery of a bolus of oxygen enriched air to a user is based, in part on the air resistance of the environment. For example, in order to provide the bolus of oxygen enriched air to the user, the bolus must be released at a pressure sufficient to overcome the ambient pressure against the conduit leading to the user. At sea level the ambient pressure is significantly greater than at higher elevations. Thus, if no compensation is made for the higher elevation, the outward flow of the bolus will be too large and take too long. In one embodiment, the controller may modify the actuation of the supply valve to adjust the bolus delivery based on the detected ambient pressure. For example, the supply valve actuation may be adjusted to ensure that the oxygen and ambient air proportion provided to the patient is substantially identical to the ratios that would occur at sea level and result in a delivery that conforms to the patient's prescribed level of supplemental oxygen.

Positive Pressure Therapy Systems

Sleep apnea is a sleep disorder characterized by having one or more pauses in breathing or shallow breaths during sleep. Each pause in breathing, called an apnea, can last from a few seconds to minutes, and may occur 5 to 30 times or more an hour. For moderate to severe sleep apnea, the most common treatment is the use of a positive airway pressure, which helps to maintain an open airway during sleep by means of a flow of pressurized air into the patient's mouth and/or nose. The patient typically wears a mask that covers the nose and/or mouth and which is connected by a flexible tube to a small bedside compressor.

Positive pressure therapy relies on the use of pressurized air to assist in maintaining an open airway for the user while sleeping. There are various techniques that are used to accomplish this. One technique is known as continuous positive airway pressure (CPAP). In CPAP air is pushed from a flow generator through the tubing to a mask. The air then passes through the nose and/or mouth and into the throat, where the slight pressure keeps the upper airway open. During treatment by CPAP the pressure remains constant during use of the device. Automatic positive airway pressure (APAP) is an alternate method of applying pressurized air to a user's airway. In APAP, the positive air pressure applied to the user is continuously adjusted based on the breathing pattern of the patient. For example, if a sleep apnea episode is detected the pressure applied to the user may be increased to force the airway open. If the user is having difficulty exhaling or appears to be breathing normally, the pressure may be reduced to make the system more comfortable. Bi-level devices work by providing two different pressures of air to the user. During inhalation, a maximum pressure is provided to the user to ensure that the airway passages remain opened. The pressure is dropped during exhalation to make exhalation more comfortable for the user.

If a person suffering from sleep apneas is also in need of oxygen therapy significant amounts of oxygen may be required. As discussed above, positive pressure therapy of sleep apnea requires a constant pressure to be applied to the patient, while allowing release of pressurized air during exhalation. This is typically accomplished by use of a ventilated mask on the patient that allows some of the gas to flow out of the mask. This requires high flow rate (from 20-60 liters per minute) in order to achieve the required positive pressure. Since most oxygen concentrators can only produce up to about 10 LPM at most, it has been generally thought that oxygen concentrators could not be used in conjunction with positive pressure therapy.

Figure 15:
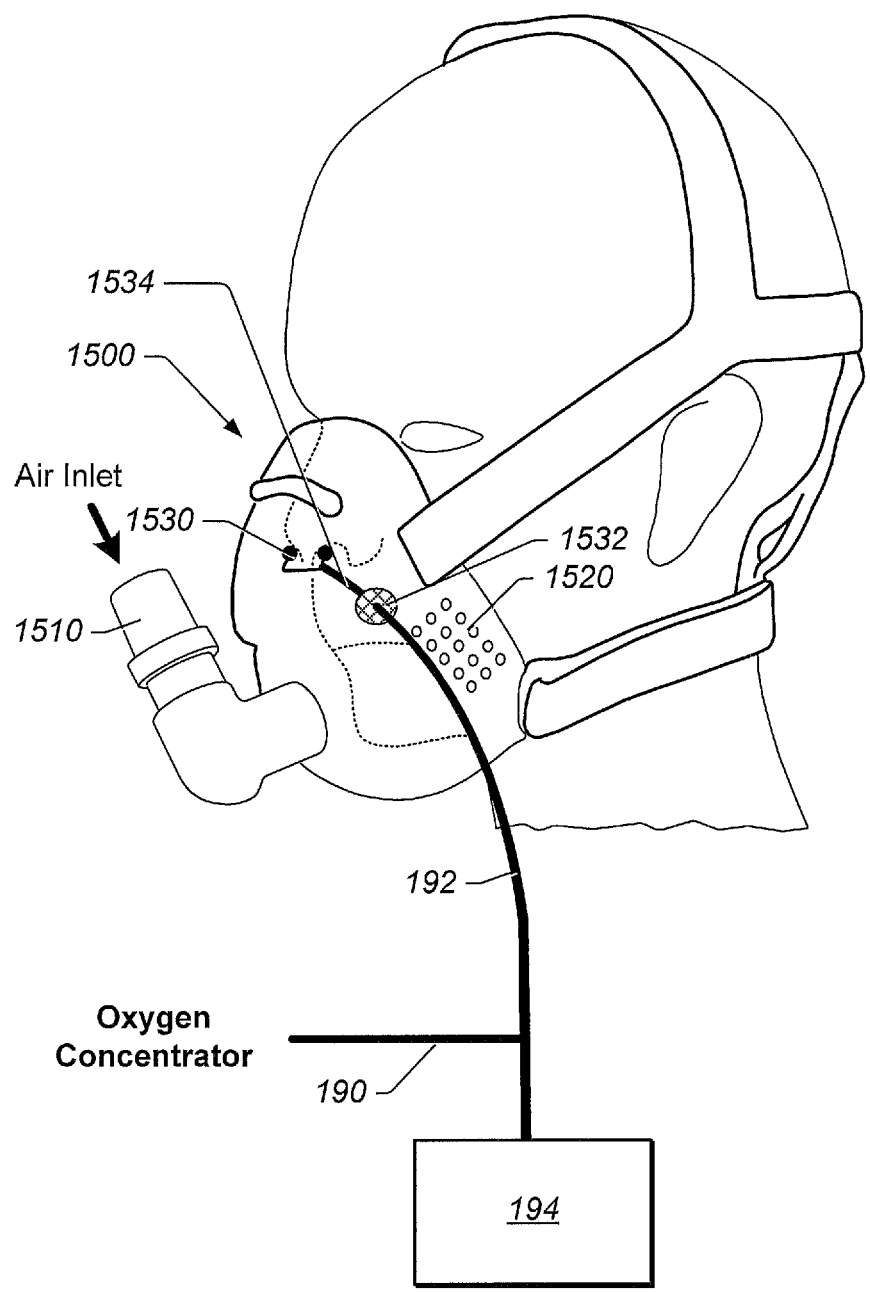
FIG. 15 depicts an embodiment of a mask for use with positive pressure therapy.

In one embodiment, an inhalation detection sensor (e.g., a pressure sensor or a flow rate sensor) may be coupled to a mask used for positive pressure therapy, and a pulse of oxygen enriched gas may be provided through a structure in the mask such that the bolus is sent directly into the air passages of the user (e.g., the nose or mouth) in spite of the continuous outflow of air from the mask that is an inherent feature of positive pressure treatment. One embodiment of a positive pressure therapy mask is depicted in FIG. 15. In FIG. 15, a positive pressure therapy mask 1500 is depicted. Positive pressure therapy mask 1500 includes a first conduit port 1510 for coupling to a compressed air source and a venting port 1520 for allowing a portion of the pressurized air entering the mask to exit. An oxygen concentrator, similar to the oxygen concentrators described herein, may be coupled to the mask via conduit 192. Conduit 192 may pass through the mask through second conduit port 1532 and rest near an air passage of the user. For example, a nasal cannula 1530 coupled to conduit 192 may be positioned proximate to the nose of the user to allow delivery of pulses of oxygen directly to the nose during use. Alternatively, a second conduit port 1532 may include a coupling that allows a conduit from an oxygen concentrator to be attaché to the mask. A separate conduit may extend from the mask to the user's nose to deliver oxygen enriched gas to the user. In such embodiments, a nasal cannula may be coupled to the second conduit port 1532 via conduit 1534. A pressure sensor 194 may be coupled to conduit 192 and conduit 190 may couple conduit 192 to an oxygen concentrator system. While the positive therapy mask 1500 is depicted as a full face mask (i.e., a mask that covers both nose and mouth) it should be understood that a similar configuration may be used on other kinds of masks including nasal masks, oral masks and total face masks.

Figure 16:
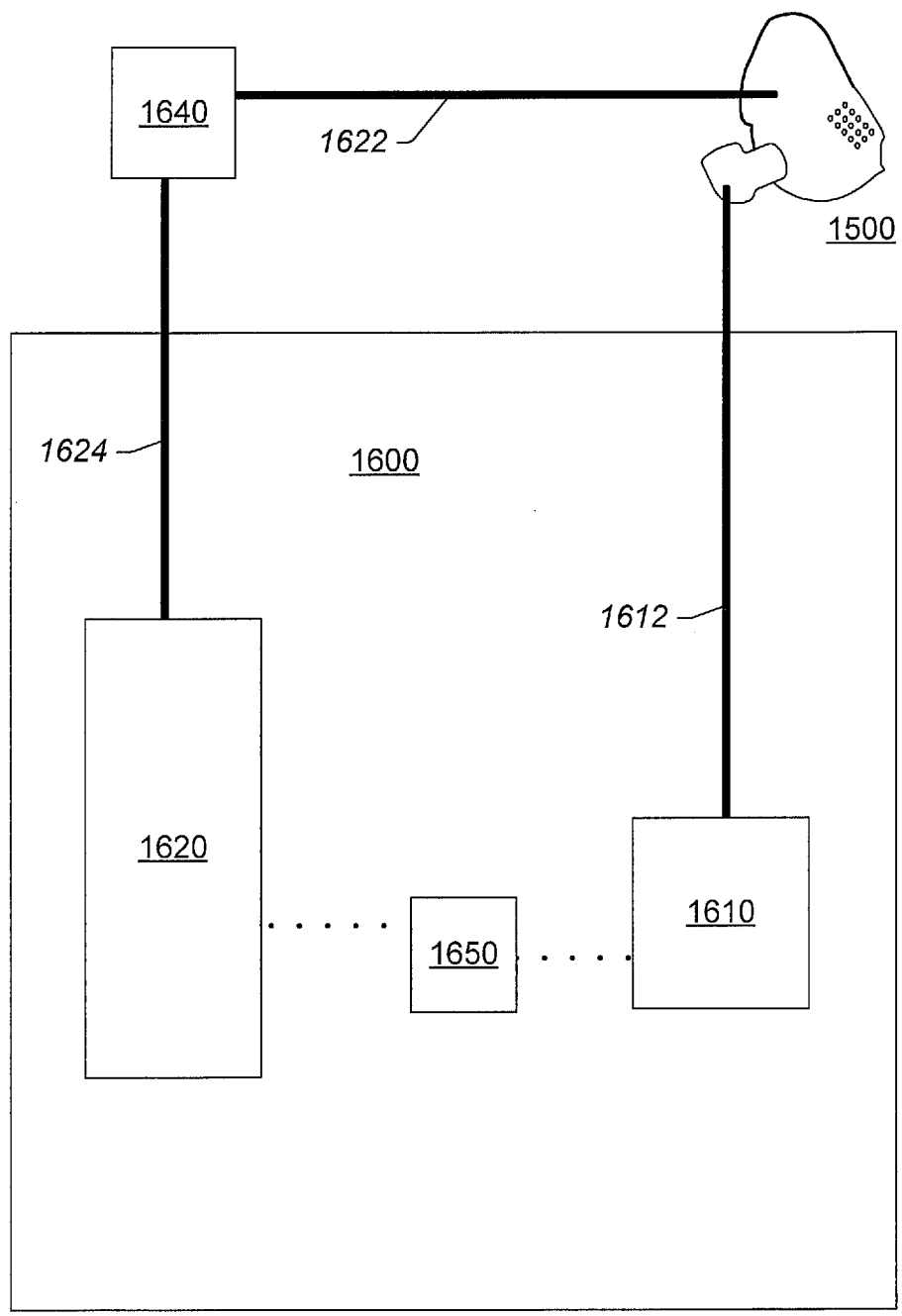
FIG. 16 depicts a schematic diagram of a positive pressure therapy system.

A schematic diagram of a positive pressure therapy system is depicted in FIG. 16. Positive therapy system 1600 includes compression system 1610, oxygen concentrator 1620, a mask 1500 and an inhalation sensor 1640. Mask 1500 is coupled to oxygen concentrator 1620 via conduits 1622 and 1624 through inhalation sensor 1640. Mask 1500 is also coupled to compression system 1610 via conduit 1612. The term "mask" as used herein refers to any device capable of providing a gas to nasal cavities or oral cavities. Examples of masks include, but are not limited to: nasal masks, nasal pillows, nasal prongs, oral masks, full face masks (e.g., masks that cover both the nose and the mouth), total face masks (e.g., masks that cover the mouth, nose, and eyes). The term "mask" also includes invasive gas delivery devices such as an endrotracheal tube, an oropharyngeal airway, or laryngeal mask. Operation of compression system 1610 and oxygen concentrator 1620 is controlled by controller 1650.

During use compression system 1610 produces a compressed air stream which is directed through conduit 1612 to mask 1500. Controller 1650 operates compression system 1610 to produce a stream of compressed air that is sufficient to meet the positive pressure therapy requirements of the user, typically producing compressed air having a flow rate of between about 20 LPM to 60 LPM. Controller 1650 is further coupled to inhalation sensor 1640. Inhalation sensor 1640 is coupled to mask 1500 and determines the onset of inhalation for the user by sensing a change in the air flow or pressure inside the mask. For example inhalation sensor may be a flow rate meter or a pressure sensor. Methods for detecting changes in pressure include methods discussed herein based on pressure changes and/or flow rate changes. At the onset of inhalation, controller 1650 may active a mechanism of the oxygen concentrator to release a bolus of oxygen directed directly to the user's airway via conduits 1622 and 1624.

Thus, oxygen is only provided when needed, minimizing the volume requirements of oxygen needed and allowing the patient to receive the prescribed oxygen.

When mask 1500 is coupled to the user, and compressed air is received by the mask from compression system 1610, a positive pressure (i.e. a pressure greater than the ambient pressure, builds up in the mask, due, in part to the restrictive venting of the mask. The positive pressure creates a condition such that the pressure measured by a pressure sensor coupled to the mask may never become negative. In such an embodiment, the onset of inhalation may be assessed by a significant drop in pressure, even if the drop in pressure still indicates a pressure in the mask that is above ambient pressure. Controller 1650 may therefore be configured to sense this condition and provide the bolus of oxygen enriched gas to user at the onset of inhalation.

For positive therapy systems that are based on APAP or bi-level control, controller 1650 may already be programmed to determine the breathing status of the patient, and make adjustments to the pressure in the mask. In an embodiment, controller 1650 may be configured to release a bolus of oxygen enriched gas from the oxygen concentrator system in synchronization with the pressure changing algorithm. For example, in an APAP device, the positive air pressure applied to the user is continuously adjusted based on the breathing pattern of the patient. Thus, an APAP device controller is already programmed to recognize when an increase in positive pressure is required to overcome resistance to breathing. Controller 1650 may include an APAP algorithm that is modified to also coordinate the release of an oxygen enriched gas from oxygen concentrator system when pressure is adjusted to stimulate breathing during a sleep apnea episode. In a bi-level system device the controller is already programmed to recognize when to increase the positive pressure during inhalation and when to decrease the pressure during exhalation. Controller 1650 may include a bi-level algorithm that is modified to also coordinate the release of an oxygen enriched gas from oxygen concentrator system when pressure is adjusted during inhalation.

During positive pressure therapy, a positive pressure is created inside the mask that is greater than ambient pressure. In one embodiment, a correction pressure is assessed by measuring ambient pressure and comparing ambient pressure to the pressure measured inside the mask. An ambient pressure sensor may be coupled to controller 1650 (e.g., ambient pressure sensor 176 in oxygen concentrator) and the ambient pressure measured. A correction pressure may be assessed as a function of the ambient pressure and the pressure inside of mask 1630. In one embodiment, the correction pressure is the difference between the pressure inside of mask 1630 and the ambient pressure. The pressure in the mask may be measured using a mask pressure sensor. During use, the pressure inside the mask may vary due to inhalation and exhalation of the user. In one embodiment, a correction pressure may be based on an average mask pressure measured over one or more breathing cycles. In another embodiment, a correction pressure may be based on a maximum mask pressure assessed over one or more breathing cycles. In another embodiment, a correction pressure may be based on a pressure in the mask when no breathing events (i.e., inhalation or exhalation) are occurring.

Once a correction pressure is assessed, operation of the oxygen generation system may be keyed to changes in pressure in the mask. During use the pressure in the mask is continuously or automatically measured. After each measurement, an adjusted mask pressure is assessed as a function of the measured mask pressure and the correction pressure. In one embodiment, the adjusted pressure is the difference between the measured pressure inside the mask and the correction pressure. In this embodiment, the onset of inhalation may be signaled by a drop in the adjusted pressure. If the adjusted pressure is less than a predetermined pressure, the system recognizes the onset of inhalation and provides a bolus of oxygen enriched gas to the user. Alternatively, since the adjusted pressure is corrected for ambient pressure, the onset of inhalation may be recognized when the adjusted pressure is less than ambient pressure. The correction pressure may be used by the system to automatically account for different mask pressures. Additionally, many oxygen concentrator systems are programmed to provide oxygen enriched air to the user when a pressure sensor detects a pressure below ambient pressure at the conduit used to provide oxygen enriched gas to the user. By using an adjusted pressure to signal the onset of inhalation, the oxygen concentrator system may need little if any adjustment.

During positive pressure therapy, a positive pressure is created inside the mask that is greater than ambient pressure. To prevent a continual increase of pressure inside the mask, masks used for positive pressure therapy have one or more venting ports built into the mask. This allows excess air to continuously exit the mask and also provides an outlet for exhalation. In one embodiment, a flow rate of air exiting the mask through one or more venting ports is assessed. During a breathing cycle the flow rate of the gasses exiting the mask will vary. When no breathing event occurs (i.e., when the patient is neither inhaling nor exhaling) the flow rate of gas exiting the mask is substantially constant and represents a baseline flow rate. During exhalation, the flow rate of gas exiting the mask will increase; during inhalation the flow rate of gas exiting the mask will decrease. During use the flow rate of gas exiting the mask is continuously or automatically measured. If the flow rate drops and is less than a baseline flow rate, the system recognizes the onset of inhalation and provides a bolus of oxygen enriched gas to the user. In an alternate embodiment, the onset of inhalation is recognized when the flow rate exiting the mask drops by a predetermined amount.

Figure 17:
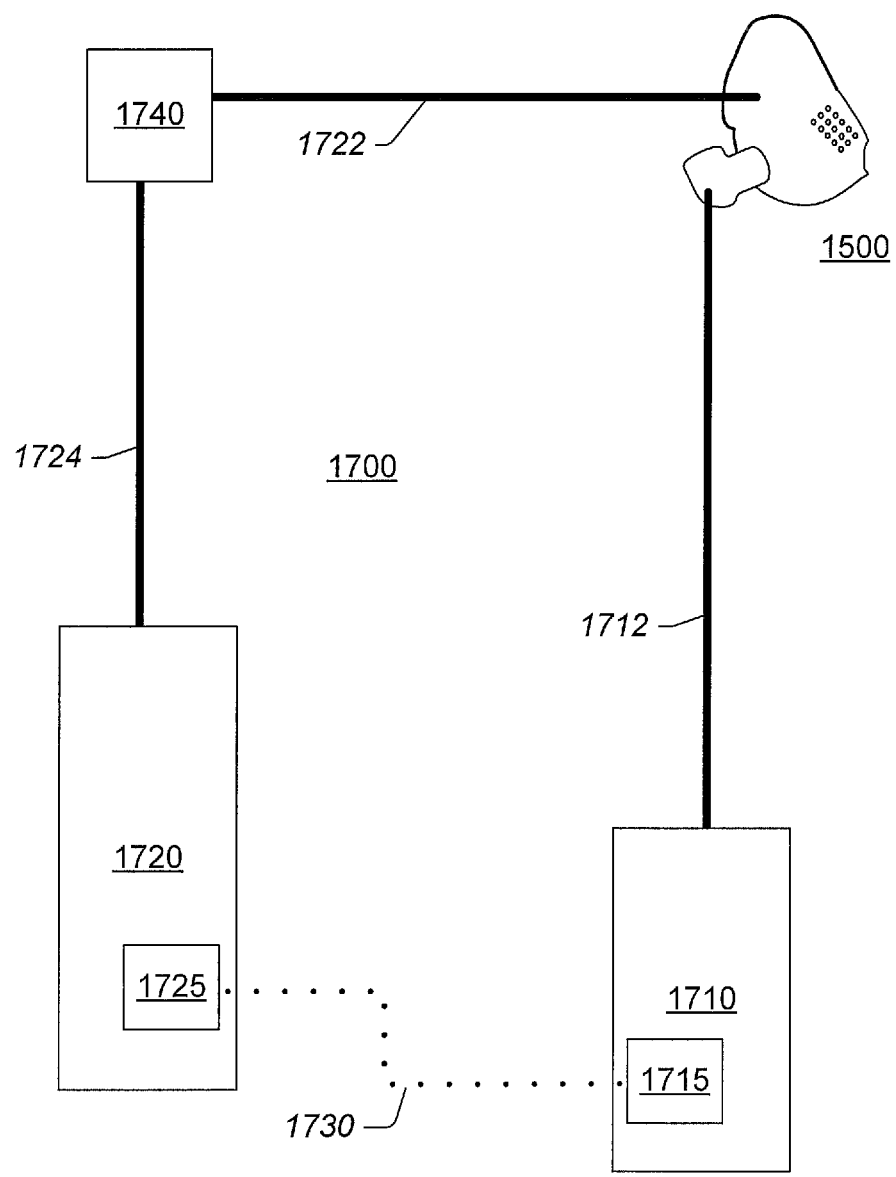
FIG. 17 depicts a schematic diagram of an alternate embodiment of a positive pressure therapy system.

In another embodiment, a system for positive pressure therapy includes an independent compression system for providing a substantially continuous flow of air to a mask (e.g., a CPAP, APAP, or Bi-level sleep apnea device) and an independent oxygen concentrator system. An oxygen concentrator system may be independently coupled to the mask and/or coupled to a continuous air flow delivery conduit. A schematic diagram of a positive pressure therapy system is depicted in FIG. 17. Positive therapy system 1700 includes compression system 1710, an oxygen concentrator system 1720, and a mask 1500. System 1700 also includes an inhalation sensor 1740 coupled to oxygen concentrator system 1720. Inhalation sensor may be separate from or an integral component of oxygen concentrator system 1720. Mask 1500 is coupled to oxygen concentrator system 1720 via conduits 1722 and 1724. Mask 1500 is also coupled to compression system 1710 via conduit 1712. Since both compression system 1710 and oxygen concentrator system 1720 are designed for independent use, each system includes a controller that directs operation of the system. Compression system 1710 include controller 1715 for directing the delivery of compressed air to the patient. Oxygen concentrator system 1720 includes controller 1725 for directing the production and delivery of oxygen enriched gas to the user. Compression system 1710 and oxygen concentrator system 1720 are removably couplable to mask 1500, such that the system can be used independently from each other.

During use compression system 1710 produces a compressed air stream which is directed through conduit 1712 to mask 1500. Controller 1715 operates compression system 1710 to produce a stream of compressed air that is sufficient to meet the positive pressure therapy requirements of the user, typically producing compressed air having a flow rate of between about 20 LPM to 60 LPM. Inhalation sensor 1740, coupled to mask 1500 and oxygen concentrator system 1720, determines the onset of inhalation for the user by sensing a change in the air flow or pressure inside the mask. For example inhalation sensor may be a flow rate meter or a pressure sensor. Methods for detecting changes in pressure include methods discussed herein based on pressure changes and/or flow rate changes. At the onset of inhalation, oxygen concentrator system controller 1725 may active a mechanism of the oxygen concentrator to release a bolus of oxygen directed directly to the user's airway via conduits 1722 and 1724. Thus, oxygen is only provided when needed, minimizing the volume requirements of oxygen needed and allowing the patient to receive the prescribed oxygen.

The detection of the onset of inhalation, as well as other information regarding the inhalation profile of the user, is useful for the operation of both compression system 1710 and oxygen concentrator system 1720. In one embodiment, to facilitate the coordination of the operation of compression system 1710 and oxygen concentrator system 1720, controller 1715 is couplable to controller 1725 via connection link 1730. Connection link 1730 may be embodied by a wired connection between controllers or may be a wireless connection. At least one of controllers 1715 and 1725 may be programmed to recognize the presence of the other controller along the connection link. Upon detection of another controller, one or both controllers operate to synchronize delivery of oxygen enriched gas with the delivery of pressurized air by the compression system. For example, in an APAP or bi-level device, the pressure of the air produced by the compression system various according to the breathing pattern of the user. The changes in pressure produced by the compression system may be used to control the delivery of oxygen enriched gas to the user, such that the delivery is synchronized with the pressure change. For example, when compression system initiates an increase in pressure to assist with inhalation, oxygen concentrator system may initiate delivery of oxygen enriched gas to the user.

Since the mask or other delivery device is under elevated pressure, the delivery flow rate of the oxygen concentrator is reduced. In one embodiment of the invention, the delivery valve of the oxygen concentrator is adjusted based on the pressure transducer reading of the internal mask pressure. This assures the system is delivering the correct bolus size that would otherwise be reduced by the resisting pressure in the mask.

Ventilator Systems

A positive pressure ventilator includes a compressed air source and a controller for providing the compressed air to the patient. Positive pressure ventilation works by forcing a breathing gas into the lungs, thereby increasing the pressure inside the airway and causing the lung to expand. When the pressurized air is discontinued, the patient will exhale passively due to the lungs' elasticity, the exhaled gas being released usually through a one-way valve within the conduits and mask coupled to the patient. As used herein the term "breathing gas" refers to a gas that is used by a user for respiration. Examples of breathing gases include, air, air/oxygen mixtures, nitrogen/oxygen mixtures, and pure oxygen. Air/oxygen and nitrogen/oxygen mixtures may vary in oxygen content from about 21% up to about 100% oxygen by volume.

In some instances, the person under ventilation may need more oxygen than is present in air. As discussed above, ventilation uses pulses of pressurized breathing gas that are applied to the patient to create inhalation for the patient, while allowing release of pressurized breathing gas during exhalation. This is typically accomplished by use of a ventilated mask on the patient that allows the gas to flow out of the mask when the pressurized air delivery is discontinued. In order to provide oxygen enriched gas to the patient, most ventilators rely on upstream mixing of oxygen from a compressed oxygen storage system (e.g., a compressed oxygen tank) with air or nitrogen to establish the proper oxygen level in the breathing gases provided to the patient.

In one embodiment, an inhalation detection sensor (e.g., a pressure sensor or a flow rate sensor) may be coupled to a mask used for ventilation, and a pulse of oxygen enriched gas may be provided through a structure in the mask such that the bolus is sent directly into the air passages of the user (e.g., the nose or mouth) during the pulsed delivery of pressurized breathing gas. The release of oxygen enriched gas may be at or near a time when a pulse of pressurized breathing gas is supplied to the mask.

Figure 18:
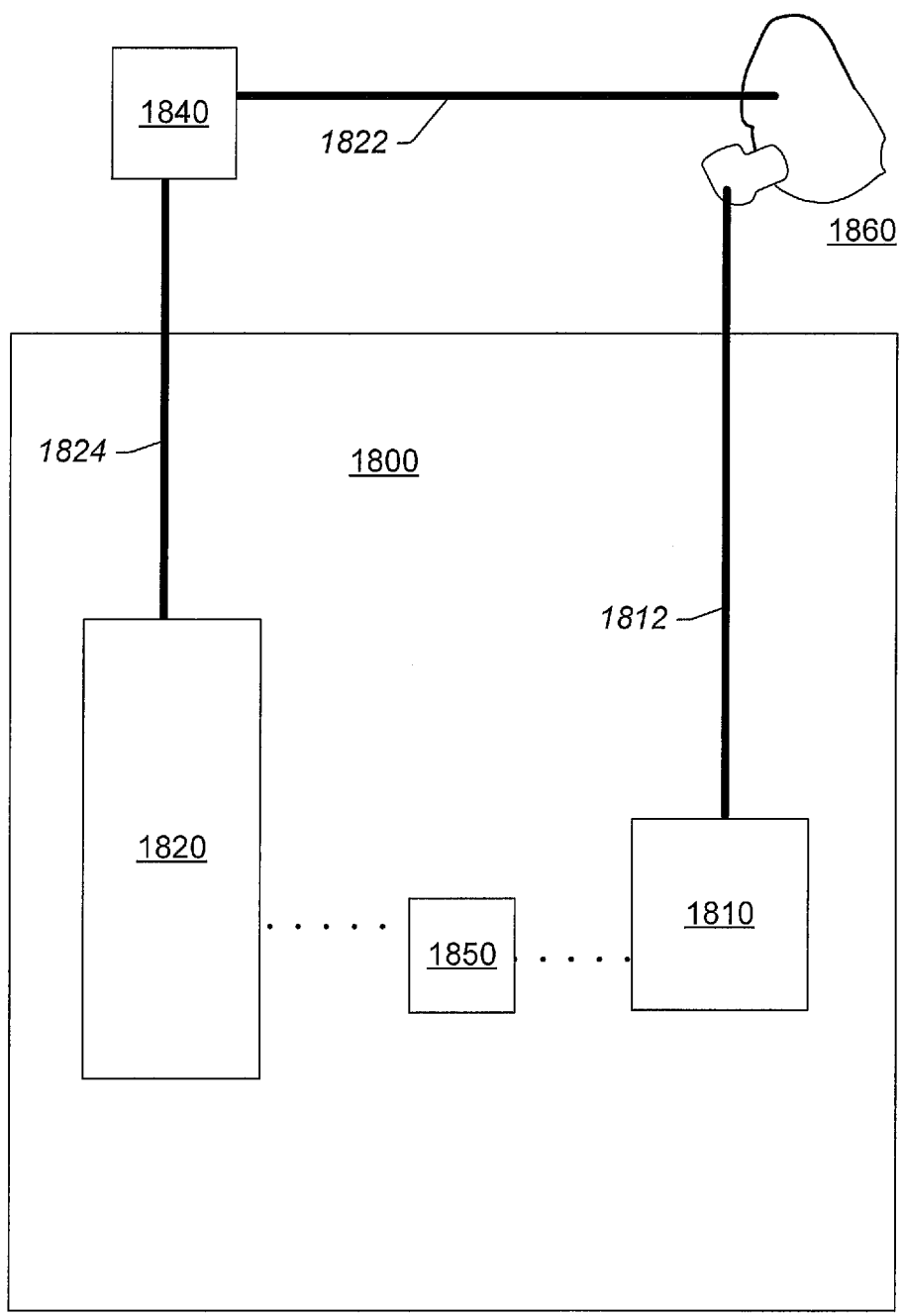
FIG. 18 depicts a schematic diagram of a ventilator system.

A schematic diagram of a ventilation system is depicted in FIG. 18. Ventilation system 1800 includes compression system 1810, oxygen concentrator 1820, a mask 1860 and an inhalation sensor 1840. Mask 1860 is coupled to oxygen concentrator 1820 via conduits 1822 and 1824 through inhalation sensor 1840. Mask 1860 is also coupled to compression system 1810 via conduit 1812. Operation of compression system 1810 and oxygen concentrator 1820 is controlled by controller 1850.

During use compression system 1810 produces a pulse of compressed breathing gas which is directed through conduit 1812 to mask 1860. Controller 1850 operates compression system 1810 to produce a pulse of pressurized breathing gas that is sufficient to expand the patient's lungs, creating an inhalation for the patient. Controller 1850 is further coupled to inhalation sensor 1840. Inhalation sensor 1840 is coupled to mask 1860 and determines the onset of inhalation for the user. In one embodiment, inhalation sensor 1840 is a pressure sensor that can detect a change in the pressure inside the mask. Methods for detecting changes in pressure include methods discussed herein based on pressure changes. At the onset of inhalation, controller 1850 may active a mechanism of the oxygen concentrator to release a bolus of oxygen directed directly to the user's airway via conduits 1822 and 1824. Thus, oxygen is only provided when needed, minimizing the volume requirements of oxygen needed and allowing the patient to receive the prescribed oxygen.

When mask 1860 is coupled to the user, and compressed breathing gas is received by the mask from compression system 1810, a positive pressure (i.e. a pressure greater than the ambient pressure, builds up in the mask. The positive pressure created in the mask initiates the inhalation portion of the breathing cycle for the patient. The onset of inhalation, therefore, may be assessed by a significant increase in pressure. Controller 1850 may therefore be configured to sense an increase in pressure in the mask and provide the bolus of oxygen enriched gas to user at the onset of inhalation.

Alternatively, controller 1850 may be programmed to provide pulses of compressed breathing gas to the patient at predetermined intervals. Thus, the onset of inhalation occurs at predetermined times and is known by controller. In one embodiment, controller 1650 may coordinate the release of oxygen enriched gas from oxygen concentrator 1820 with the delivery of the pressurized breathing gas from compression system 1810. Controller 1850 may be programmed to substantially simultaneously send signals to compression system 1810 and oxygen concentrator 1820 to initiate release of their respective gases to the patient.

Figure 19:
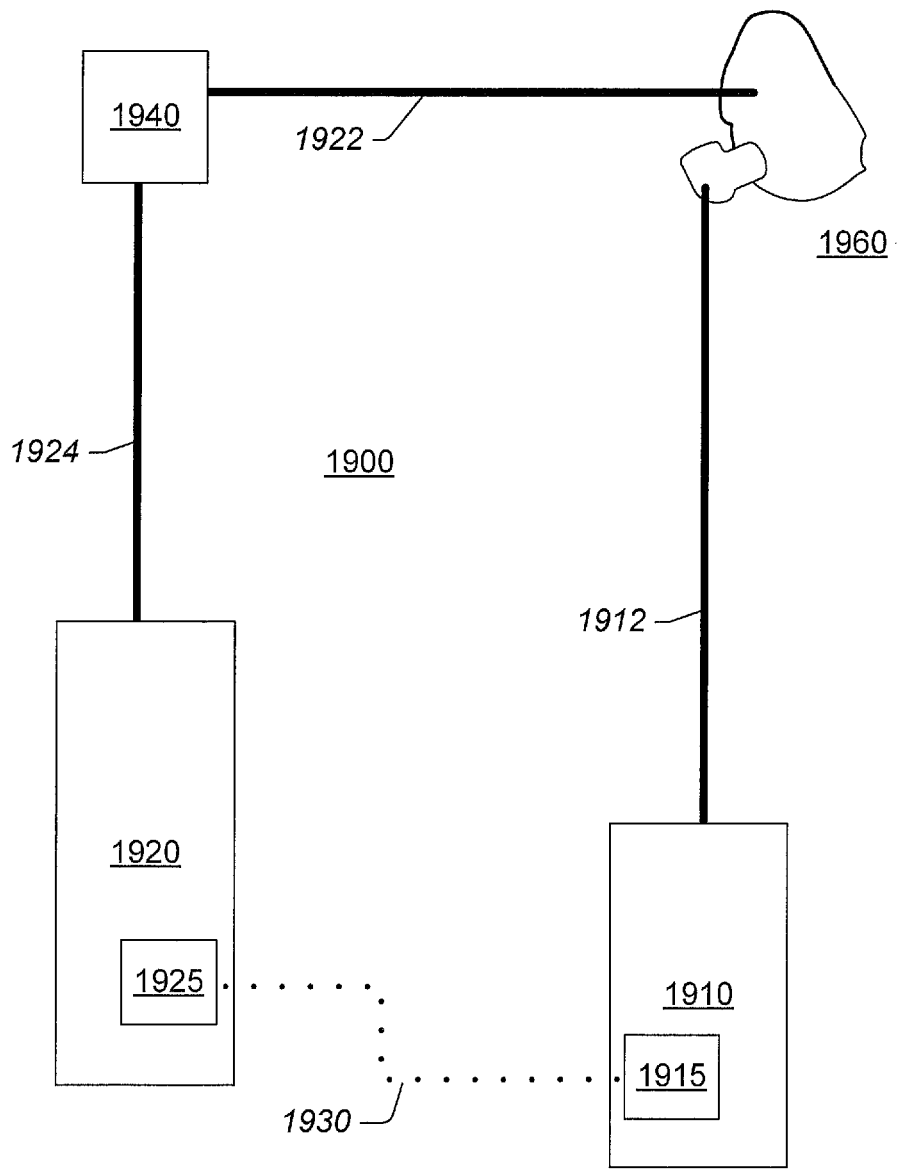
FIG. 19 depicts a schematic diagram of an alternate embodiment of a ventilator system.

In another embodiment, a ventilation system includes an independent compression system for providing pulses of breathing gas to a mask and an independent oxygen concentrator system. An oxygen concentrator system may be independently coupled to the mask and/or coupled to a breathing gas delivery conduit. A schematic diagram of a ventilation system is depicted in FIG. 19. Positive therapy system 1900 includes compression system 1910, an oxygen concentrator system 1920, and a mask 1960. System 1900 also includes an inhalation sensor 1940 coupled to oxygen concentrator system 1920. Inhalation sensor may be separate from or an integral component of oxygen concentrator system 1920. Mask 1960 is coupled to oxygen concentrator system 1920 via conduits 1922 and 1924. Mask 1960 is also coupled to compression system 1910 via conduit 1912. Since both compression system 1910 and oxygen concentrator system 1920 are designed for independent use, each of system includes a controller that directs operation of the system. Compression system 1910 include controller 1915 for directing the delivery of compressed air to the patient. Oxygen concentrator system 1920 includes controller 1925 for directing the production and delivery of oxygen enriched as to the user. Compression system 1910 and oxygen concentrator system 1920 are removably couplable to mask 1960, such that the system can be used independently from each other.

During use compression system 1920 produces a pulse of compressed breathing gas which is directed through conduit 1912 to mask 1960. Controller 1915 operates compression system 1910 to produce a pulse of compressed breathing gas that is sufficient induce or create inhalation in the patient. Inhalation sensor 1940, coupled to mask 1960 and oxygen concentrator system 1920, determines the onset of inhalation for the patient by sensing a change in the pressure inside the mask. For example, an onset of inhalation by the patient is indicated when the pressure inside the mask increases due to the delivery of a pulse of compressed breathing gas to the mask. At the onset of inhalation, oxygen concentrator system controller 1925 may active a mechanism of the oxygen concentrator to release a bolus of oxygen directed directly to the user's airway via conduits 1922 and 1924. Thus, oxygen is only provided when needed, minimizing the volume requirements of oxygen needed and allowing the patient to receive the prescribed oxygen.

In one embodiment, to facilitate the coordination of the operation of compression system 1910 and oxygen concentrator system 1920, controller 1915 is couplable to controller 1925 via connection link 1930. Connection link 1930 may be embodied by a wired connection between controllers or may be a wireless connection. At least one of controllers 1915 and 1925 may be programmed to recognize the presence of the other controller along the connection link. Upon detection of another controller, one or both controllers operate to synchronize delivery of oxygen enriched gas with the delivery a pulse of compressed breathing gas by the compression system. For example, when compression system initiates delivery of a pulse of compressed breathing gas, oxygen concentrator system may initiate delivery of oxygen enriched gas to the user.

As with the other positive airway adjustments above, the delivery valve of the oxygen concentrator is adjusted based on the resisting pressure in the mask or other delivery device of the ventilator so that the same size bolus of oxygen is delivered into the airstream being delivered to the patient.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An oxygen concentrator system, comprising:
   at least two canisters;
   gas separation adsorbent disposed in at least two canisters, wherein the gas separation adsorbent separates at least some nitrogen from air in the canister to produce oxygen enriched gas;
   a compression system coupled to at least one canister, wherein the compression system compresses air during operation;
   an internal power supply coupled to the compression system, the internal power supply providing power to operate at least the compression system during use; wherein the internal power supply comprises an internal power supply input port; and
   an auxiliary power supply removably coupleable to the internal power supply input port;
   the auxiliary power supply comprising:
      an auxiliary power supply body;
      one or more battery cells disposed in the auxiliary power supply body;
      a control circuit coupled to one or more of the battery cells, disposed in the auxiliary power supply body;
      an auxiliary power supply input port coupled to the control circuit; and
      an auxiliary power supply output connector coupled to the control circuit; wherein the auxiliary power supply output connector is used to removably couple the auxiliary power supply to the internal power supply input port during use;
   wherein the control circuit directs flow of current from the one or more battery cells to power the oxygen concentrator system when the auxiliary power supply output connector is coupled to the internal power supply input port.

2. The system of claim 1, wherein the auxiliary power supply output connector is removably couplable to the auxiliary power supply input port, and wherein the control circuit places the auxiliary power supply in a standby mode when the auxiliary power supply output connector is coupled to the auxiliary power supply input port.

3. The system of claim 1, wherein the control circuit comprises:
- a buck converter coupled to the auxiliary power supply input port, wherein the buck convertor steps down the input voltage to an input voltage appropriate to charge one or more of the battery cells;
- a boost convertor coupled to one or more of the battery cells, wherein the boost convertor boosts the voltage from one or more of the battery cells;
- a power path controller coupled to the auxiliary power supply input port and the boost convertor; and
- a current limit protector coupled to the auxiliary power supply output connector, wherein the output current of the auxiliary power supply flows through the current limit protector to the auxiliary power supply output connector;
- wherein the power path controller conditionally couples the auxiliary power supply input port or the boost convertor to the current limit protector; as follows:
  - when an external charger is coupled to the auxiliary power supply input port, the power path controller couples the auxiliary power supply input port to the current limit protector; and
  - when an external charger is not coupled to the auxiliary power supply input port, the power path controller couples the boost convertor to the current limit protector.

4. The system of claim 3, wherein the boost convertor and the buck convertor are disabled when the auxiliary power supply output connector is coupled to the auxiliary power supply input port.

5. The system of claim 3, wherein the boost converter is disabled and the buck convertor is enabled when the external charger is coupled to the auxiliary power supply input port and the voltage of the external charger exceeds the voltage of one or more of the battery cells of the auxiliary power supply.

6. The system of claim 5, wherein the power path controller enables a channel coupling the external charger to the auxiliary power supply output connector of the auxiliary power supply, when the external charger is coupled to the auxiliary power supply input port.

7. The system of claim 1, further comprising a control circuit coupled to the internal power supply and the internal power supply input port, wherein the control circuit automatically detects current flowing to the internal power supply and automatically controls the flow of current to the internal power supply.

8. The system of claim 1, further comprising a processor, coupled to the compression system and the internal power supply, operable to execute program instructions, wherein the program instructions are operable to perform the method comprising:
- assessing the voltage produced by one or more battery cells of the internal power supply;
- adjusting the battery cell being used to apply a current to the compression system based on one or more assessed voltages.

9. The system of claim 1, further comprising a processor, coupled to the compression system and the internal power supply, operable to execute program instructions, wherein the program instructions are operable to perform the method comprising:
- assessing the temperature of the internal power supply;
- interrupting operation of at least the compression system if the temperature of the internal power supply is greater than a predetermined temperature.

10. The system of claim 1, further comprising a processor, coupled to the compression system and the internal power supply, operable to execute program instructions, and wherein the program instructions are operable to perform the method comprising:
- assessing if the auxiliary power supply is coupled to the internal power supply input port;
- operating at least the compression system using current from the auxiliary power supply, when the auxiliary power supply is coupled to the internal power supply input port, until the auxiliary power supply has insufficient power to operate at least the compression system; and
- operating at least the compression system using current from the internal power supply, when the auxiliary power supply is connected to the internal power supply input port, if the auxiliary power supply has insufficient power to operate at least the compression system.

11. The system of claim 1, wherein the internal power supply comprises a lithium ion battery.

12. The system of claim 1, wherein the auxiliary power supply comprises a lithium ion battery.

13. The system of claim 1, wherein the auxiliary power supply output connector is removable connectable to the internal power supply input port and the auxiliary power supply output connector is removably connectable to the auxiliary power supply input port.

14. The system of claim 1, further comprising an external charger removable couplable to the internal power supply and the auxiliary power supply, the external charger comprising an external charger output connector used to removably couple the external charger to the internal power supply input port and removable couple the external charger to the auxiliary power supply input port.

15. The system of claim 14, wherein the external charger output connector is removable connectable to the internal power supply input port and the external charger output connector is removably connectable to the auxiliary power supply input port.

16. The system of claim 1, further comprising a processor, coupled to the compression system and the internal power supply, operable to execute program instructions, wherein the program instructions are operable to perform the method comprising delivering a bolus of the oxygen to a user in two or more pulses; wherein a volume of the bolus is approximately an amount of oxygen determined to be delivered to the user during a single breath.

17. The system of claim 1, comprising:
- a first canister containing gas separation adsorbent;
- a second canister containing gas separation adsorbent; and
- a manifold comprising one or more conduits coupling the first canister to the second canister;
- wherein at least a portion of the first canister, at least a portion of the second canister, and a portion of the manifold are molded together to form a single molded component, wherein at least a portion of the conduits are in the form of at least one molded channel in the molded component.

18. The system of claim 1, further comprising an accumulation chamber coupled to one or more of the canisters, wherein oxygen enriched gas produced in one or more of the canisters is stored in the accumulation chamber.

19. The system of claim 18, further comprising an oxygen sensor coupled to the accumulation chamber, wherein the oxygen sensor is capable of detecting oxygen in a gas during use.

20. The system of claim 1, further comprising a processor, operable to execute program instructions, wherein the program instructions are operable to produce an alarm or other signal in response to a stoppage of inhalation for a predetermined amount of time.

21. The system of claim 1, further comprising a processor, coupled to the compression system and the internal power supply, operable to execute program instructions, wherein the program instructions are operable to:
   determine if the user is in an active state or a sedentary state;
   implement a first mode of providing oxygen enriched gas to the user if the user is in an active state; and
   implement a second mode of providing oxygen enriched gas if the user is in a sedentary state.

22. The system of claim 1, further comprising:
   a first canister containing gas separation adsorbent;
   a second canister containing gas separation adsorbent; and
   one or more conduits coupling the first canister to the second canister;
   wherein one or more of the conduits couple the first canister to the second canister such that at least part of oxygen enriched gas from the first canister is diverted through the second canister during at least part of a venting process of the second canister; and
   wherein one or more of the conduits couple the first canister to the second canister such that at least part of oxygen enriched gas from the second canister is diverted through the first canister during at least part of a venting process of the first canister.

23. The system of claim 1, wherein the oxygen concentrator apparatus has a weight of less than about 5 lbs.

24. An oxygen concentrator system, comprising:
   at least two canisters;
   gas separation adsorbent disposed in at least two canisters, wherein the gas separation adsorbent separates at least some nitrogen from air in the canister to produce oxygen enriched gas;
   a compression system coupled to at least one canister, wherein the compression system compresses air during operation;
   an internal power supply coupled to the compression system, the internal power supply providing power to operate the compression system during use; wherein the internal power supply comprises an internal power supply input port; and
   an auxiliary power supply removably connectable to the internal power supply input port;
   the auxiliary power supply comprising:
      an auxiliary power supply body;
      one or more battery cells disposed in the auxiliary power supply body;
      a control circuit coupled to one or more of the battery cells, disposed in the auxiliary power supply body;
      an auxiliary power supply input port coupled to the control circuit; and
      an auxiliary power supply output connector used to removably connect the auxiliary power supply to the internal power supply input port during use; wherein the auxiliary power supply output connector is removably connectable to the auxiliary power supply input port;
      wherein the control circuit places the auxiliary power supply in a standby mode when the auxiliary power supply output connector is connected to the auxiliary power supply input port.

25. The system of claim 24, further comprising:
an external charger removable connectable to the internal power supply and the auxiliary power supply, the external charger comprising an external charger output connector used to removably connect the external charger to the internal power supply input port and removable connect the external charger to the auxiliary power supply input port.

* * * * *